(12) United States Patent
Chang et al.

(10) Patent No.: US 7,771,409 B2
(45) Date of Patent: Aug. 10, 2010

(54) DEVICES, SYSTEMS AND METHODS USEABLE FOR TREATING SINUSITIS

(75) Inventors: John Y. Chang, Mountain View, CA (US); Joshua Makower, Los Altos, CA (US); Julia D. Vrany, Sunnyvale, CA (US); John H. Morriss, Portola Valley, CA (US); Ketan P. Muni, San Jose, CA (US); Isaac J. Kim, San Jose, CA (US); Hung Ha, San Jose, CA (US); William M. Facteau, Mountain View, CA (US)

(73) Assignee: Acclarent, Inc., Menlo Park, CA (US)

( * ) Notice: Subject to any disclaimer, the term of this patent is extended or adjusted under 35 U.S.C. 154(b) by 302 days.

(21) Appl. No.: 11/928,160

(22) Filed: Oct. 30, 2007

(65) Prior Publication Data
US 2009/0093823 A1 Apr. 9, 2009

Related U.S. Application Data

(63) Continuation of application No. 11/150,847, filed on Jun. 10, 2005, which is a continuation-in-part of application No. 10/944,270, filed on Sep. 17, 2004, which is a continuation-in-part of application No. 10/829,917, filed on Apr. 21, 2004.

(51) Int. Cl.
*A61M 31/00* (2006.01)

(52) U.S. Cl. .................................................... 604/514

(58) Field of Classification Search ............... 604/96.01, 604/101.01, 500, 514; 600/104–107, 153; 606/191–194

See application file for complete search history.

(56) References Cited

U.S. PATENT DOCUMENTS 504,424 A 9/1893 De Pezzer
(Continued)

FOREIGN PATENT DOCUMENTS

CH 668188 12/1988
(Continued)

OTHER PUBLICATIONS

Gottman, et al.; Balloon Dilation of Recurrent Ostial Occlusion of the frontal sinus; Abstract No. B-04353, European Congress of Radiology, pp. 1-4, Mar. 2001.
(Continued)

*Primary Examiner*—Manuel A Mendez
(74) *Attorney, Agent, or Firm*—Steptoe & Johnson LLP

(57) ABSTRACT

Sinusitis and other disorders of the ear, nose and throat are diagnosed and/or treated using minimally invasive approaches with flexible or rigid instruments. Various methods and devices are used for remodeling or changing the shape, size or configuration of a sinus ostium or duct or other anatomical structure in the ear, nose or throat; implanting a device, cells or tissues; removing matter from the ear, nose or throat; delivering diagnostic or therapeutic substances or performing other diagnostic or therapeutic procedures. Introducing devices (e.g., guide catheters, tubes, guidewires, elongate probes, other elongate members) may be used to facilitate insertion of working devices (e.g. catheters e.g. balloon catheters, guidewires, tissue cutting or remodeling devices, devices for implanting elements like stents, electrosurgical devices, energy emitting devices, devices for delivering diagnostic or therapeutic agents, substance delivery implants, scopes etc.) into the paranasal sinuses or other structures in the ear, nose or throat. Specific devices (e.g., tubular guides, guidewires, balloon catheters, tubular sheaths) are provided as are methods for manufacturing and using such devices to treat disorders of the ear, nose or throat.

9 Claims, 41 Drawing Sheets

U.S. PATENT DOCUMENTS

| | | |
|---|---|---|
| 705,346 A | 7/1902 | Hamilton |
| 2,525,183 A | 10/1950 | Robison |
| 3,800,788 A | 4/1974 | White |
| 3,859,993 A | 1/1975 | Bitner |
| 4,102,342 A | 7/1978 | Akiyama et al. |
| 4,338,941 A | 7/1982 | Payton |
| 4,437,856 A | 3/1984 | Valli |
| 4,581,017 A | 4/1986 | Sahota |
| 4,637,389 A | 1/1987 | Heyden |
| 4,737,141 A | 4/1988 | Spits |
| 4,748,969 A | 6/1988 | Wardle |
| 4,755,171 A | 7/1988 | Tennant |
| 4,811,743 A | 3/1989 | Stevens |
| 4,883,465 A | 11/1989 | Brennan |
| 5,021,043 A | 6/1991 | Becker et al. |
| 5,139,832 A | 8/1992 | Hayashi et al. |
| 5,167,220 A | 12/1992 | Brown |
| 5,168,864 A | 12/1992 | Shockey |
| 5,169,386 A | 12/1992 | Becker et al. |
| 5,207,695 A | 5/1993 | Trout, III |
| 5,336,163 A | 8/1994 | DeMane et al. |
| 5,346,075 A | 9/1994 | Nichols et al. |
| 5,441,497 A | 8/1995 | Narciso, Jr. |
| 5,451,221 A | 9/1995 | Cho et al. |
| 5,454,817 A | 10/1995 | Katz |
| 5,496,338 A | 3/1996 | Miyagi et al. |
| 5,546,964 A | 8/1996 | Stangerup |
| 5,549,542 A | 8/1996 | Kovalcheck |
| 5,578,048 A | 11/1996 | Pasqualucci et al. |
| 5,599,304 A | 2/1997 | Shaari |
| 5,601,594 A | 2/1997 | Best |
| 5,664,567 A | 9/1997 | Linder |
| 5,693,065 A | 12/1997 | Rains, III |
| 5,789,391 A | 8/1998 | Jacobus et al. |
| 5,827,224 A | 10/1998 | Shippert |
| 5,872,879 A | 2/1999 | Hamm |
| 5,902,247 A | 5/1999 | Coe et al. |
| 5,928,192 A | 7/1999 | Maahs |
| 5,949,929 A | 9/1999 | Hamm |
| 5,980,551 A | 11/1999 | Summers et al. |
| 5,997,562 A | 12/1999 | Zadno-Azizi et al. |
| 6,027,478 A | 2/2000 | Katz |
| 6,053,172 A | 4/2000 | Hovda et al. |
| 6,083,188 A | 7/2000 | Becker |
| 6,109,268 A | 8/2000 | Thapliyal et al. |
| 6,113,567 A | 9/2000 | Becker |
| 6,142,957 A | 11/2000 | Diamond et al. |
| 6,190,381 B1 | 2/2001 | Olsen et al. |
| 6,238,364 B1 | 5/2001 | Becker |
| 6,238,391 B1 | 5/2001 | Olsen et al. |
| 6,293,957 B1 | 9/2001 | Peters et al. |
| 6,352,503 B1* | 3/2002 | Matsui et al. ............... 600/104 |
| 6,394,093 B1 | 5/2002 | Lethi |
| 6,425,877 B1 | 7/2002 | Edwards |
| 6,450,989 B2 | 9/2002 | Dubrul et al. |
| 6,536,437 B1 | 3/2003 | Dragisic |
| 6,537,294 B1 | 3/2003 | Boyle et al. |
| 6,596,009 B1 | 7/2003 | Jelic |
| 6,663,589 B1 | 12/2003 | Halevy |
| 6,685,648 B2 | 2/2004 | Flaherty et al. |
| 6,716,813 B2 | 4/2004 | Lim et al. |
| 6,776,772 B1 | 8/2004 | Vrijer et al. |
| 6,796,960 B2 | 9/2004 | Cioanta et al. |
| D501,677 S | 2/2005 | Becker |
| 7,011,654 B2 | 3/2006 | Dubrul et al. |
| 7,022,105 B1 | 4/2006 | Edwards |
| 7,056,303 B2 | 6/2006 | Dennis et al. |
| 7,131,969 B1 | 11/2006 | Hovda et al. |
| 7,169,163 B2 | 1/2007 | Becker |
| 7,381,205 B2 | 6/2008 | Thommen |
| 7,442,191 B2 | 10/2008 | Hovda et al. |
| 7,454,244 B2 | 11/2008 | Kassab, et al. |
| 7,462,175 B2 | 12/2008 | Chang et al. |
| 7,500,971 B2 | 3/2009 | Chang et al. |
| 2004/0058992 A1 | 3/2004 | Marinello et al. |
| 2004/0064083 A1 | 4/2004 | Becker |
| 2004/0064150 A1* | 4/2004 | Becker ...................... 606/196 |
| 2006/0004323 A1 | 1/2006 | Chang et al. |
| 2006/0149310 A1 | 7/2006 | Becker |
| 2006/0210605 A1 | 9/2006 | Chang et al. |
| 2007/0073269 A1 | 3/2007 | Becker |
| 2007/0250105 A1 | 10/2007 | Ressemann et al. |
| 2008/0097515 A1 | 4/2008 | Chang et al. |

FOREIGN PATENT DOCUMENTS

| | | |
|---|---|---|
| CN | 2151720 U | 1/1994 |
| DE | 10105592 A1 | 2/2001 |
| EP | 0129634 A1 | 1/1985 |
| EP | 0418391 B1 | 7/1991 |
| EP | 0585757 A1 | 3/1994 |
| EP | 0624349 A1 | 5/1994 |
| RU | 2212530 | 10/2003 |
| SU | 1662571 | 7/1991 |
| WO | 90/11053 | 10/1990 |
| WO | 90/14865 | 12/1990 |
| WO | 91/17787 | 11/1991 |
| WO | 92/15286 | 2/1992 |
| WO | 96/29071 | 9/1996 |
| WO | 99/30655 | 6/1999 |
| WO | 00/53252 | 9/2000 |
| WO | 02/062269 | 8/2002 |
| WO | 03/105657 | 12/2003 |
| WO | 2004/006788 | 1/2004 |
| WO | 2008051918 | 5/2008 |

OTHER PUBLICATIONS

Gottman, et al.; Balloon Dilatation of Recurrent Ostial Occlusion of the frontal sinus; ECR, pp. 1-57, Mar. 2, 2001.

Gottman, et al.; Balloon Dilatation in the nasal cavity and paranasal sinuses; CIRSE, pp. 1-27, Sep. 25, 2004.

Robison, J. Mathews, M.D., Pressure Treatment of Purulent Maxillary Sinusitis, Texas State Journal of Medicine, pp. 281-288, May 1951.

Robison, J. Mathews, M.D., Pressure Treatment of Maxillary Sinusitis, J.A.M.A., pp. 436-440, May 31, 1952.

Strohm et al.; Die Behandlung von Stenosen der oberen Luftwege mittels rontgenologisch gesteuerter Ballondilation, pp. 1-4, Sep. 25, 1999.

Woog, et al., Paranasal Sinus Endoscopy and Orbital Fracture Repair, Arch Ophthalmol, vol. 116, May 1998, pp. 688-691.

Friedman, et al., Intraoperative and Postoperative Assessment of Frontal Sinus Patency by Transillumination, Laryngoscope 110: Apr. 2000, pp. 683-684.

Binner, et al., Fibre-Optic Transillumination of the Sinuses: A Comparison of the Value of Radiography and Transillumination in Antral Disease, Clinical Otolaryngology, 1978, 3, pp. 1-11.

Hybels, Transillumination During Osteoplastic Frontal Sinusotomy, The Laryngoscope 91: Sep. 1981, p. 1560.

Stammberger, et al., Special Endoscopic Anatomy of the Lateral Nasal Wall and Ethmoidal Sinuses, Functional Endoscopic Sinus Surgery, 1991, Ch. 3, pp. 49-87.

Kuhn, et al., The Agger Nasi Cell in Frontal Recess Obstruction: An Anatomic, Radiology and Clinical Correlation, Operative Techniques in Otolaryngology-Head and Neck Surgery, vol. 2, No. 4, 1991, pp. 226-231.

Bent, et al., The Frontal Cell as a Cause of Frontal Sinus Obstruction, American Journal of Rhinology, vol. 8, No. 4, 1994, pp. 185-191.

Casiano, et al., Endoscopic Lothrop Procedure: The University of Miami Experience, American Journal of Rhinology, vol. 12, No. 5, 1998, pp. 335-339.

Benninger, et al., Adult Chronic Rhinosinustis: definitions, diagnosis, epidemiology, and pathophysiology; Arch Otolaryngol Head and Neck Surg; vol. 129, p. S1-S-22; Sep. 2003.

Barrett, Steven, Be Wary of Neurocranial Restructuring (NCR). Chirobase (available at: http://www.chirobase.org/06DD/ncr.html) Jul. 2003.

Croix, et al., "Genes Expressed in Human Tumor Endothelium"; Science vol. 289, pp. 1197-1202; May 2000.

Davis, et al., A Complication From Neurocranial Restructuring; Arch Otolarygol Head and Neck Surg; vol. 129, p. 472-474; Apr. 2003.

Göttman, et al., Successful Treatment of Recurrent Post-operative Frontal Sinus Stenoses by Balloon Dilatation; Cirse, Oct. 5, 2002.

USPTO Office Action dated Oct. 29, 2008 in U.S. Appl. No. 11/347,147, filed Feb. 2, 2006.

USPTO Office Action dated Mar. 3, 2009 in U.S. Appl. No. 12/117,582, filed May 8, 2008.

USPTO Office Action dated Nov. 25, 2008 in U.S. Appl. No. 12/117,961, filed May 9, 2008.

USPTO Office Action dated Mar. 4, 2009 in U.S. Appl. No. 12/118,931, filed May 12, 2008.

USPTO Office Action dated Dec. 5, 2008 in U.S. Appl. No. 12/120,902, filed May 15, 2008.

USPTO Office Action dated Nov. 7, 2008 in U.S. Appl. No. 10/944,270, filed Sep. 17, 2004.

Göttman, et al.; Balloon Dilation of Recurrent Ostial Occlusion of the frontal sinus; Abstract No. B-04353, European Congress of Radiology Mar. 2001.

Göttman, et al., Balloon dilatation in the nasal cavity and paranasal sinuses; CIRSE, Sep. 25, 2004.

Robison, J. Matthews, M.D., Pressure Treatment of Purulent Maxillary Sinusitis, Texas State Journal of Medicine, May 1951, pp. 281-288.

Robison, J. Matthews, M.D., Pressure Treatment of Maxillary Sinusitis, J.A.M.A., May 31, 1952, pp. 436-440.

Strohm, et al., Die Behandlung von Stenosen der oberen Luftwege mittels röntgenologisch gesteuerter Balloondilation, Sep. 25, 1999.

Lanza, Donald C., "Postoperative Care and Avoiding Frontal Recess Stenosis", International Advanced Symposium, Jul. 21-24, 1993.

Kennedy, David W., M.D., et al., "Diseases of the Sinuses Diagnosis and Management", Copyright 2001 by B.C. Decker Inc.

Schaefer, Steven D., M.D., "Rhinology and Sinus Disease a Problem-Oriented Approach", Copyright 1988 by Mosby, Inc.

Friedman, Michael, M.D., et al., "Operative Techniques in Otolaryngology-Head and Neck Surgery", vol. 12, No. 2, Jun. 2001, pp. 60-65.

Office Action dated Sep. 16, 2005 in U.S. Appl. No. 10/259,300.

Office Action dated Jul. 7, 2006 in U.S. Appl. No. 10/259,300.

Office Action dated Feb. 13, 2007 in U.S. Appl. No. 10/259,300.

Office Action dated Oct. 9, 2007 in U.S. Appl. No. 10/259,300.

Office Action dated Jan. 24, 2008 in U.S. Appl. No. 10/259,300.

Office Action dated Oct. 6, 2008 in U.S. Appl. No. 10/259,300.

Office Action dated Mar. 17, 2009 in U.S. Appl. No. 11/690,127.

\* cited by examiner

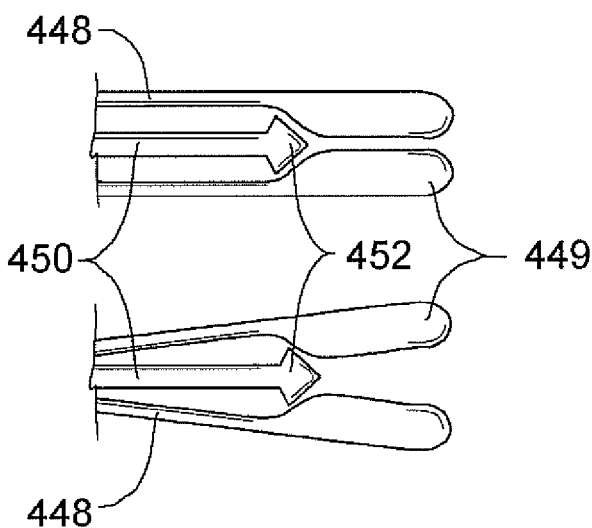
Fig. 4L
Fig. 4M
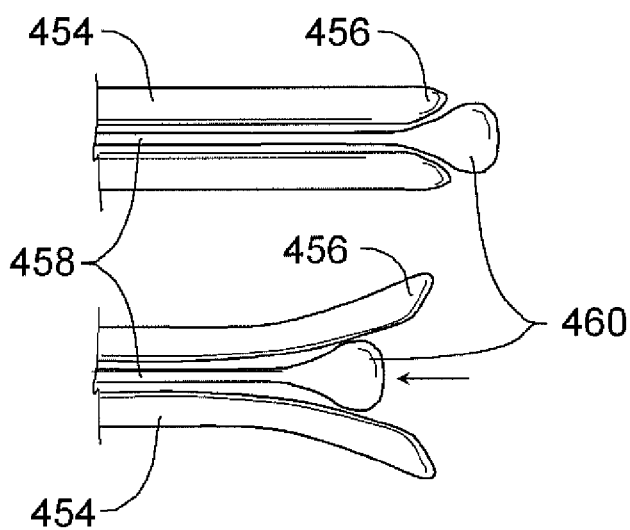
Fig. 4N
Fig. 4O
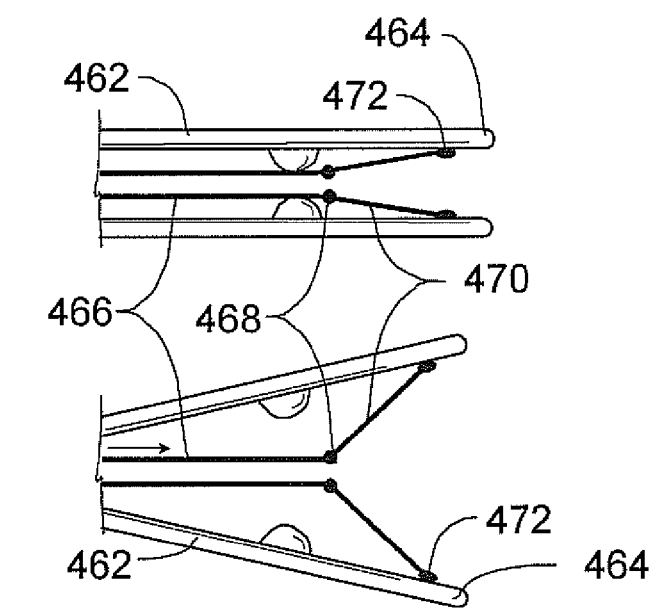
Fig. 4P
Fig. 4Q

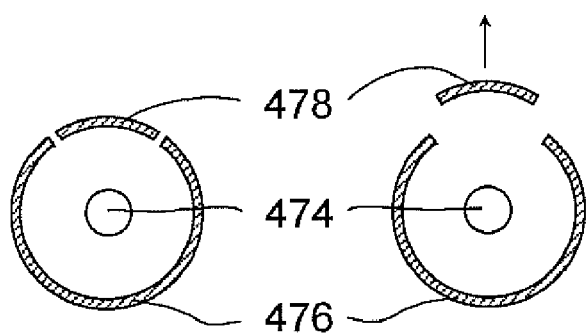 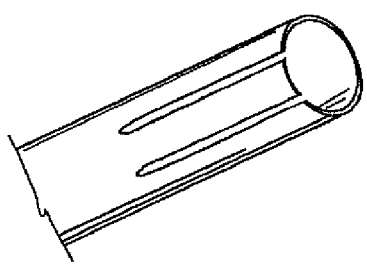
Fig. 4R　　　Fig. 4S　　　Fig. 4S'
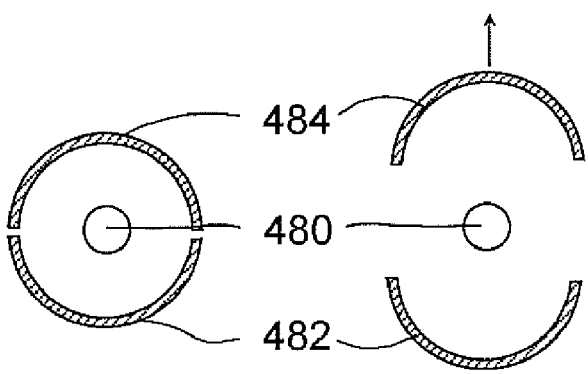 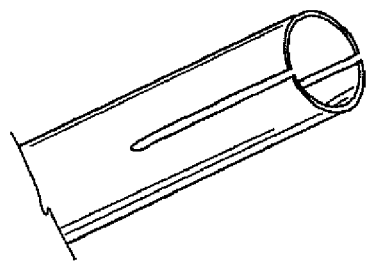
Fig. 4T　　　Fig. 4U　　　Fig. 4U'
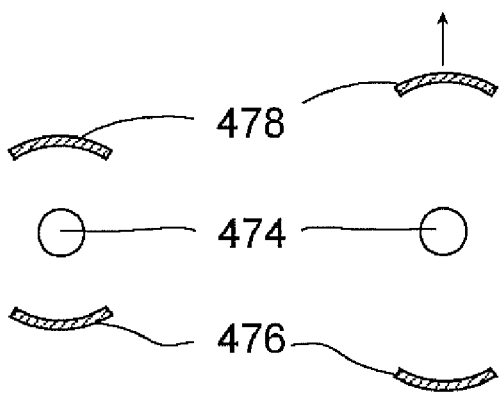 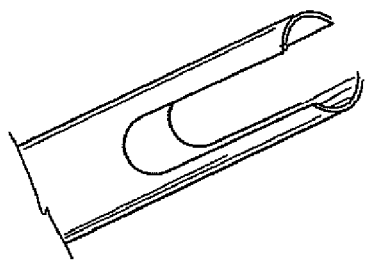
Fig. 4V　　　Fig. 4W　　　Fig. 4W'

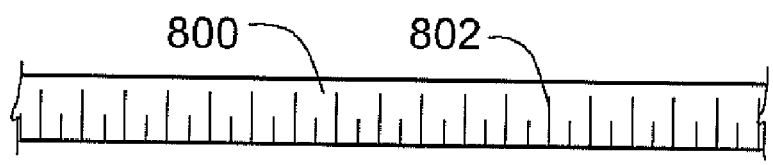
Fig. 8A
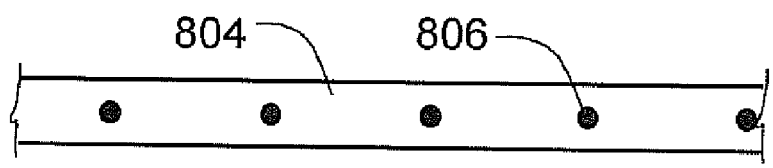
Fig. 8B
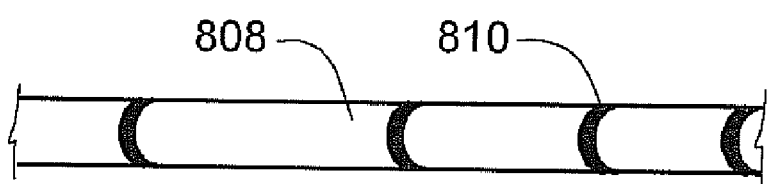
Fig. 8C
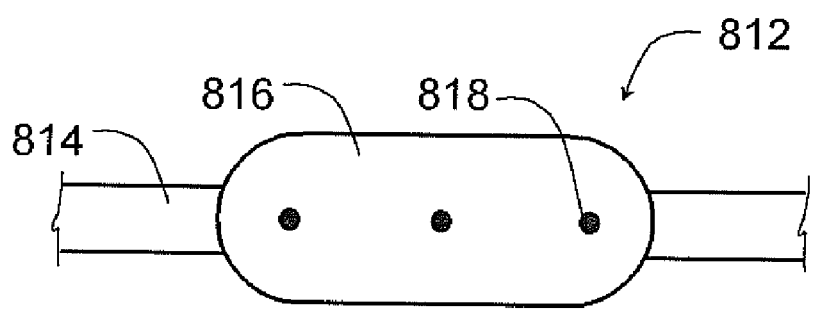
Fig. 8D
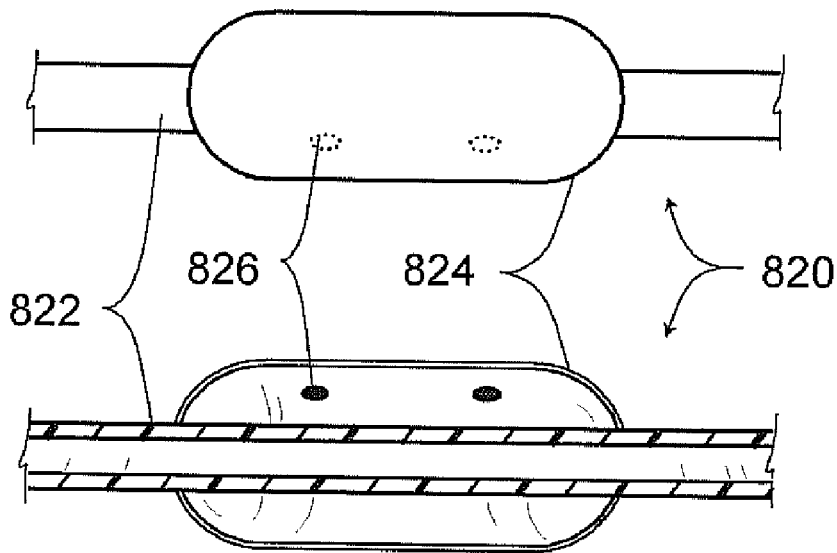
Fig. 8E
Fig. 8E'

DEVICES, SYSTEMS AND METHODS USEABLE FOR TREATING SINUSITIS

RELATED APPLICATION

This application is a continuation of copending U.S. patent application Ser. No. 11/150,847 entitled Devices, Systems and Methods Useable for Treating Sinusitus filed on Jun. 10, 2005 which is a continuation-in-part of copending U.S. patent application Ser. No. 10/944,270 entitled "Apparatus and Methods for Dilating and Modifying Ostia of Paranasal Sinuses and Other Intranasal or Paranasal Structures" filed on Sep. 17, 2004 which is a continuation-in-part of Ser. No. 10/829,917 entitled "Devices, Systems and Methods for Diagnosing and Treating Sinusitis and Other Disorders of the Ears, Nose and/or Throat" filed on Apr. 21, 2004, the entire disclosures of such earlier filed applications being expressly incorporated herein by reference.

FIELD OF THE INVENTION

The present invention relates generally to medical devices and methods and more particularly to minimally invasive, devices, systems and methods for treating sinusitis and other ear, nose & throat disorders.

BACKGROUND

The nose is responsible for warming, humidifying and filtering inspired air and for conserving heat and moisture from expired air. The nose is formed mainly of cartilage, bone, mucous membranes and skin.

The bones in the nose contain a series of cavities known as paranasal sinuses that are connected by passageways. The paranasal sinuses include frontal sinuses, ethmoid sinuses, sphenoid sinuses and maxillary sinuses. The paranasal sinuses are lined with mucous-producing epithelial tissue and ultimately opening into the nasal cavity. Normally, mucous produced by the epithelial tissue slowly drains out of each sinus through an opening known as an ostium. If the epithelial tissue of one of these passageways becomes inflamed for any reason, the cavities which drain through that passageway can become blocked. This blockage can be periodic (resulting in episodes of pain) or chronic. This interference with drainage of mucous (e.g., occlusion of a sinus ostium) can result in mucosal congestion within the paranasal sinuses. Chronic mucosal congestion of the sinuses can cause damage to the epithelium that lines the sinus with subsequent decreased oxygen tension and microbial growth (e.g., a sinus infection).

Sinusitis:

The term "sinusitis" refers generally to any inflammation or infection of the paranasal sinuses caused by bacteria, viruses, fungi (molds), allergies or combinations thereof. It has been estimated that chronic sinusitis (e.g., lasting more than 3 months or so) results in 18 million to 22 million physician office visits per year in the United States.

Patients who suffer from sinusitis typically experience at least some of the following symptoms:

headaches or facial pain
nasal congestion or post-nasal drainage
difficulty breathing through one or both nostrils
bad breath
pain in the upper teeth Thus, one of the ways to treat sinusitis is by restoring the lost mucous flow. The initial therapy is drug therapy using anti-inflammatory agents to reduce the inflammation and antibi-otics to treat the infection. A large number of patients do not respond to drug therapy. Currently, the gold standard for patients with chronic sinusitis that do not respond to drug therapy is a corrective surgery called Functional Endoscopic Sinus Surgery.

Current and Proposed Procedures for Sinus Treatment:

Functional Endoscooic Sinus Surgery

In FESS, an endoscope is inserted into the nose and, under visualization through the endoscope, the surgeon may remove diseased or hypertrophic tissue or bone and may enlarge the ostia of the sinuses to restore normal drainage of the sinuses. FESS procedures are typically performed with the patient under general anesthesia.

Although FESS continues to be the gold standard therapy for surgical treatment of severe sinus disease, FESS does have several shortcomings. For example, FESS can cause significant post-operative pain. Also, some FESS procedures are associated with significant postoperative bleeding and, as a result, nasal packing is frequently placed in the patient's nose for some period of time following the surgery. Such nasal packing can be uncomfortable and can interfere with normal breathing, eating, drinking etc. Also, some patients remain symptomatic even after multiple FESS surgeries. Additionally, some FESS procedures are associated with risks of iatrogenic orbital, intracranial and sinonasal injury. Many otolaryngologists consider FESS an option only for patients who suffer from severe sinus disease (e.g., those showing significant abnormalities under CT scan). Thus, patients with less severe disease may not be considered candidates for FESS and may be left with no option but drug therapy. One of the reasons why FESS procedures can be bloody and painful relates to the fact that instruments having straight, rigid shafts are used. In order to target deep areas of the anatomy with such straight rigid instrumentation, the physician needs to resect and remove or otherwise manipulate any anatomical structures that may lie in the direct path of the instruments, regardless of whether those anatomical structures are part of the pathology.

Balloon Dilation Based Sinus Treatment

Methods and devices for sinus intervention using dilating balloons have been disclosed in U.S. Pat. No. 2,525,183 (Robison) and United States Patent Publication No. 2004/0064150 A1 (Becker). For example, U.S. Pat. No. 2,525,183 (Robison) discloses an inflatable pressure device which can be inserted following sinus surgery and inflated within the sinus. The patent does not disclose device designs and methods for flexibly navigating through the complex nasal anatomy to access the natural ostia of the sinuses. The discussion of balloon materials is also fairly limited to thin flexible materials like rubber which are most likely to be inadequate for dilating the bony ostia of the sinus.

United States patent publication number 2004/0064150 A1 (Becker) discloses balloon catheters formed of a stiff hypotube to be pushed into a sinus. The balloon catheters have a stiff hypotube with a fixed pre-set angle that enables them to be pushed into the sinus. In at least some procedures wherein it is desired to position the balloon catheter in the ostium of a paranasal sinus, it is necessary to advance the balloon catheter through complicated or tortuous anatomy in order to properly position the balloon catheter within the desired sinus ostium. Also, there is a degree of individual variation in the intranasal and paranasal anatomy of human beings, thus making it difficult to design a stiff-shaft balloon catheter that is optimally shaped for use in all individuals. Indeed, rigid catheters formed of hypotubes that have pre-set angles cannot be easily adjusted by the physician to different shapes to account for individual variations in the anatomy. In view of this, the Becker patent application describes the necessity of having available a set of balloon catheters, each having a particular fixed angle so that the physician can select the appropriate catheter for the patient's anatomy. The requirement to test multiple disposable catheters for fit is likely to be very expensive and impractical. Moreover, if such catheter are disposable items (e.g., not sterilizable and reusable) the need to test and discard a number of catheters before finding one that has the ideal bend angle could be rather expensive.

Thus, although the prior art discloses the use of dilating balloons for sinus treatments, it does not disclose the various means for navigation through the complex anatomy without significant manipulation of non-pathogenic anatomical regions that obstruct direct access to the sinus openings. Further, the prior art only discloses balloons of relatively simple shapes or materials for dilating sinus openings. Further, this art does not sufficiently elaborate beyond endoscopy on other means for imaging or tracking the position of such devices within the sinus anatomy.

Thus, there is a need for new devices and methods for easily navigating the complex anatomy of the nasal cavities and paranasal sinuses and for treating disorders of the paranasal sinuses with minimal complications due to individual variations in anatomy and causing minimal trauma to or disruption of anatomical structures that are not pathogenic.

SUMMARY OF THE INVENTION

In general, the present invention provides methods, devices and systems for diagnosing and/or treating sinusitis or other conditions of the ear, nose or throat.

In accordance with the present invention, there are provided methods wherein one or more flexible or rigid elongate devices as described herein are inserted in to the nose, nasopharynx, paranasal sinus, middle ear or associated anatomical passageways to perform an interventional or surgical procedure. Examples of procedures that may be performed using these flexible catheters or other flexible elongate devices include but are not limited to: remodeling or changing the shape, size or configuration of a sinus ostium or other anatomical structure that affects drainage from one or more paranasal sinuses; cutting, ablating, debulking, cauterizing, heating, freezing, lasing, forming an osteotomy or trephination in or otherwise modifying bony or cartilaginous tissue within paranasal sinus or elsewhere within the nose; removing puss or aberrant matter from the paranasal sinus or elsewhere within the nose; scraping or otherwise removing cells that line the interior of a paranasal sinus; delivering contrast medium; delivering a therapeutically effective amount of a therapeutic substance; implanting a stent, tissue remodeling device, substance delivery implant or other therapeutic apparatus; cutting, ablating, debulking, cauterizing, heating, freezing, lasing, dilating or otherwise modifying tissue such as nasal polyps, abberant or enlarged tissue, abnormal tissue, etc.; grafting or implanting cells or tissue; reducing, setting, screwing, applying adhesive to, affixing, decompressing or otherwise treating a fracture; delivering a gene or gene therapy preparation; removing all or a portion of a tumor; removing a polyp; delivering histamine, an allergen or another substance that causes secretion of mucous by tissues within a paranasal sinus to permit assessment of drainage from the sinus; implanting a cochlear implant or indwelling hearing aid or amplification device, etc.

Still further in accordance with the invention, there are provided devices and systems for performing some or all of the procedures described herein. Introducing devices may be used to facilitate insertion of working devices (e.g. catheters e.g. balloon catheters, tissue cutting or remodeling devices, guidewires, devices for implanting elements like stents, electrosurgical devices, energy emitting devices, devices for delivering diagnostic or therapeutic agents, substance delivery implants, scopes etc) into the paranasal sinuses and other structures in the ear, nose or throat.

Still further in accordance with the invention, there are provided apparatus and methods for navigation and imaging of the interventional devices within the sinuses using endoscopic including stereo endoscopic, fluoroscopic, ultrasonic, radiofrequency localization, electromagnetic, magnetic and other radiative energy based modalities. These imaging and navigation technologies may also be referenced by computer directly or indirectly to pre-existing or simultaneously created 3-D or 2-D data sets which help the doctor place the devices within the appropriate region of the anatomy.

Still further in accordance with the invention, there are provided tubular guides, guidewires, balloon catheters, tubular sheaths and related methods for using such devices individually or in various combinations to dilate openings of paranasal sinuses (e.g., any transnasally accessible opening in a paranasal sinus or cranio-facial air cell, including but not limited to; natural ostia, surgically or medically altered ostia, surgically created or man made openings, antrostomy openings, ostiotomy openings, trephination openings, burr holes, drilled holes, ethmoidectomy openings, anatomical passageways, natural or man made passages, etc.) or other anatomical structures such as structures within the head or a human or animal subject that comprise bone covered at least in part by mucosal tissue.

Still further in accordance with the invention, there are provided specific methods and modes of construction for tubular guides, guidewires, balloon catheters, tubular sheaths.

Still further in accordance with the invention, there are provided methods for accessing (e.g., advancing a catheter, guide or other device to) openings of paranasal sinuses (e.g., any transnasally accessible opening in a paranasal sinus or cranio-facial air cell, including but not limited to; natural ostia, surgically or medically altered ostia, surgically created or man made openings, antrostomy openings, ostiotomy openings, trephination openings, burr holes, drilled holes, ethmoidectomy openings, anatomical passageways, natural or man made passages, etc.) or other anatomical structures within the body of a human or animal subject even though such openings or structures may be fully or partially hidden from direct or endoscopic view.

Further aspects, details and embodiments of the present invention will be understood by those of skill in the art upon reading the following detailed description of the invention and the accompanying drawings.

BRIEF DESCRIPTION OF THE DRAWINGS

FIGS. 2Y through 2AC are partial coronal sectional views through a human head showing various steps of a method for treating a mucocele in a frontal sinus.

FIGS. 4L and 4M show sectional views of a mechanical dilator that comprises a pushable member.

FIGS. 4N and 4O show sectional views of a mechanical dilator that comprises a pullable member.

FIGS. 4P and 4Q show sectional views of a mechanical dilator that comprises a hinged member.

FIGS. 4R through 4W' are schematic diagrams of alternative configurations for the distal portions of mechanical dilators of the types shown in FIGS. 4H through 4Q.

FIG. 5O shows a partial perspective view of a balloon catheter device comprising a balloon for delivering diagnostic or therapeutic substances.

FIG. 5P shows a partial perspective view of a balloon/cutter catheter device comprising a balloon with one or more cutter blades.

FIG. 5Q shows a perspective view of a balloon catheter device comprising a balloon with a reinforcing braid attached on the external surface of the balloon.

FIG. 5R shows a partial sectional view of a balloon catheter wherein inflation ports are located near the distal end of the balloon.

FIG. 5S shows a partial sectional view of an embodiment of a balloon catheter comprising multiple balloons inflated by a single lumen.

FIG. 5T shows a partial sectional view of a balloon catheter comprising multiple balloons inflated by multiple lumens.

FIGS. 5U through 5AB show perspective and sectional views of various embodiments of balloon catheters having sensors mounted thereon or therein.

FIG. 6F' is an enlarged side view of the braid of the device of FIG. 6F.

FIG. 8A shows a partial perspective view of a catheter shaft comprising distance markers.

FIG. 8B shows a partial perspective view of a catheter shaft comprising one type of radiopaque markers.

FIG. 8C shows a partial perspective view of a catheter shaft comprising another type of radiopaque markers.

FIG. 8D shows a partial perspective view of a balloon catheter comprising an array of radiopaque markers arranged on the outer surface of the balloon.

FIG. 8E shows a partial perspective view of a balloon catheter comprising an array of radiopaque markers arranged on an inner surface of the balloon.

FIG. 8E' is a longitudinal sectional view of FIG. 8E.

FIG. 10B' is an enlarged view of the distal end of the tubular guide device of FIG. 10B.

FIG. 10C' is an enlarged view of the distal end of the tubular guide device of FIG. 10C.

FIG. 10D' is an enlarged view of the distal end of the tubular guide device of FIG. 10D.

FIG. 10E' is an enlarged view of the distal end of the tubular guide device of FIG. 10E.

FIG. 11A is a cross sectional view through line 11A-11A of FIG. 11.

FIG. 11B is a cross sectional view through line 11B-11B of FIG. 11.

FIG. 11C is a cross sectional view through line 11C-11C of FIG. 11.

FIG. 11C' shows an enlarged view of region 11C' in FIG. 11C

FIG. 14A is a cross sectional view through line 14A-14A of FIG. 14.

FIG. 14B is a cross sectional view through line 14B-14B of FIG. 14.

FIG. 14C is an enlarged view of segment 14C of FIG. 14.

FIG. 14D is an enlarged view of segment 14D of FIG. 14.

FIG. 14E is a cross sectional view through line 14E-14E of FIG. 14C.

DETAILED DESCRIPTION

The following detailed description, the accompanying drawings and the above-set-forth Brief Description of the Drawings are intended to describe some, but not necessarily all, examples or embodiments of the invention. The contents of this detailed description do not limit the scope of the invention in any way.

A number of the drawings in this patent application show anatomical structures of the ear, nose and throat. In general, these anatomical structures are labeled with the following reference letters:

| | |
|---|---|
| Nasal Cavity | NC |
| Nasopharynx | NP |
| Frontal Sinus | FS |
| Ethmoid Sinus | ES |
| Ethmoid Air Cells | EAC |
| Sphenoid Sinus | SS |
| Sphenoid Sinus Ostium | SSO |
| Maxillary Sinus | MS |
| Mucocele | MC |

Figure 1:
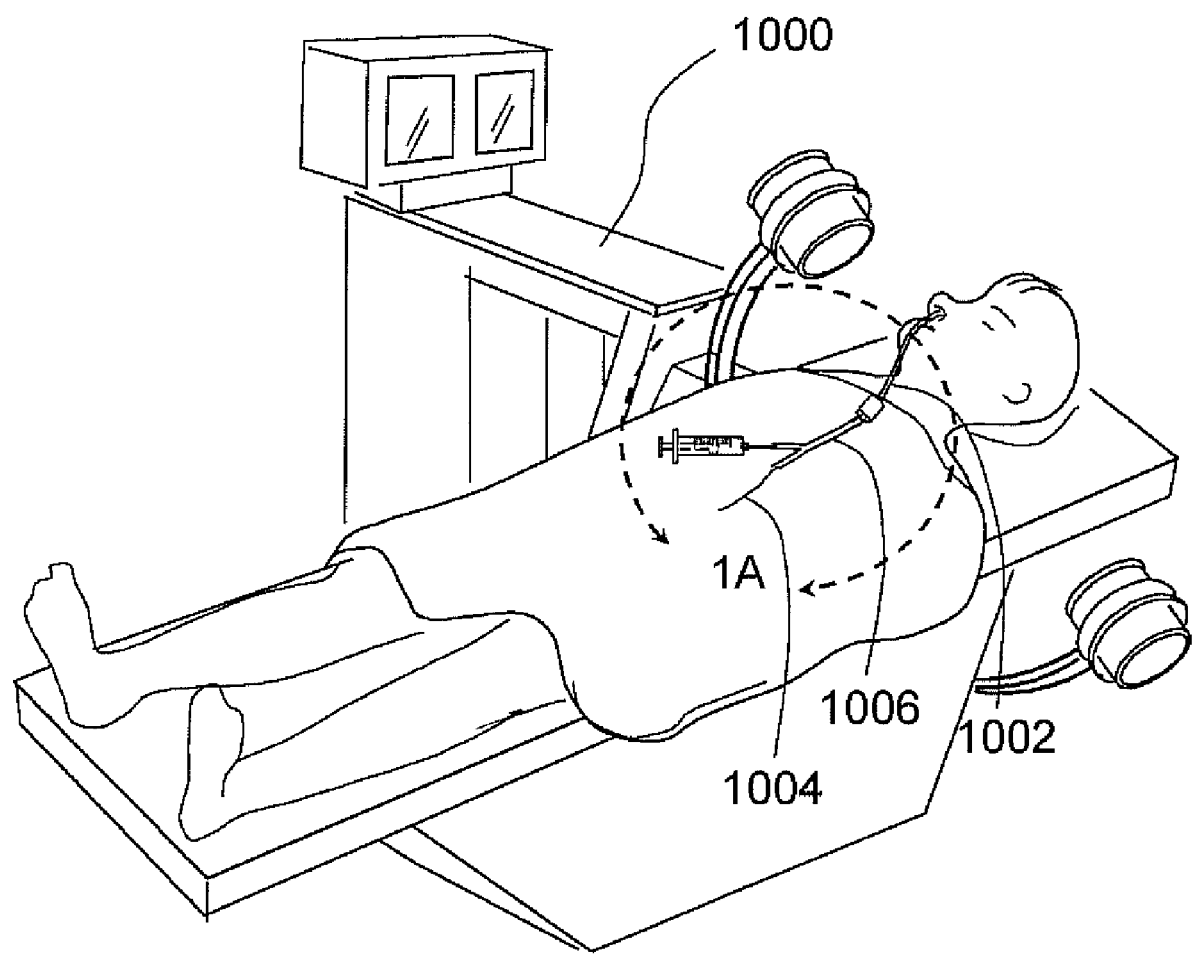
FIG. 1 shows a schematic diagram of a system for catheter-based minimally invasive sinus surgery of the present invention being used to perform a sinus surgery procedure on a human patient.
Figure 1A:
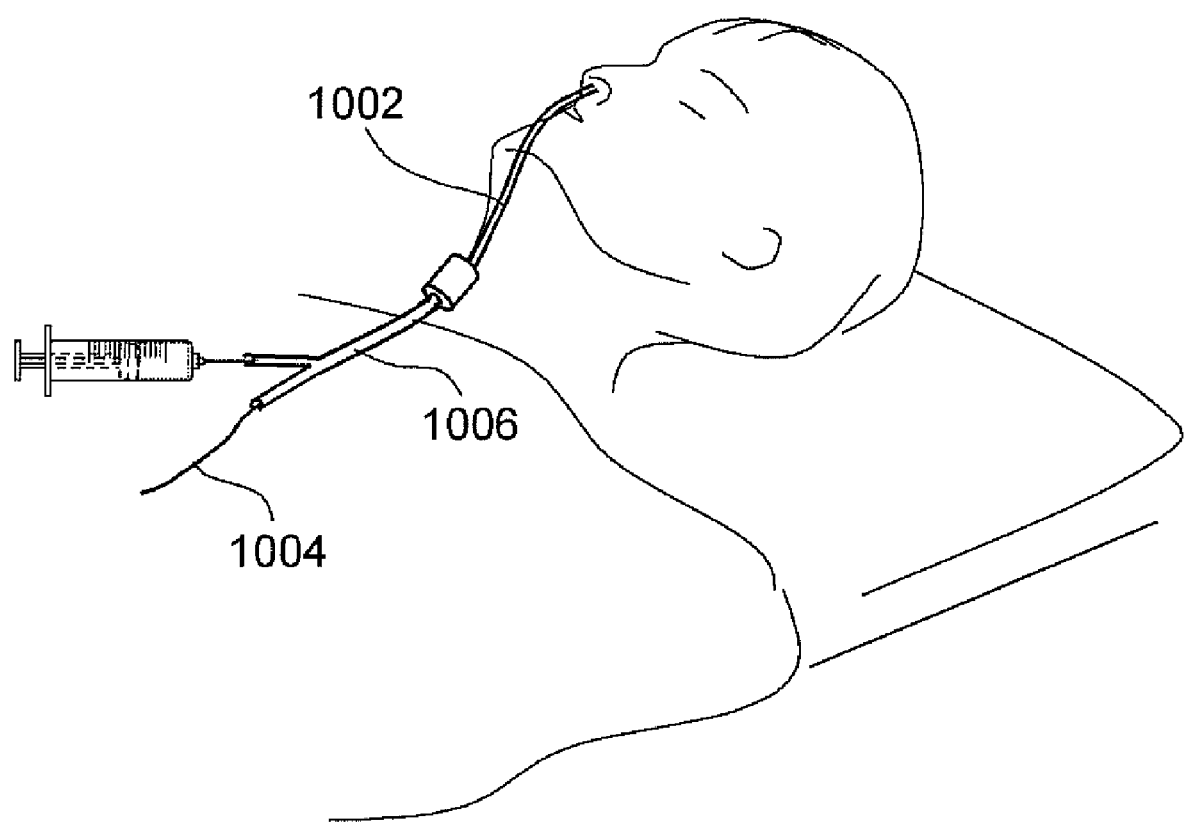
FIG. 1A is an enlarged view of portion "1A" of FIG. 1.

FIGS. 1 and 1A provide a general showing of a minimally invasive surgery system of the present invention comprising a C-arm fluoroscope 1000 that is useable to visualize a first introducing device 1002 (e.g., a guide catheter or guide tube), a second introducing device 1004 (e.g., a guidewire or elongate probe) and a working device 1006 (e.g., a balloon catheter, other dilation catheter, debrider, cutter, etc.). FIGS. 2A-8E' show certain non-limiting examples of the introducing devices 1002 (e.g., a guide catheter or guide tube), 1004 (guides, guidewires, elongate probes, etc.) and working devices 1006 (e.g., a balloon catheters, other dilation catheters, debrider, cutters, etc.) that may be useable in accordance with this invention. The devices 1002, 1004, 1006 may be radiopaque and/or may incorporate radiopaque markers such that C-arm fluoroscope 1000 may be used to image and monitor the positioning of the devices 1002, 1004, 1006 during the procedure. In addition to or, as an alternative to the use of radiographic imaging, the devices 1002, 1004, 1006 may incorporate and/or may be used in conjunction with one or more endoscopic devices, such as the typical rigid or flexible endoscopes or stereo endocscopes used by otolaryngologists during FESS procedures. Also, in addition to or as an alternative to radiographic imaging and/or endoscopic visualizations, some embodiments of the devices 1002, 1004, 1006 may incorporate sensors which enable the devices 1002, 1004, 1006 to be used in conjunction with image guided surgery systems or other electro-anatomical mapping/guidance systems including but not limited to: VectorVision (BrainLAB AG); HipNav (CASurgica); CBYON Suite (CBYON); InstaTrak, FluoroTrak, ENTrak (GE Medical); StealthStation Treon, iOn (Medtronic); Medivision; Navitrack (Orthosoft); OTS (Radionics); VISLAN (Siemens); Stryker Navigation System (Stryker Leibinger); Voyager, Z-Box (Z-Kat Inc.) and NOGA and CARTO systems (Johnson & Johnson). Commercially available interventional navigation systems can also be used in conjunction with the devices and methods. Further non-fluoroscopic interventional imaging technologies including but not limited to: OrthoPilot (B. Braun Aesculap); PoleStar (Odin Medical Technologies; marketed by Medtronic); SonoDoppler, SonoWand (MISON); CT Guide, US Guide (UltraGuide) etc. may also be used in conjunction with the devices and methods. Guidance under magnetic resonance is also feasible if the catheter is modified to interact with the system appropriately.

It is to be appreciated that the devices and methods of the present invention relate to the accessing and dilation or modification of sinus ostia or other passageways within the ear nose and throat. These devices and methods may be used alone or may be used in conjunction with other surgical or non-surgical treatments, including but not limited to the delivery or implantation of devices and drugs or other substances as described in copending U.S. patent application Ser. No. 10/912,578 entitled Implantable Devices and Methods for Delivering Drugs and Other Substances to Treat Sinusitis and Other Disorders filed on Aug. 4, 2004, the entire disclosure of which is expressly incorporated herein by reference.

Figure 2A:
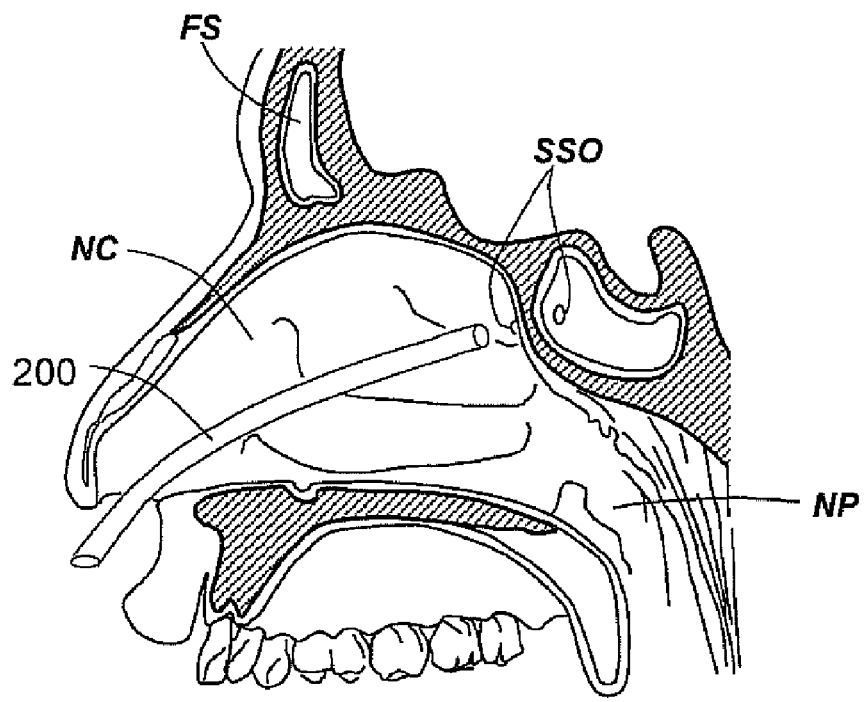
FIGS. 2A through 2D are partial sagittal sectional views through a human head showing various steps of a method for gaining access to a paranasal sinus using a guide and thereafter dilating or remodeling the ostial opening into the paranasal sinus.
Figure 2B:
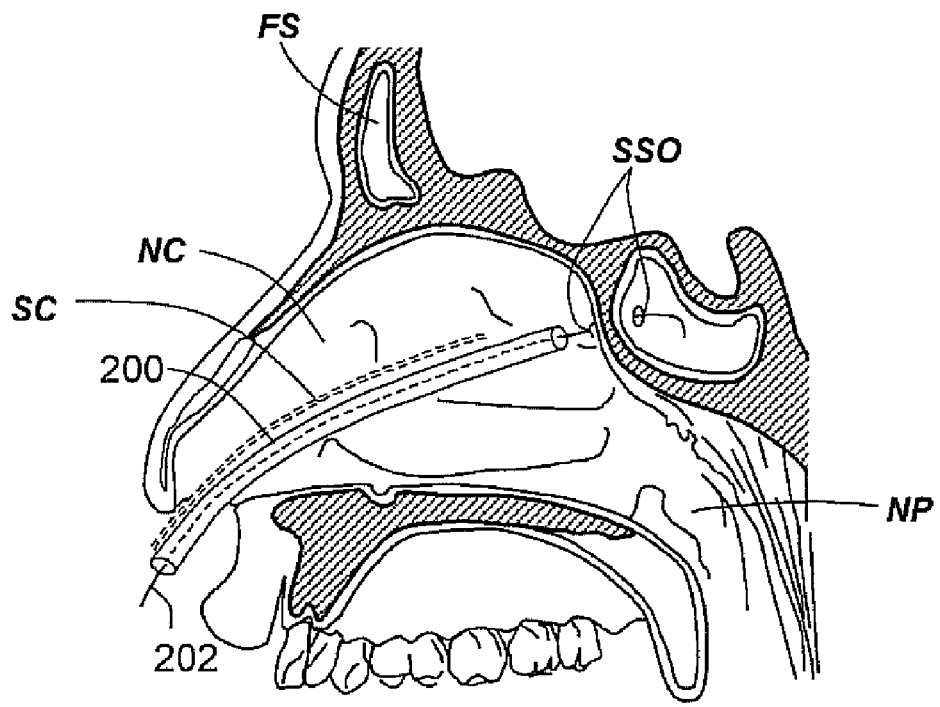
Figure 2C:
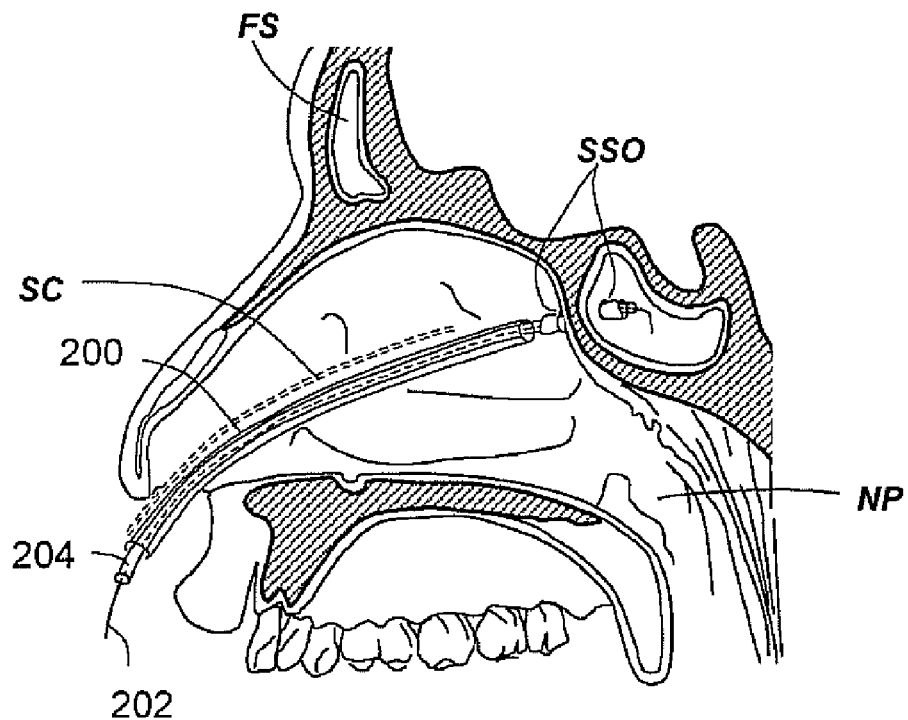
Figure 2D:
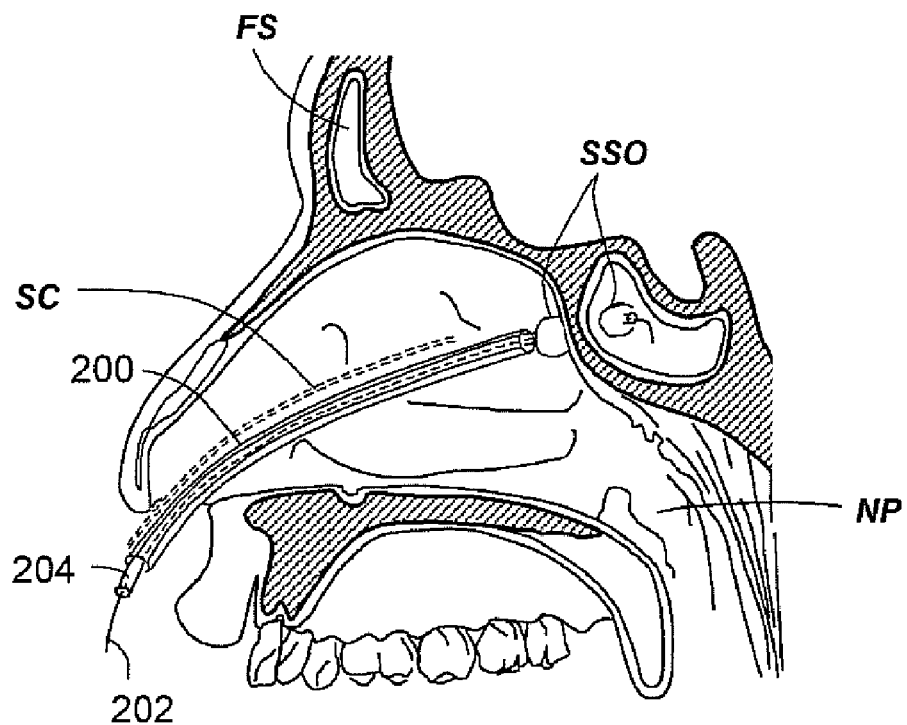

FIGS. 2A through 2D are partial sagittal sectional views through a human head showing various steps of a method of gaining access to a paranasal sinus using a guide catheter. In FIG. 2A, a first introducing device in the form of a guide catheter 200 is introduced through a nostril and through a nasal cavity NC to a location close to an ostium SSO of a sphenoid sinus SS. The guide catheter 200 may be flexible. Flexible devices are defined as devices with a flexural stiffness less than about 200 pound-force per inch over a device length of one inch. The guide catheter 200 may be straight or it may incorporate one or more preformed curves or bends. In embodiments where the guide catheter 200 is curved or bent, the deflection angle of the curve or bend may be in the range of up to 135°. Examples of specific deflection angles formed by the curved or bent regions of the guide catheter 200 are 0°, 30°, 45°, 60°, 70°, 90°, 120° and 135°. Guide catheter 200 can be constructed from suitable elements like Pebax, Polyimide, Braided Polyimide, Polyurethane, Nylon, PVC, Hytrel, HDPE, PEEK, metals like stainless steel and fluoropolymers like PTFE, PFA, FEP and EPTFE. Guide catheter 200 can have a variety of surface coatings e.g. hydrophilic lubricious coatings, hydrophobic lubricious coatings, abrasion resisting coatings, puncture resisting coatings, electrically or thermal conductive coatings, radiopaque coatings, echogenic coatings, thrombogenicity reducing coatings and coatings that release drugs. In FIG. 2B, a second introduction device comprising a guidewire 202 is introduced through the first introduction device (i.e., the guide catheter 200) so that the guidewire 202 enters the sphenoid sinus SS through the ostium SSO. Guidewire 202 may be constructed and coated as is common in the art of cardiology. In FIG. 2C, a working device 204 for example a balloon catheter is introduced over guidewire 202 into the sphenoid sinus SS. Thereafter, in FIG. 2D, the working device 204 is used to perform a diagnostic or therapeutic procedure. In this particular example, the procedure is dilation of the sphenoid sinus ostium SSO, as is evident from FIG. 2D. However, it will be appreciated that the present invention may also be used to dilate or modify any sinus ostium or other man-made or naturally occurring anatomical opening or passageway within the nose, paranasal sinuses, nasopharynx or adjacent areas. After the completion of the procedure, guide catheter 200, guidewire 202 and working device 204 are withdrawn and removed. As will be appreciated by those of skill in the art, in this or any of the procedures described in this patent application, the operator may additionally advance other types of catheters or of the present invention, a guidewire 202 may be steerable (e.g. torquable, actively deformable) or shapeable or malleable. Guidewire 202 may comprise an embedded endoscope or other navigation or imaging modalities including but not limited to fluoroscopic, X-ray radiographic, ultrasonic, radiofrequency localization, electromagnetic, magnetic, robotic and other radiative energy based modalities. In this regard, some of the figures show optional scopes SC is dotted lines. It is to be appreciated that such optional scopes SC may comprise any suitable types of rigid or flexible endoscopes and such optional scopes SC may be separate from or incorporated into the working devices and/or introduction devices of the present invention.

Figure 2E:
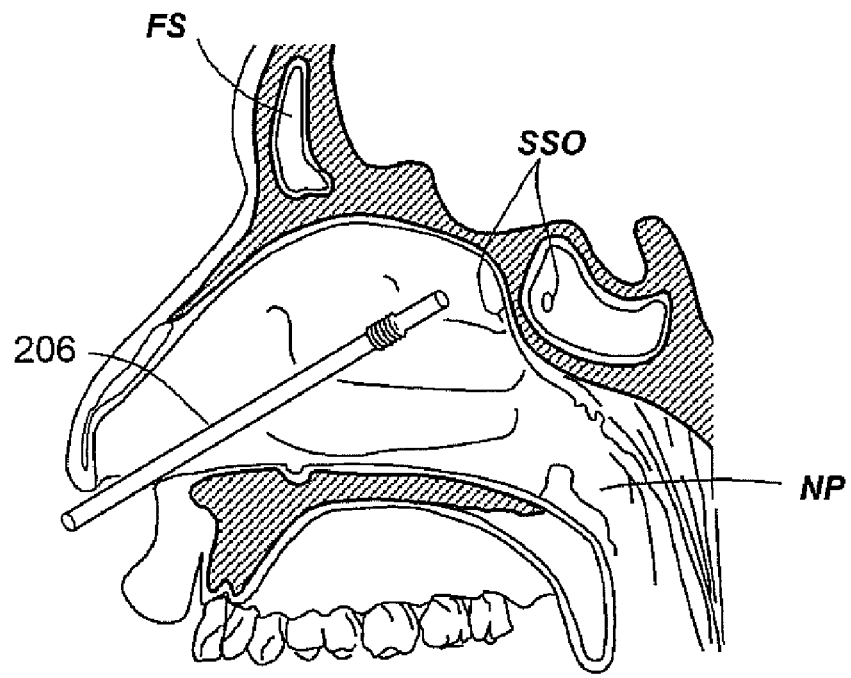
FIGS. 2E through 2H are partial sagittal sectional views through a human head showing various steps of a method for gaining access to a paranasal sinus using a steerable guide and thereafter.
Figure 2F:
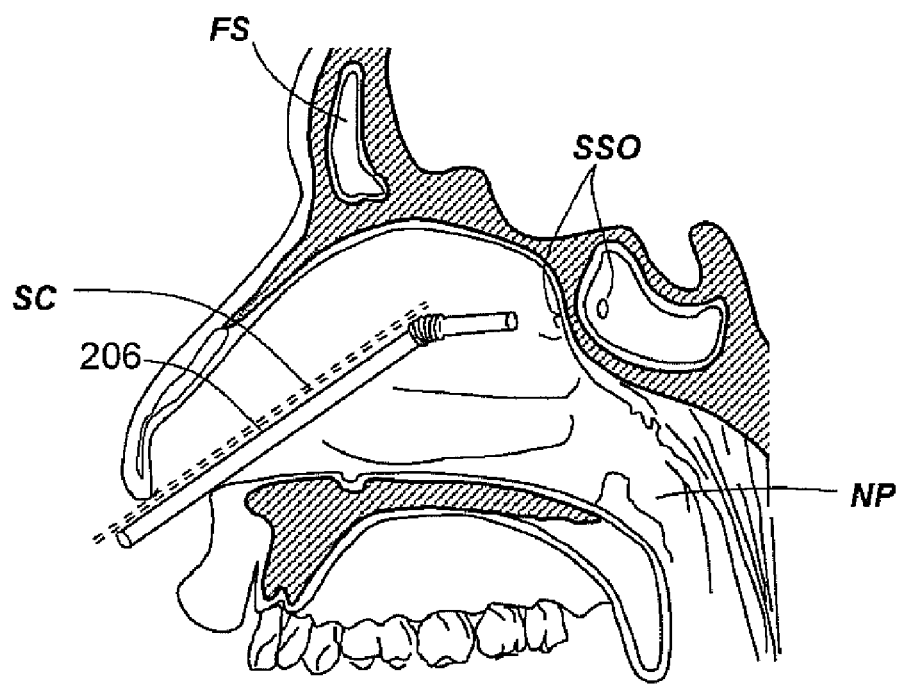
Figure 2G:
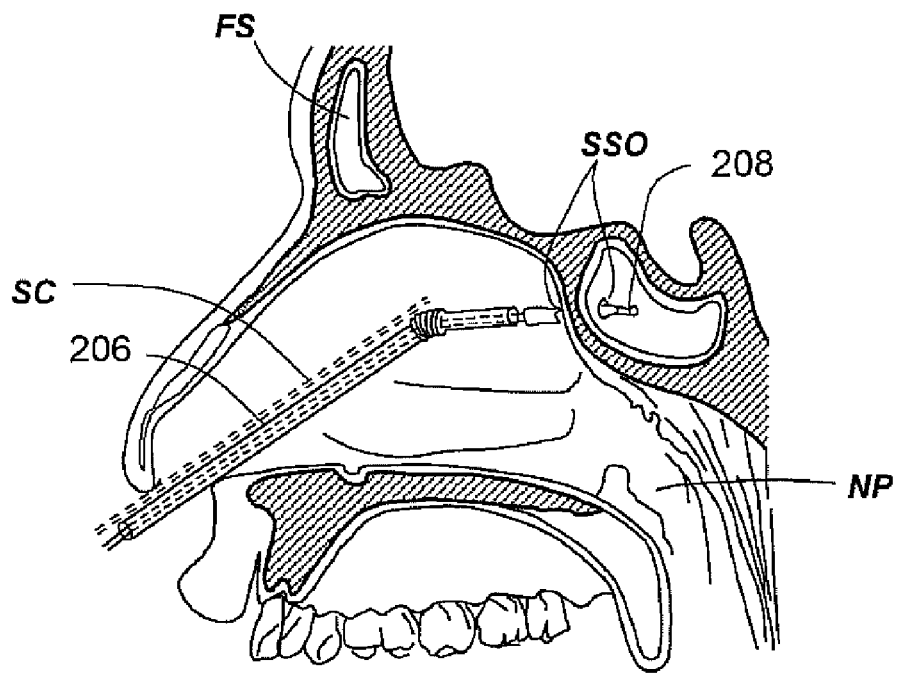
Figure 2H:
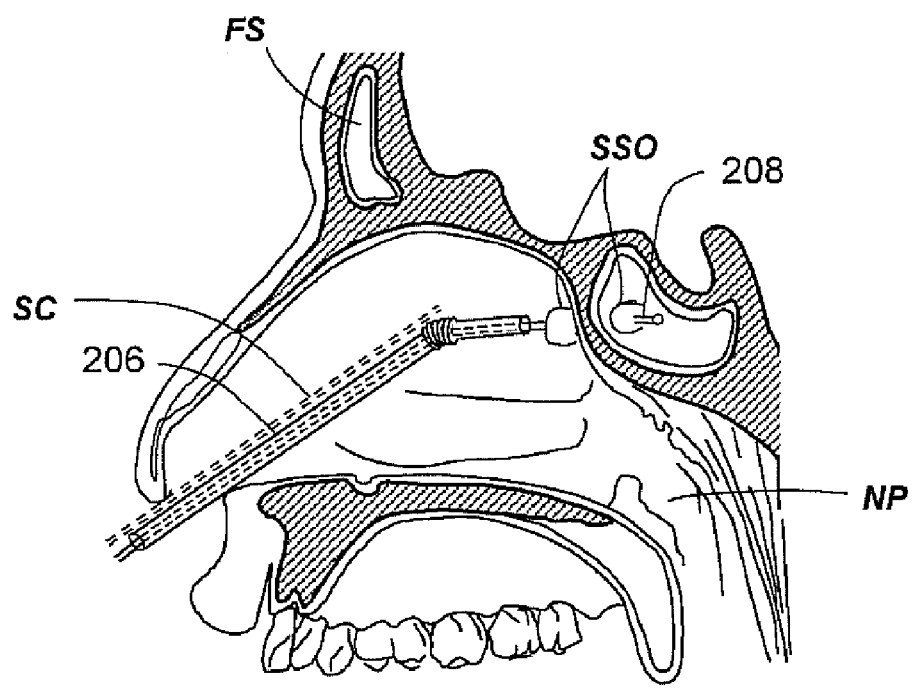

FIGS. 2E through 2H are partial sagittal sectional views through a human head showing various steps of a method of gaining access to a paranasal sinus using a steerable catheter. In FIG. 2E, an introducing device in the form of a steerable catheter 206 is introduced through a nostril. Although commercially available devices are neither designed, nor easily usable for this technique in the sinuses, examples of a device which has a steerable tip with functionality similar to that described here include but are not limited to the Naviport™ manufactured by Cardima, Inc. in Fremont, Calif.; Attain Prevail and Attain Deflectable catheters manufactured by Medtronic; Livewire Steerable Catheters manufactured by St. Jude Medical Inc.; Inquiry™ Steerable Diagnostic Catheters manufactured by Boston Scientific; TargetCath™ manufactured by EBI; Safe-Steer Catheter manufactured by Intraluminal Therapeutics, Inc.; Cynosar manufactured by Catheter Research, Inc.; Torque Control Balloon Catheter manufactured by Cordis Corp. and DynamicDeca Steerable Catheter and Dynamic XT Steerable Catheter manufactured by A.M.I. Technologies Ltd, Israel. Steerable catheter 206 comprises a proximal portion, a distal portion and a controllably deformable region between the proximal portion and the distal portion. In FIG. 2F, the steerable catheter 206 is steered through the nasal anatomy so that the distal portion of steerable catheter 206 is near an ostium SSO of a sphenoid sinus SS. In FIG. 2G, a working device in the form of a balloon catheter 208 is introduced through steerable catheter 206 so that it enters sphenoid sinus SS through the ostium SSO. Thereafter, balloon catheter 208 is adjusted so that the balloon of the balloon catheter is located in the ostium SSO. In FIG. 2H, balloon catheter 208 is used to dilate the ostium SSO. After completion of the procedure, steerable catheter 206 and balloon catheter 208 are withdrawn from the nasal anatomy. In this example, only a first introduction device in the form of a steerable catheter 206 is used to effect insertion and operative positioning of the working device (which in this example is balloon catheter 208). It will be appreciated, however, in some procedures, a second introduction device (e.g., an elongate guide member, guidewire, elongate probe, etc.) could be advanced through the lumen of the steerable catheter 206 and the working device 208 could then be advanced over such second introduction device to the desired operative location.

Figure 2I:
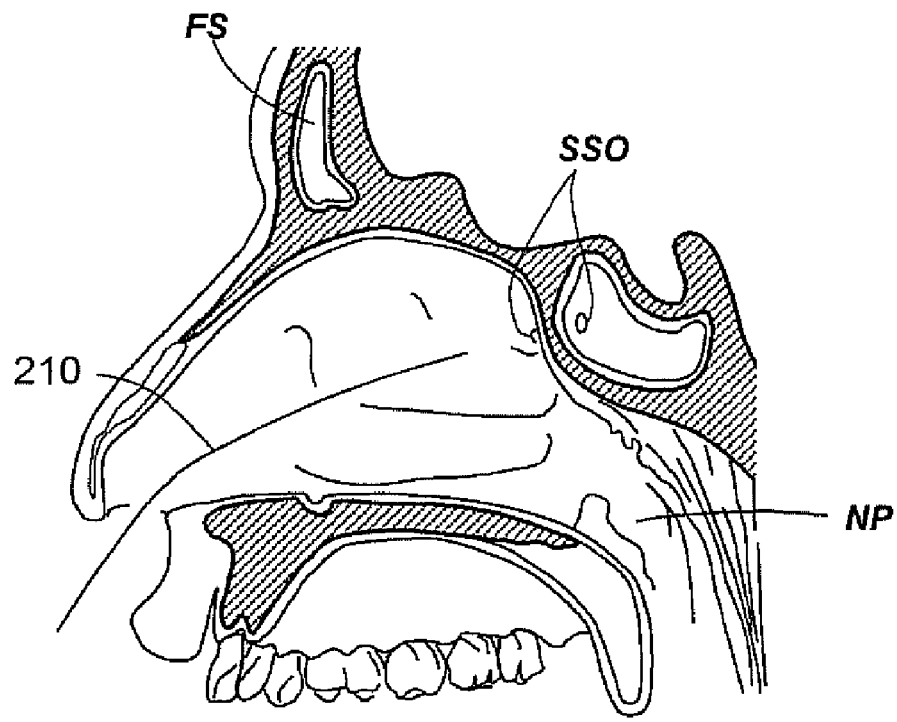
FIGS. 2I through 2L are partial sagittal sectional views through a human head showing various steps of a method for gaining access to a paranasal sinus using an introducing device in the form of a guidewire with a preset shape.
Figure 2J:
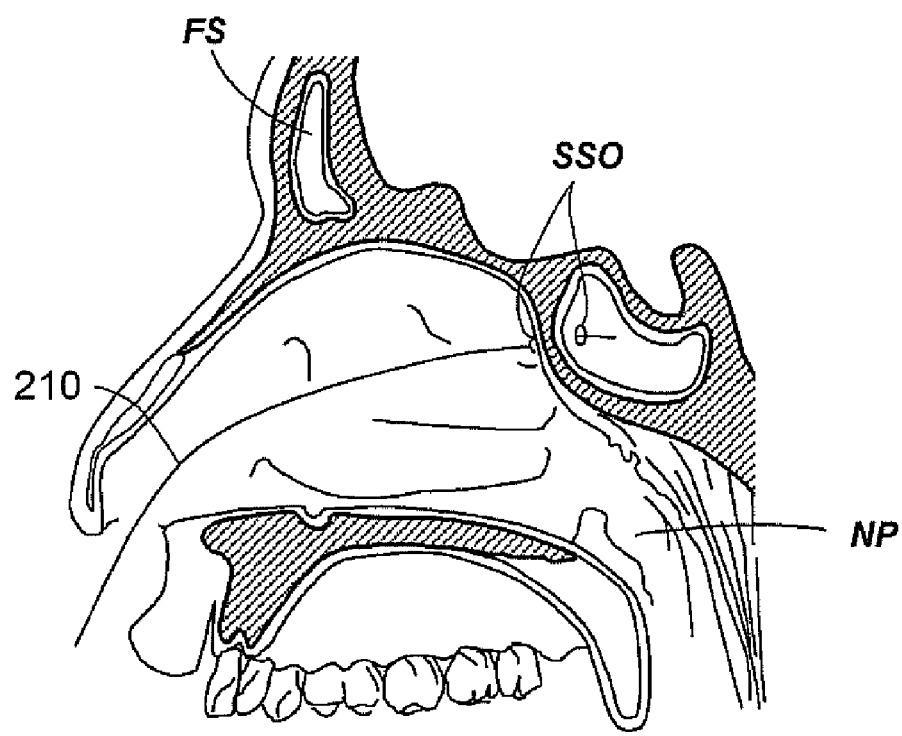
Figure 2K:
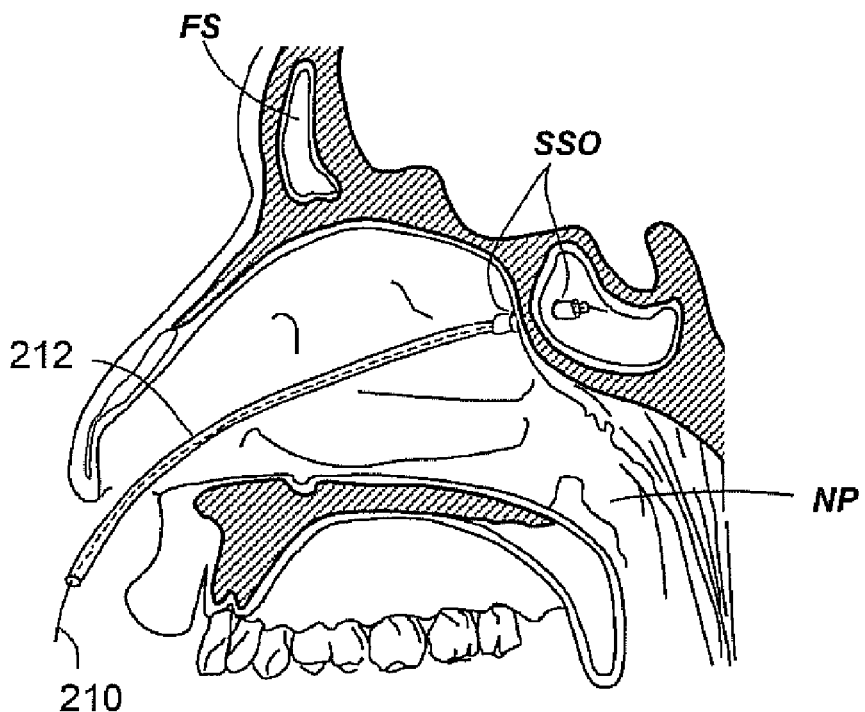
Figure 2L:
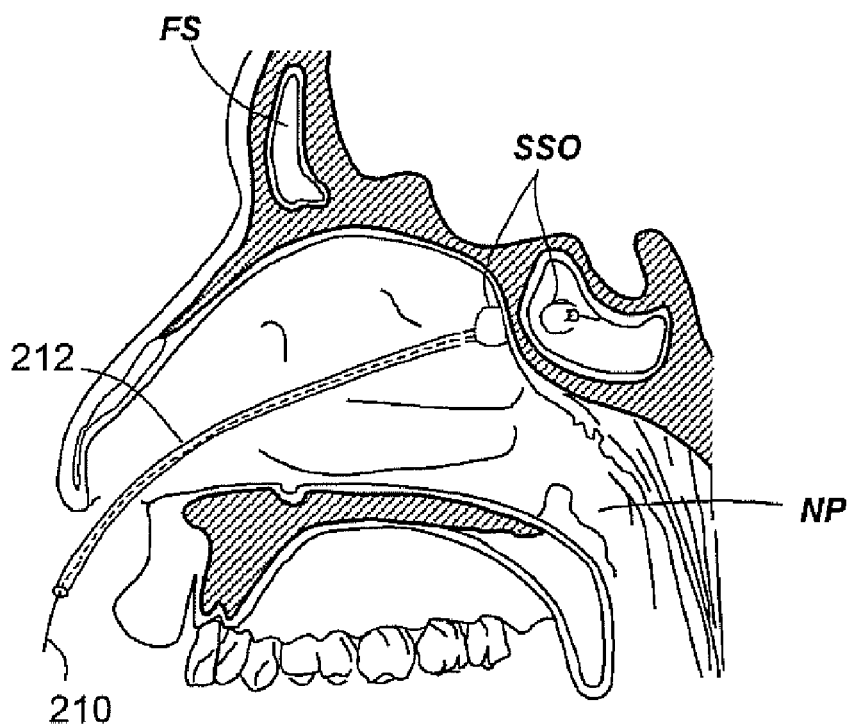

FIGS. 2I through 2L are partial sagittal sectional views through a human head showing various steps of a method for gaining access to a paranasal sinus using an introducing device in the form of a guidewire with a preset shape. In FIG. 2I, an introducing device in the form of a guidewire 210 with a preset shape is introduced in a nasal cavity. Guidewire 210 comprises a proximal portion and a distal portion and is shaped such that it can easily navigate through the nasal anatomy. In one embodiment, guidewire 210 is substantially straight. In another embodiment, guidewire 210 comprises an angled, curved or bent region between the proximal portion and the distal portion. Examples of the deflection angle of the angled, curved or bent regions are 0°, 30°, 45°, 60°, 70°, 90°, 120° and 135°. In FIG. 2J, guidewire 210 is advanced through the nasal anatomy so that the distal tip of guidewire enters a sphenoid sinus SS through an ostium SSO. In FIG. 2K, a working device in the form of a balloon catheter 212 is advanced along guidewire 210 into the sphenoid sinus SS. Typically, as described more fully herebelow, the working device will have a guidewire lumen extending through or formed in or on at least a portion of the working device 212 to facilitate advancement of the working device 212 over the guidewire 212 in the manner well understood in the art of interventional medicine. Thereafter, the position of balloon catheter 212 is adjusted so that the balloon of the balloon catheter is located in the ostium SSO. As described elsewhere in this application, the balloon catheter 212 may be radiopaque and/or may incorporate one or more visible or imageable markers or sensors. In FIG. 2L, balloon catheter 212 is used to dilate the ostium SSO. After completion of the procedure, guidewire 210 and balloon catheter 212 are withdrawn from the nasal anatomy. In one embodiment, balloon catheter 212 is shapeable or malleable.

Figure 2M:
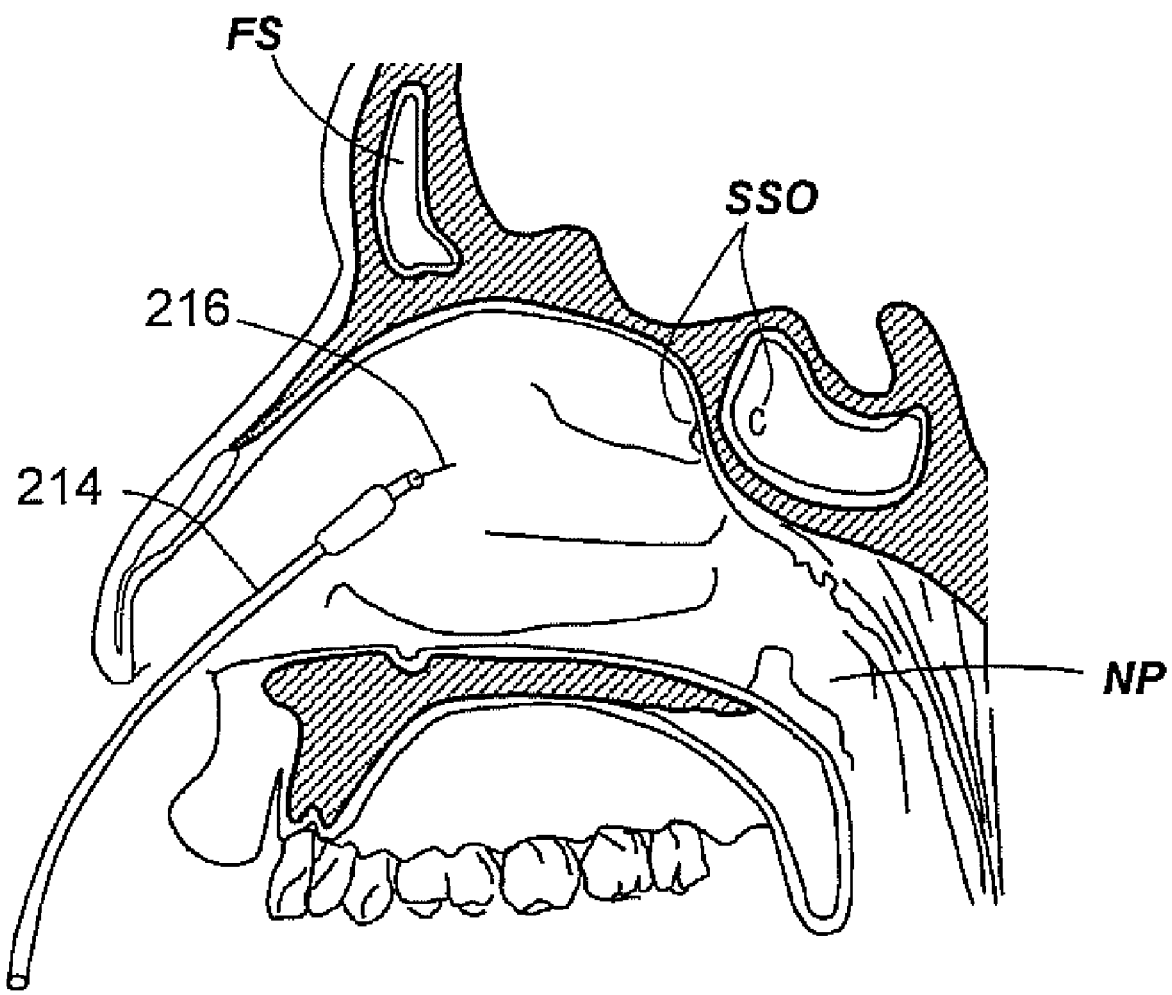
FIGS. 2M through 2O are partial sagittal sectional views through a human head showing various steps of a method for gaining access to a paranasal sinus using a balloon catheter that has a guide protruding from its distal end.
Figure 2N:
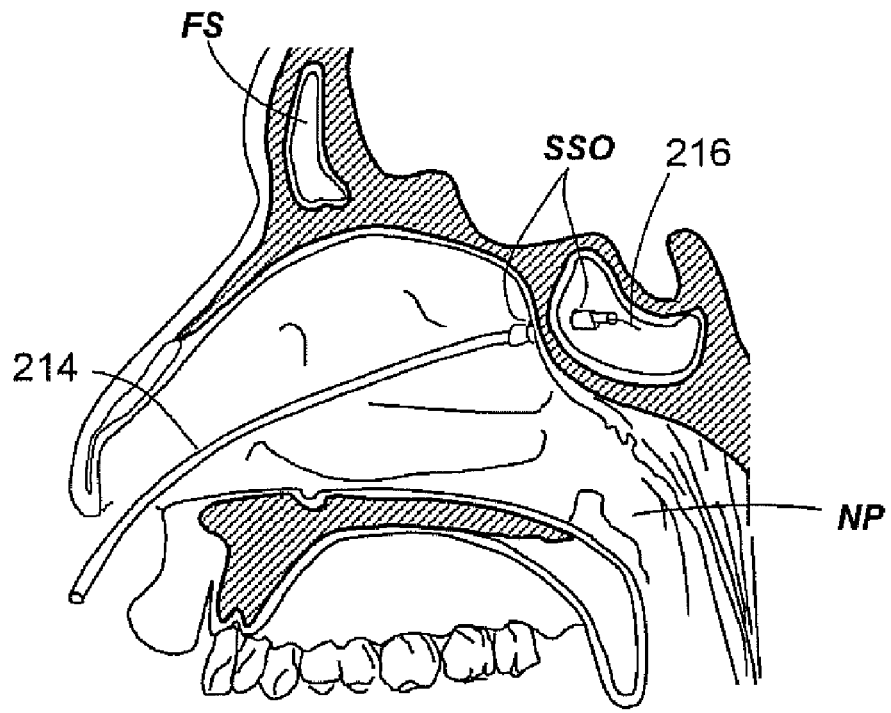
Figure 2O:
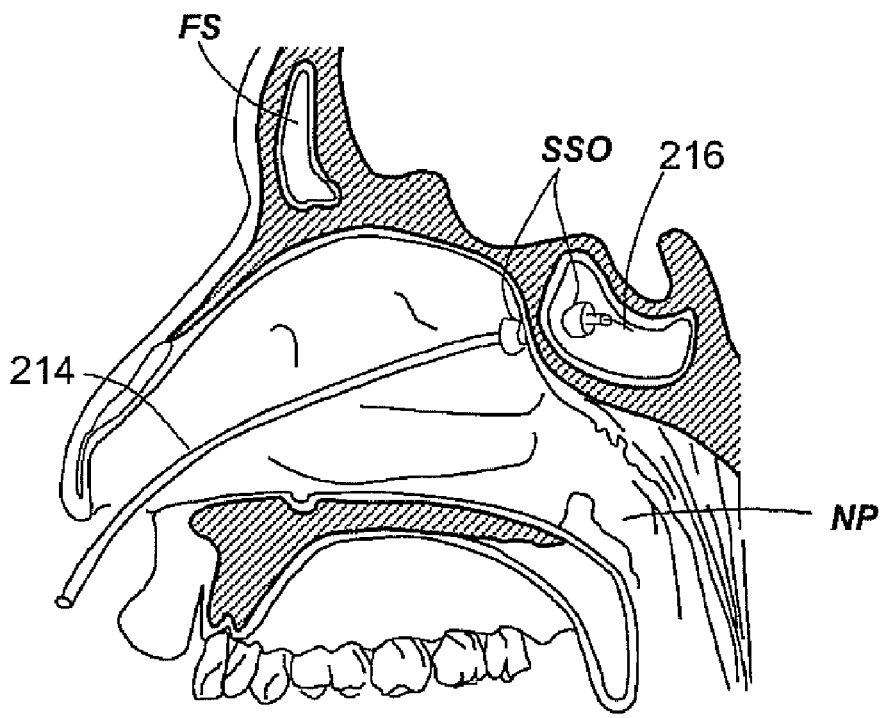

FIGS. 2M through 2O are partial sagittal sectional views through a human head showing various steps of a method of gaining access to a paranasal sinus using a balloon catheter comprising a steering wire at its distal end. In FIG. 2M, a working device comprising a balloon catheter 214 comprising a proximal portion and distal portion is introduced in a nasal cavity. Balloon catheter 214 comprises a steering wire 216 at its distal end. In FIG. 2N, balloon catheter 214 is advanced through the nasal anatomy into a sphenoid sinus SS through a sphenoid sinus ostium SSO. Thereafter, the position of balloon catheter 214 is adjusted so that the balloon of the balloon catheter is located in the ostium SSO. In FIG. 2O, balloon catheter 214 is used to dilate the ostium SSO. After completion of the procedure, balloon catheter 214 is withdrawn from the nasal anatomy. In one embodiment, steering wire 216 can be retracted into or advanced from balloon catheter 214. The retraction or advancement of steering wire can be controlled by several means like a thumb wheel, a slide, a button hooked up to electronic motor and a trigger. In another embodiment, steering wire 216 may be hollow or may incorporate one or more lumen(s) to enable it to introduce or remove devices or diagnostic or therapeutic agents, examples of which are described in copending U.S. patent application Ser. No. 10/912,578 entitled Implantable Devices and Methods for Delivering Drugs and Other Substances to Treat Sinusitis and Other Disorders filed on Aug. 4, 2004, the entire disclosure of which is expressly incorporated herein by reference.

Figure 2P:
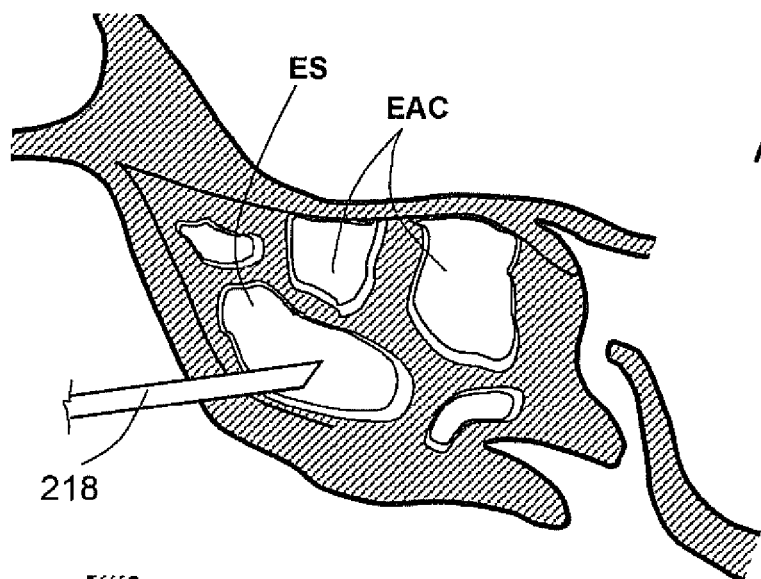
FIGS. 2P through 2X are partial sagittal sectional views through a human head showing various steps of a method of accessing an ethmoid sinus through a natural or artificially created opening of the ethmoid sinus.
Figure 2Q:
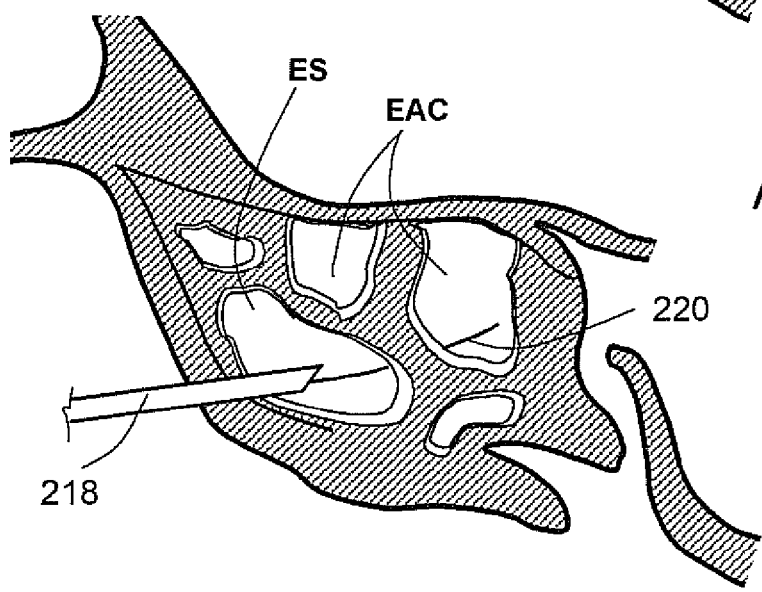
Figure 2R:
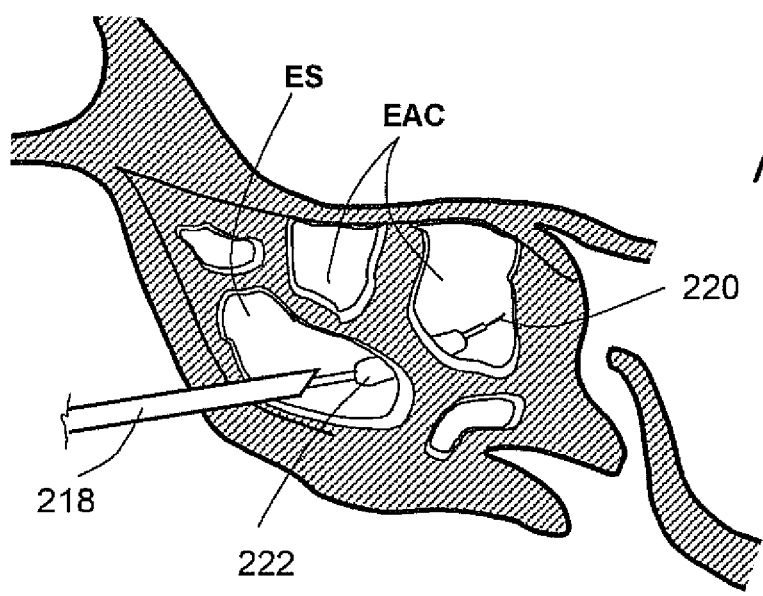
Figure 2S:
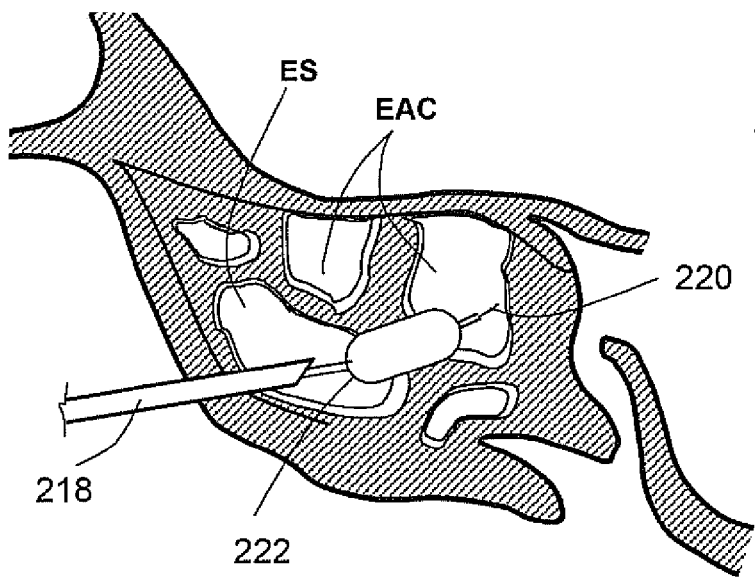
Figure 2T:
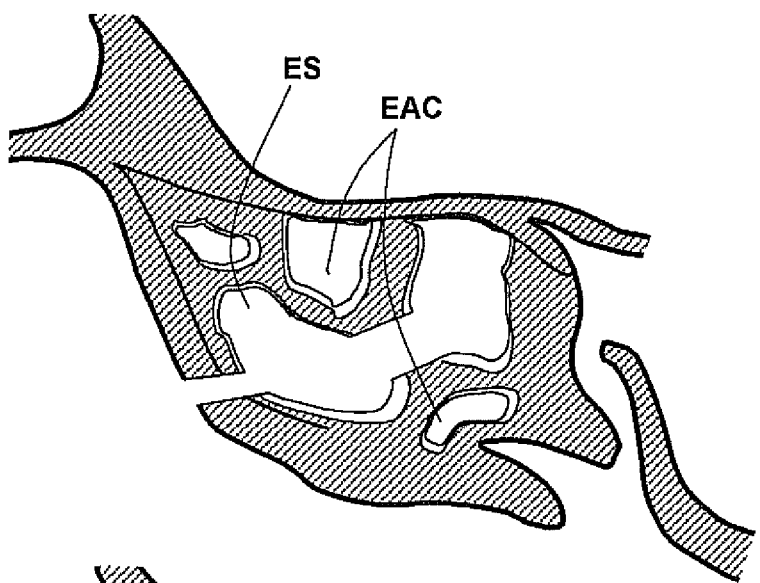
Figure 2U:
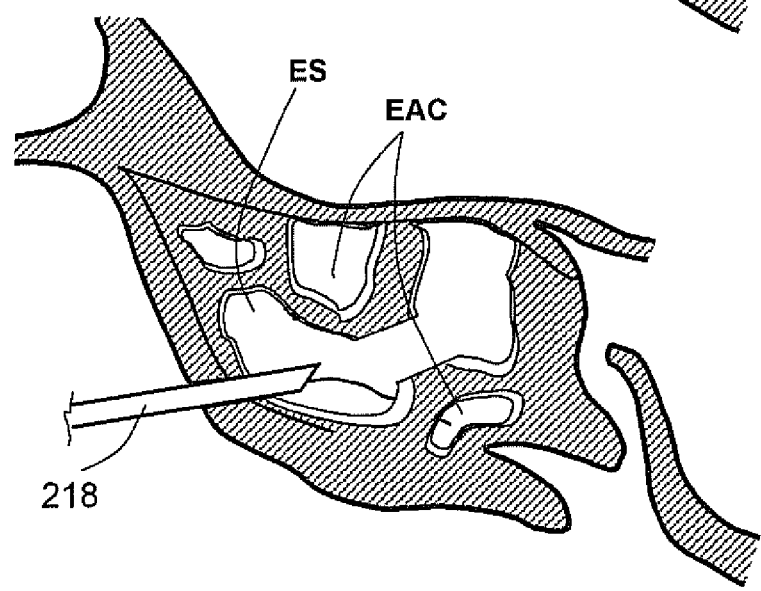
Figure 2V:
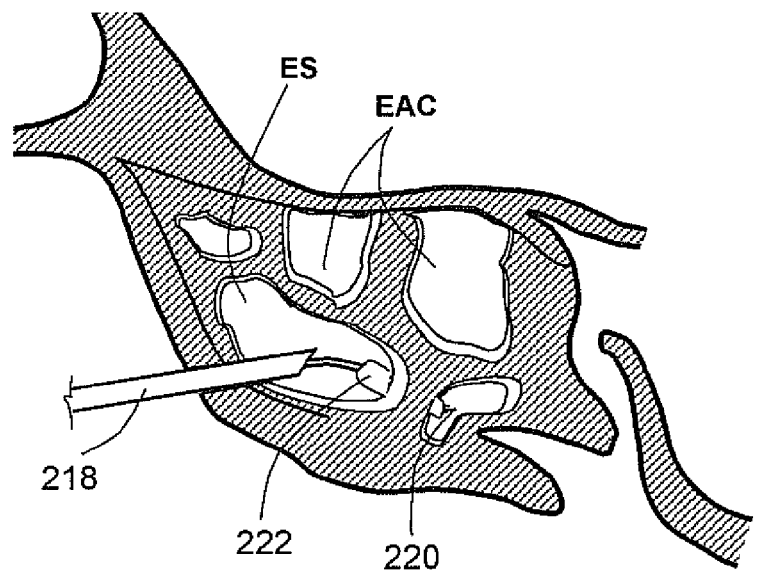
Figure 2W:
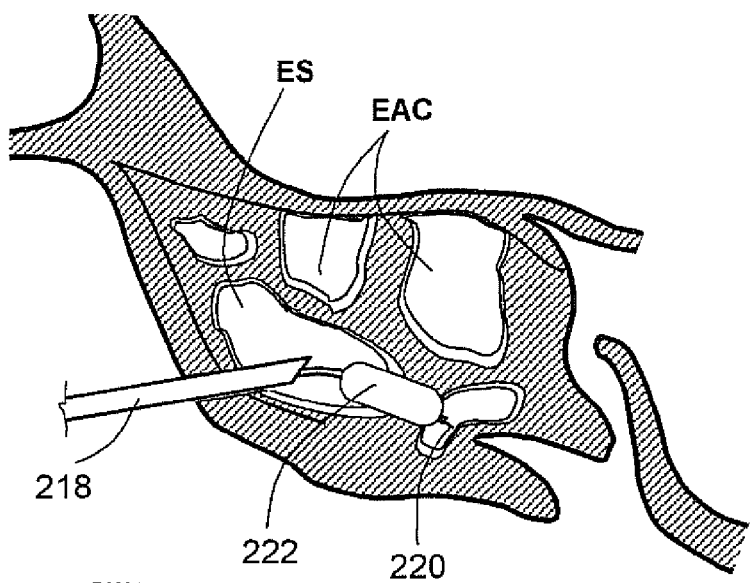
Figure 2X:
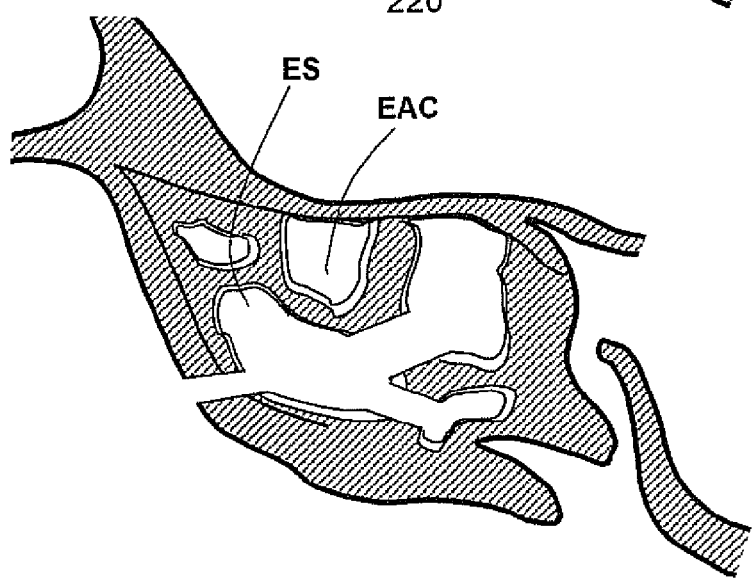

FIGS. 2P through 2X are partial sagittal sectional views through a human head showing various steps of a method for accessing an ethmoid sinus through a natural or artificially created opening of the ethmoid sinus. In FIG. 2P, an introducing device in the form of a guide catheter 218 is introduced in an ethmoid sinus ES. Ethmoid sinus ES comprises multiple ethmoid air cells EAC. In FIG. 2Q, a guidewire 220 is introduced through guide catheter into a first EAC. Thereafter, in FIG. 2R, a balloon catheter 222 is introduced over guidewire 220 into the first EAC. In FIG. 2S, balloon catheter 222 is inflated to dilate the structures of ES. In FIG. 2T, guide catheter 218, guidewire 220 and balloon catheter 222 are withdrawn leaving a first new passage in the ES. The newly created passage in the ES facilitates drainage of the mucous through the ES. Alternatively, in FIG. 2U, only balloon catheter 222 is withdrawn. The position of guide catheter 218 is adjusted and guidewire 220 is introduced into a second EAC. In FIG. 2V, balloon catheter 222 is introduced over guidewire 220 into the second EAC. In FIG. 2W, balloon catheter 222 is inflated to dilate the structures of ES. In FIG. 2X, guide catheter 218, guidewire 220 and balloon catheter 222 are withdrawn leaving a second new passage in the ES. The second new passage in the ES further facilitates drainage of the mucous through the ES. This method of dilating the structures of ES can be repeated to create multiple new passages in the ES.

Figure 2Y:
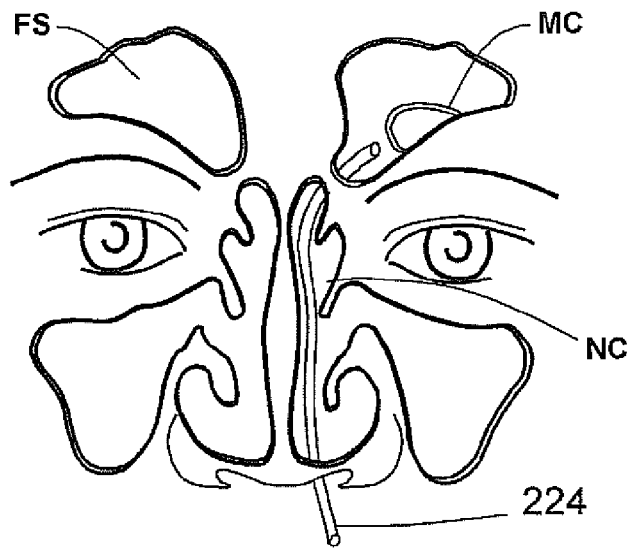
Figure 2Z:
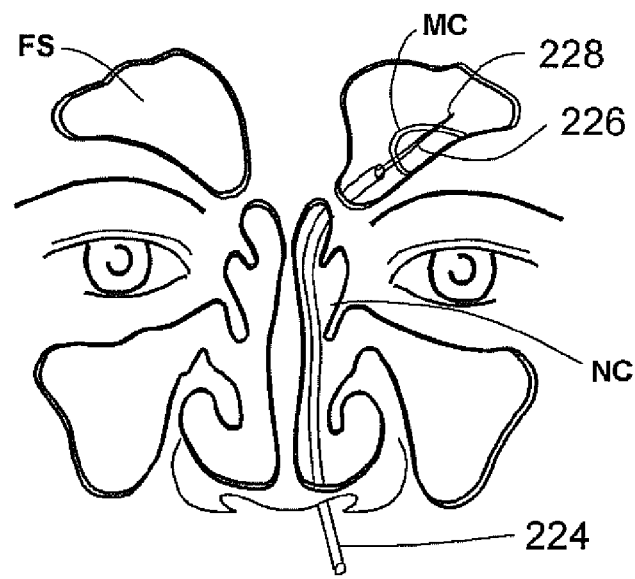
Figure 2A:
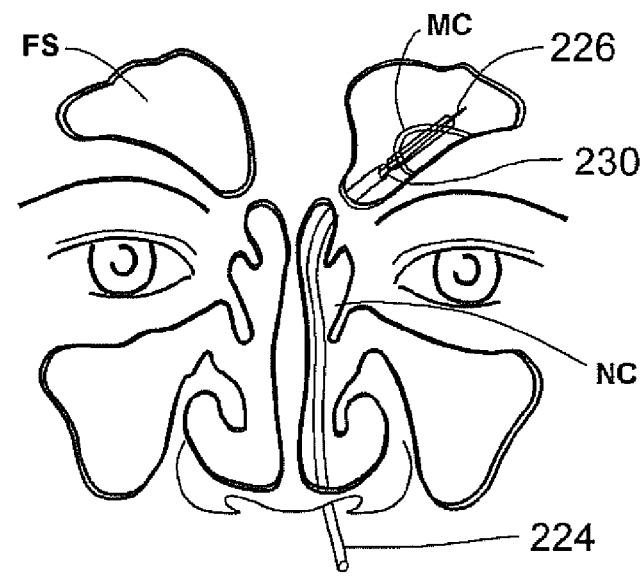
Figure 2A:
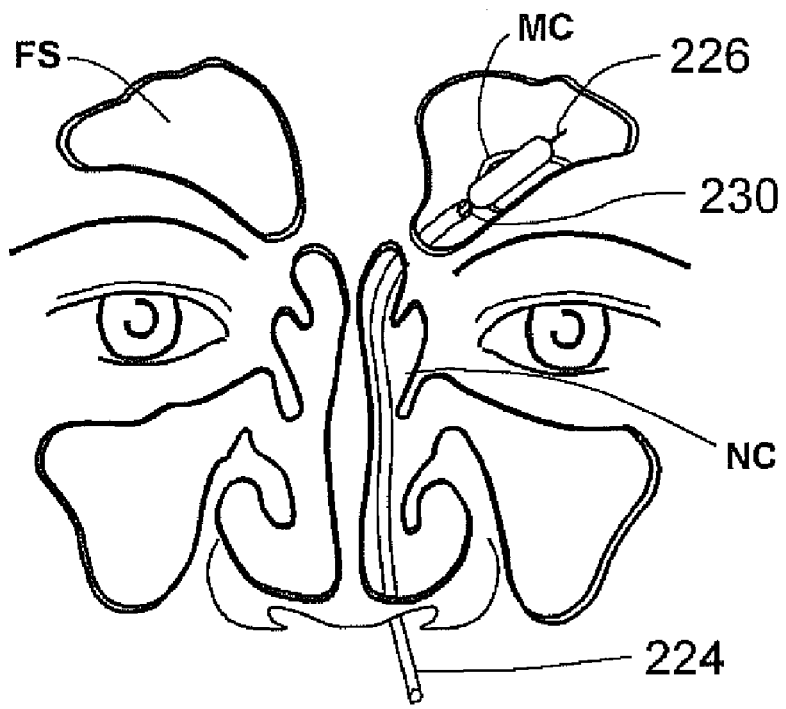
Figure 2A:
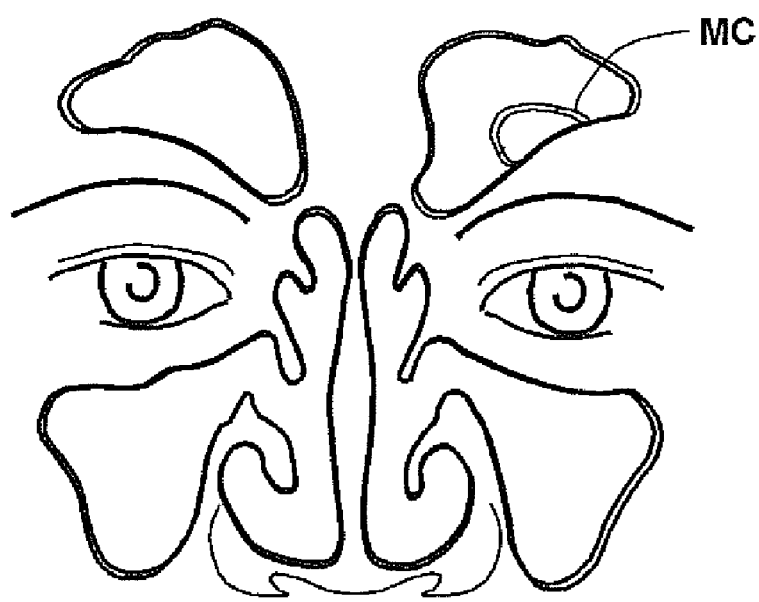

FIGS. 2Y through 2AC are partial coronal sectional views through a human head showing various steps of a method for treating a mucocele in a frontal sinus. In FIG. 2Y, an introducing device in the form of a guide catheter 224 is introduced in a frontal sinus FS through the nasal cavity NC. Frontal sinus FS has a mucocele MC to be treated. In FIG. 2Z, a penetrating device 226 comprising a sharp tip 228 is introduced through guide catheter 224 such that penetrating device 226 punctures the MC at least partially. In FIG. 2AA, a balloon catheter 230 is introduced over penetrating device 226 into the MC. Thereafter, in FIG. 2AB, balloon catheter 230 is inflated to rupture the MC and allow the drainage of contents of the MC. In FIG. 2AC, penetrating device 226 and balloon catheter 230 are withdrawn.

The methods disclosed herein may also comprise the step of cleaning or lavaging anatomy within the nose, paranasal sinus, nasopharynx or nearby structures including but not limited to irrigating and suctioning. The step of cleaning the target anatomy can be performed before or after a diagnostic or therapeutic procedure.

The methods of the present invention may also include one or more preparatory steps for preparing the nose, paranasal sinus, nasopharynx or nearby structures for the procedure, such as spraying or lavaging with a vasoconstricting agent (e.g., 0.025-0.5% phenylephyrine or Oxymetazoline hydrochloride (Neosynephrine or Afrin) to cause shrinkage of the nasal tissues, an antibacterial agent (e.g., provodine iodine (Betadine), etc. to cleanse the tissues, etc.

Figure 3A:
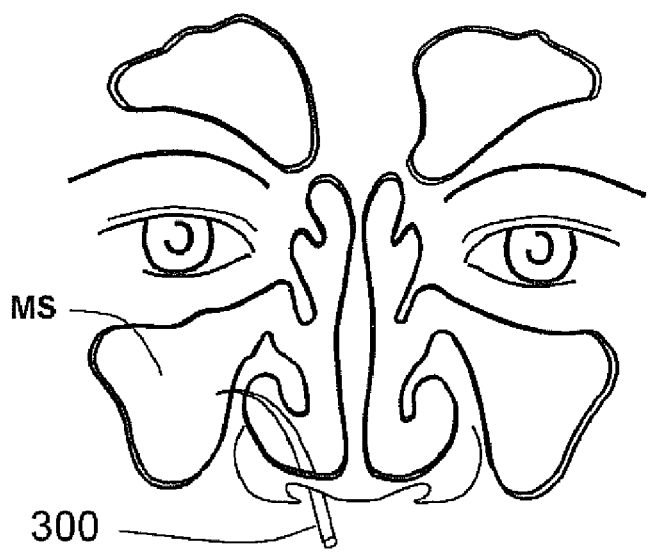
FIGS. 3A through 3C are partial coronal sectional views through a human head showing various steps of a method of accessing a paranasal sinus through an artificially created opening of the paranasal sinus.
Figure 3B:
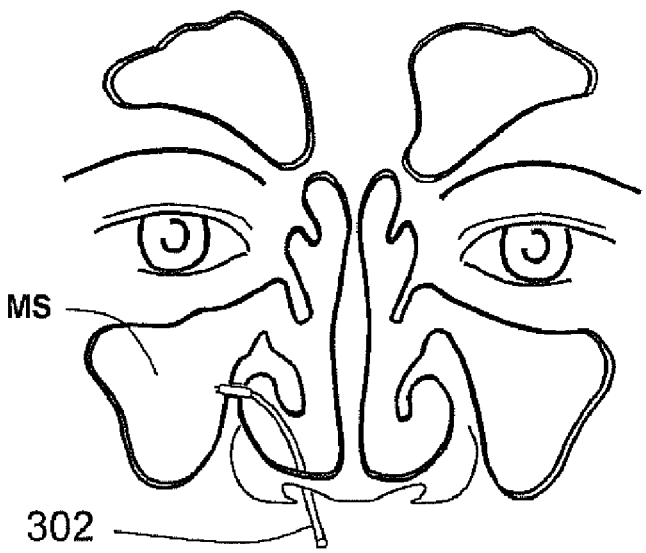
Figure 3C:
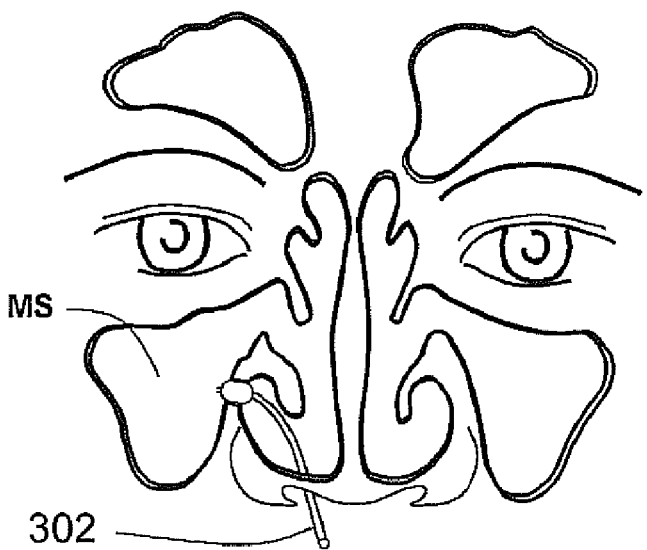

FIGS. 3A through 3C are partial coronal sectional views through a human head showing various steps of a method of accessing a paranasal sinus through an artificially created opening of the paranasal sinus. In FIG. 3A, a puncturing device 300 is inserted through a nostril and used to create an artificial opening in a maxillary sinus. There are several puncturing devices well known in the art like needles including needles, needles with bent shafts, dissectors, punches, drills, corers, scalpels, burs, scissors, forceps and cutters. In FIG. 3B, puncturing device 300 is withdrawn and a working device for example a balloon catheter 302 is introduced through the artificial opening into the maxillary sinus. In FIG. 3C, balloon catheter 302 is used to dilate the artificially created opening in the maxillary sinus. After this step, the balloon catheter 302 is withdrawn. It will be appreciated that, in some embodiments, the puncturing device 300 may have a lumen through which an introduction device (e.g., a guidewire or other elongate probe or member), may be inserted into the maxillary sinus and the puncturing device 300 may then be removed leaving such introduction device (e.g., a guidewire or other elongate probe or member) in place. In such cases, the working device (e.g., balloon catheter 302) may incorporate a lumen or other structure that allows the working device (e.g., balloon catheter 300) to be advanced over the previously inserted introduction device (e.g., a guidewire or other elongate probe or member).

Figure 4A:
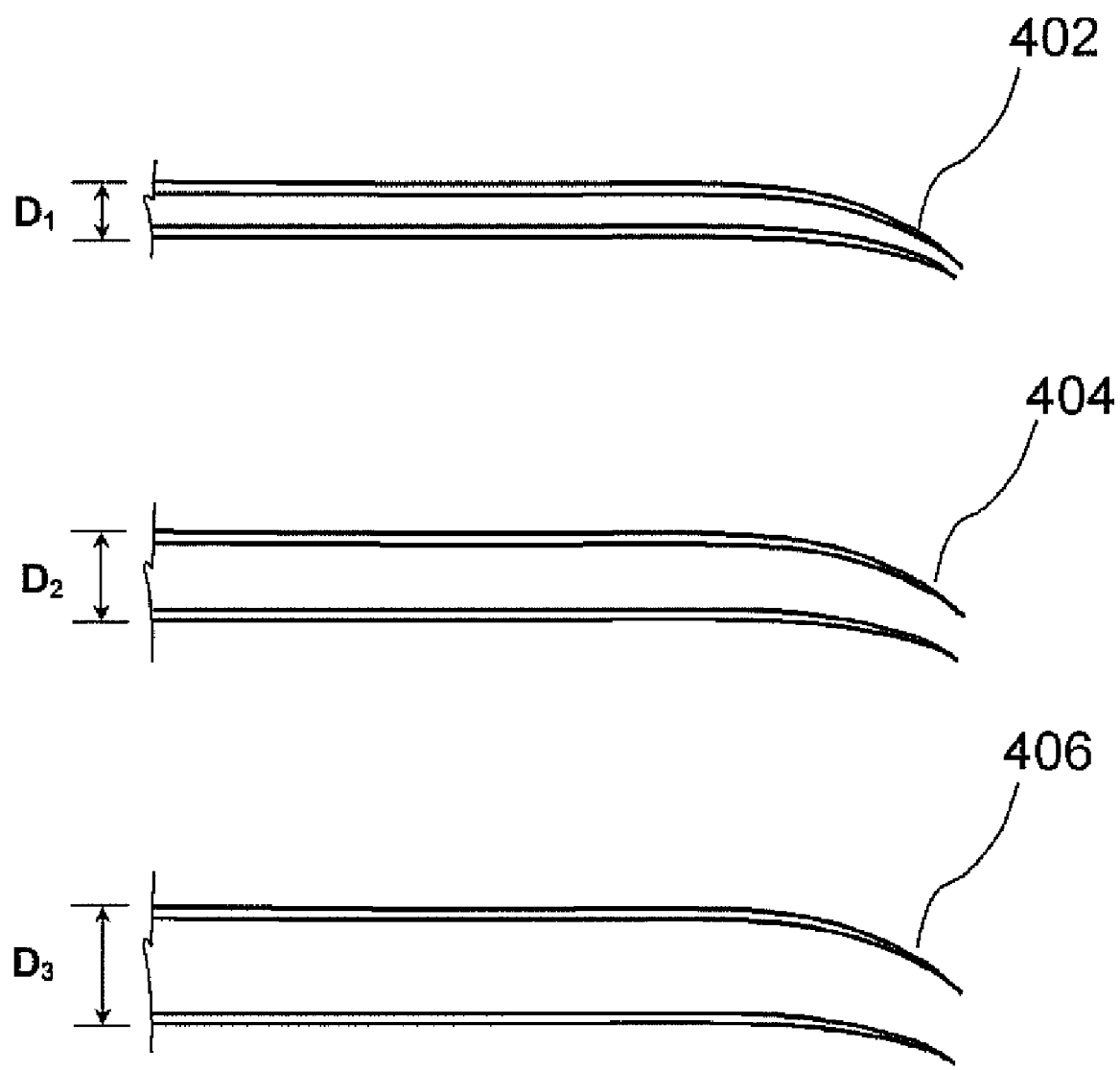
FIG. 4A shows a partial longitudinal sectional view of a system for dilating a sinus ostium or other intranasal anatomical structure, such system comprising three progressively larger dilators useable in sequence.

In the methods illustrated so far, balloon catheters were used only as an example for the several alternate working devices that could be used with this invention. FIG. 4A shows a sectional view of an example of a working device comprising a set of three sequential dilators: a first sequential dilator 402, a second sequential dilator 404 and a third sequential dilator 406. The $D_3$ of third sequential dilator 406 is greater than the diameter $D_2$ of second sequential dilator 404 which in turn is greater than the diameter $D_1$ of first sequential dilator 402. The sequential dilators may comprise one or more bent or angled regions. The sequential dilators can be constructed from a variety of biocompatible materials like stainless steel 316. A variety of other metals, polymers and materials can also be used to construct the sequential dilators.

Figure 4B:
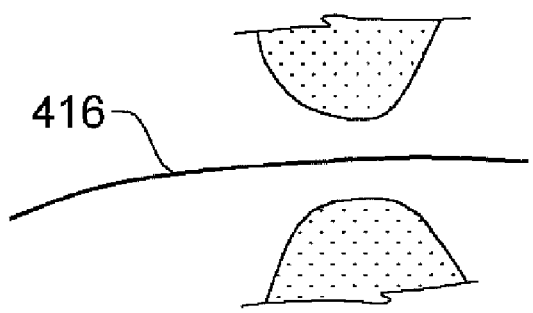
FIGS. 4B through 4E show various steps of a method of dilating a nasal cavity using a working device comprising a balloon catheter with a pressure-expandable stent.
Figure 4C:
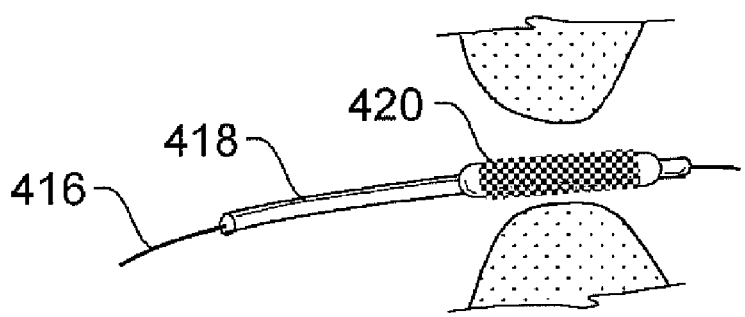
Figure 4D:
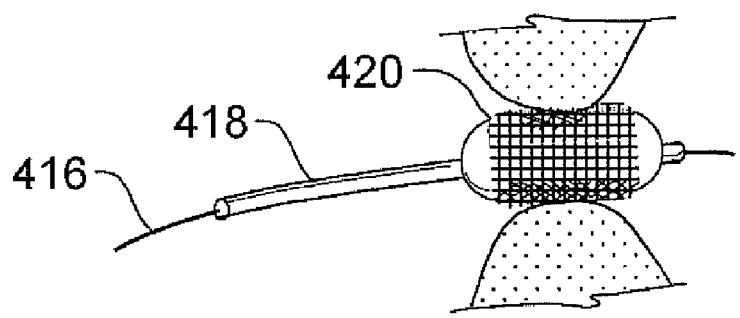
Figure 4E:
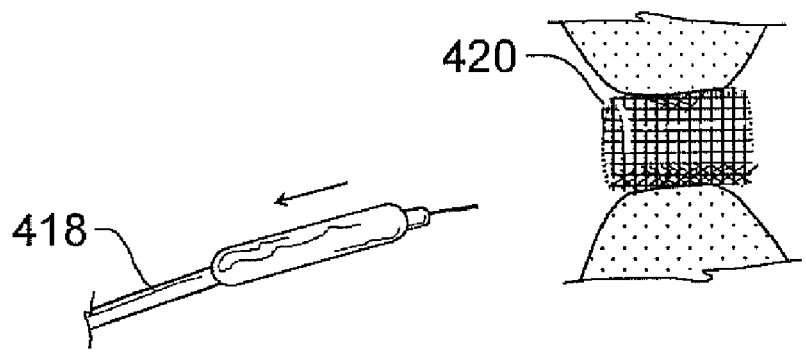

FIGS. 4B through 4E show various steps of a method of dilating a nasal cavity using a working device comprising a balloon catheter with a pressure-expandable stent. In FIG. 4B, an introducing device e.g. a guidewire 416 is introduced into a nasal cavity e.g. an ostium of a sinus. In FIG. 4C, a balloon catheter 418 is introduced over guidewire 416 into the nasal cavity. Balloon catheter 418 comprises a pressure-expandable stent 420. The position of balloon catheter 418 is adjusted so that pressure-expandable stent 420 is located substantially within the target anatomy where the stent is to be deployed. In FIG. 4D, the balloon of balloon catheter 418 is expanded to deploy pressure-expandable stent 420. In FIG. 4E, balloon catheter 418 is withdrawn leaving pressure-expandable stent 420 in the nasal cavity. Several types of stent designs can be used to construct stent 420 like metallic tube designs, polymeric tube designs, chain-linked designs, spiral designs, rolled sheet designs, single wire designs etc. These designs may have an open celled or closed celled structure. A variety of fabrication methods can be used for fabricating stent 420 including but not limited to laser cutting a metal or polymer element, welding metal elements etc. A variety of materials can be used for fabricating stent 420 including but not limited to metals, polymers, foam type materials, plastically deformable materials, super elastic materials etc. Some non-limiting examples of materials that can be used to construct the stent are silicones e.g. silastic, polyurethane, gelfilm and polyethylene. A variety of features can be added to stent 420 including but not limited to radiopaque coatings, drug elution mechanisms etc.

Figure 4F:
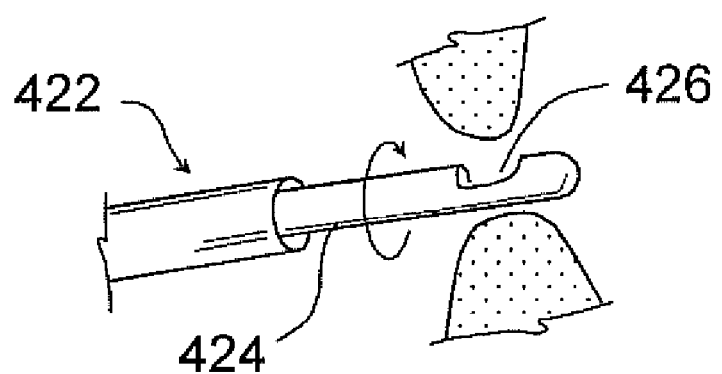
FIG. 4F shows a partial perspective view of a working device that comprises a side suction and/or side cutter.

FIG. 4F shows a partial perspective view of an embodiment of a working device comprising a side suction and/or cutting device 422 comprising a device body 424 having a side opening 426. Cutting device 422 is advanced into a passageway such as a nostril, nasal cavity, meatus, ostium, interior of a sinus, etc. and positioned so that side opening 426 is adjacent to matter (e.g., a polyp, lesion, piece of debris, tissue, blood clot, etc.) that is to be removed. Cutting device 422 is rotated to cut tissue that has been positioned in the side opening 426. Cutting device 422 may incorporate a deflectable tip or a curved distal end which may force side opening 426 against the tissue of interest. Further, this cutting device 422 may have an optional stabilizing balloon incorporated on one side of cutting device 422 to press it against the tissue of interest and may also contain one or more on-board imaging modalities such as ultrasound, fiber or digital optics, OCT, RF or electromagnetic sensors or emitters, etc.

Figure 4G:
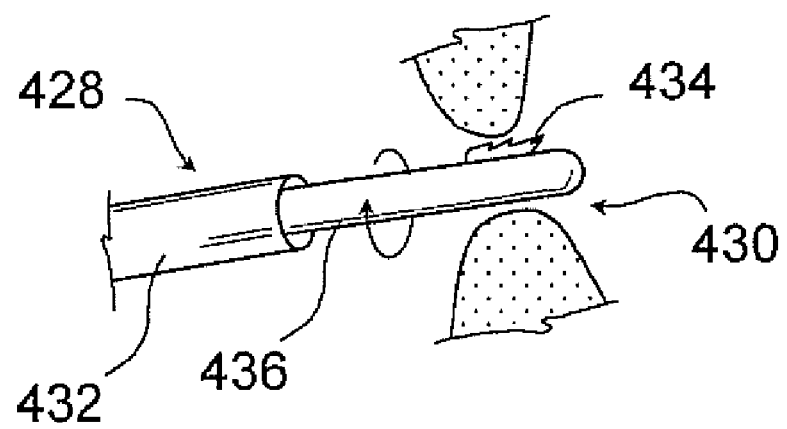
FIG. 4G shows a partial perspective view of a working device that comprises a rotating cutter to cut away tissue.

FIG. 4G shows a partial perspective view of an embodiment of a working device comprising a rotating cutter device to cut away tissue. Rotating cutter device 428 comprises a rotating member 430 enclosed in an introducing device 432. Rotating member 430 comprises a rotating blade 434 located near the distal region of rotating member 430. Rotating blade 434 may be retractable into rotating member 430. Rotating cutter device 428 is inserted in a passageway 436 such as a nostril, nasal cavity, meatus, ostium, interior of a sinus, etc. and positioned so that rotating blade 434 is adjacent to matter (e.g., a polyp, lesion, piece of debris, tissue, blood clot, etc.) that is to be removed. Thereafter, rotating member 430 is rotated to cause rotating blade 434 to remove tissue. In one embodiment, rotating member 430 can be retracted into introducing device 432. In another embodiment, rotating cutter device 428 may comprise a mechanism for suction or irrigation near the distal end of rotating cutter device 428.

Figure 4H:
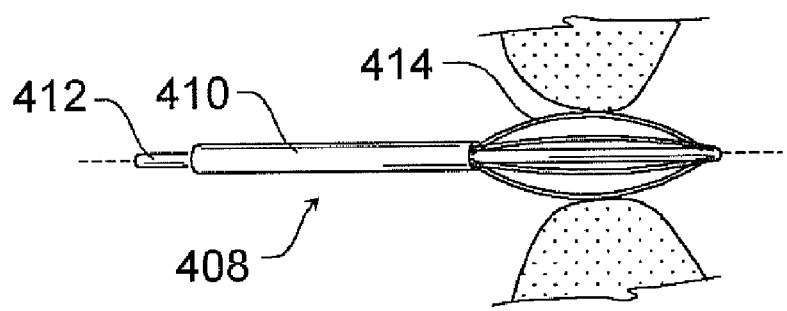
FIGS. 4H and 4I show various steps of a method of dilating the ostium of a paranasal sinus or other nasal passageway using a mechanical dilator.
Figure 4I:
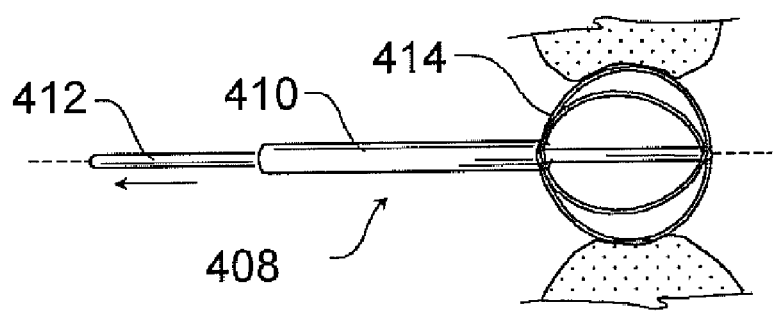

FIGS. 4H and 4I show various steps of a method of dilating a nasal cavity using a working device comprising a mechanical dilator 408. Mechanical dilator 408 comprises an outer member 410, an inner member 412 and one or more elongate bendable members 414. Inner member 412 can slide within outer member 410. The proximal ends of bendable members 414 are attached to distal end of outer member 410 and the distal ends of bendable members 414 are attached to distal end of inner member 412. In FIG. 4H, mechanical dilator 408 is inserted into an opening in the nasal anatomy e.g. an ostium of a sinus. Mechanical dilator 408 is positioned in the opening such that bendable members 414 are within the opening in the nasal anatomy. In FIG. 4I, relative motion of outer member 410 and inner member 412 causes the distal end of outer member 410 to come closer to the distal end of inner member 412. This causes bendable members 414 to bend such that the diameter of the distal region of mechanical dilator 408 increases. This causes bendable members 414 to come into contact with the opening in the nasal anatomy and exert an outward pressure to dilate the opening. Various components of mechanical dilator 408 like outer member 410, inner member 412 and bendable members 414 can be constructed from suitable biocompatible materials like stainless steel 316. A variety of other metals, polymers and materials can also be used to construct the various components of mechanical dilator 408. In one embodiment, outer member 410 is substantially rigid and inner member 412 is flexible. Outer member 410 can be substantially straight or may comprise one or more bent or angled regions. Inner member 412 may comprise one or more lumens.

Figure 4J:
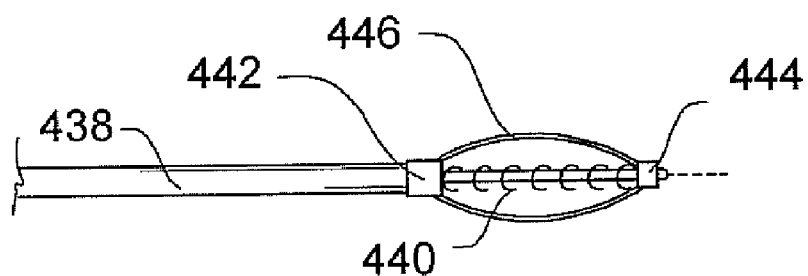
FIGS. 4J and 4K show perspective views of a mechanical dilator comprising a screw mechanism.
Figure 4K:
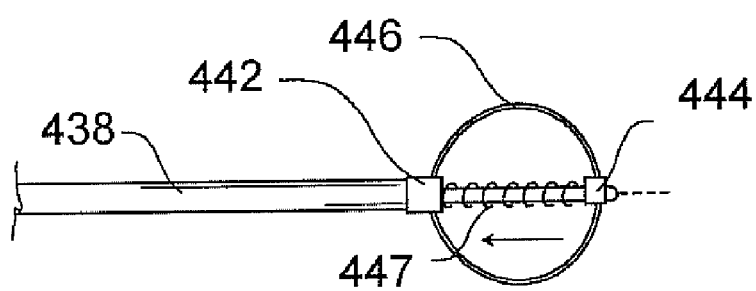

FIGS. 4J and 4K illustrate a perspective view of a design of a mechanical dilator comprising a screw mechanism. FIG. 4J shows the mechanical dilator comprising an outer member 438 and an inner screw member 440. Inner screw member 440 is connected to outer member 438 through a first pivot 442 located on the distal end of outer member 438. The distal end of inner screw member 440 is connected to a second pivot 444. The mechanical dilator further comprises one or more bendable members 446. The distal end of bendable members 446 is attached to second pivot 444 and the proximal end of bendable members 446 is attached to fist pivot 442. In FIG. 4K, inner screw member 440 is rotated in one direction. This causes second pivot 444 to come closer to first pivot 442. This causes bendable members 446 to bend in the radial direction exerting an outward radial force. This force can be used to dilate or displace portions of the anatomy. Outer member 438 can be substantially straight or may comprise one or more bent or angled regions. Inner screw member 440 may comprise one or more lumens.

FIGS. 4L and 4M illustrate sectional views of a design of a mechanical dilator comprising a pushable member. FIG. 4L shows the mechanical dilator comprising an outer member 448 comprising one or more bendable regions 449 on the distal end of outer member 448. Mechanical dilator further comprises an inner pushable member 450 comprising an enlarged region 452 on the distal end of inner pushable member 450. In FIG. 4M, inner pushable member 450 is pushed in the distal direction. This exerts an outward force on bendable regions 449 causing bendable regions 449 to bend in a radial direction exerting an outward force. This force can be used to dilate or displace portions of the anatomy. Outer member 448 can be substantially straight or may comprise one or more bent or angled regions. Inner pushable member 450 may comprise one or more lumens.

FIGS. 4N and 4O illustrate sectional views of a design of a mechanical dilator comprising a pullable member. FIG. 4N shows the mechanical dilator comprising an outer member 454 comprising one or more bendable regions 456 on the distal end of outer member 454. Mechanical dilator further comprises an inner pullable member 458 comprising an enlarged region 460 on the distal end of inner pullable member 458. In FIG. 4O, inner pullable member 458 is pulled in the proximal direction. This exerts an outward force on bendable regions 456 causing bendable regions 456 to bend in a radial direction exerting an outward force. This force can be used to dilate or displace portions of the anatomy. Outer member 454 can be substantially straight or may comprise one or more bent or angled regions. Inner pullable member 458 may comprise one or more lumens.

FIGS. 4P and 4Q illustrate sectional views of a design of a mechanical dilator comprising a hinged member. FIG. 4P shows the mechanical dilator comprising an outer member 462 comprising one or more bendable regions 464 located on the distal end of outer member 462. The mechanical dilator also comprises an inner member 466 located within outer member 462. In one embodiment, inner member 466 is tubular. The distal end of inner member 466 comprises one or more first hinges 468. First hinges 468 are hinged to the proximal ends of one or more moving elements 470. Distal ends of moving elements 470 are hinged to one or more second hinges 472 located on the inner surface of outer member 462. In FIG. 4Q, inner member 466 is pushed in the distal direction. This causes moving elements 470 to exert an outward radial force on bendable regions 464 causing bendable regions 464 to bend in an outward radial direction with an outward force. This outward force can be used to dilate or displace portions of the anatomy. Outer member 462 can be substantially straight or may comprise one or more bent or angled regions. Inner member 466 may comprise one or more lumens.

FIGS. 4R through 4W illustrate examples of configurations of mechanical dilators in FIGS. 4H through 4Q. FIG. 4R shows a sectional view of a mechanical dilator comprising an inner member 474, an outer stationary member 476 and an outer bendable member 478. In FIG. 4S, movement of inner member 474 displaces outer bendable member 478 in the radial direction with a force. This force can be used to dilate or displace portions of the anatomy. This configuration is useful to exert force in a particular radial direction. FIG. 4S' shows a partial perspective view of the outer stationary member 476 of FIG. 4R. FIG. 4T shows a sectional view of a mechanical dilator comprising an inner member 480, a first outer hemi-tubular member 482 and a second outer hemi-tubular member 484. In FIG. 4U, movement of inner member 480 displaces first outer hemi-tubular member 482 and second outer hemi-tubular member 484 in the radial direction with a force. This force can be used to dilate or displace portions of the anatomy. This configuration is useful to exert force in two diametrically opposite regions. FIG. 4U' shows a partial perspective view of the first outer hemi-tubular member 482 and the second outer hemi-tubular member 484 of FIG. 4T. FIG. 4V shows a sectional view of a mechanical dilator comprising an inner member 486, a first outer curved member 488 and a second outer curved member 490. In FIG. 4W, movement of inner member 486 displaces first outer curved member 488 and second outer curved member 490 in the radial direction with a force. This force can be used to dilate or displace portions of the anatomy. This configuration is useful to exert force over smaller areas in two diametrically opposite regions. FIG. 4W' shows a partial perspective view of the first outer curved member 488 and the second outer curved member 490 of FIG. 4V. Similar designs for mechanical dilators in FIGS. 4H through 4Q are possible using three or more displaceable members. The inner member in the mechanical dilators disclosed herein may be replaced by a balloon for displacing the outer members to exert an outward radial force.

Several other designs of the working device may also be used including but not limited to cutters, chompers, rotating drills, rotating blades, tapered dilators, punches, dissectors, burs, non-inflating mechanically expandable members, high frequency mechanical vibrators, radiofrequency ablation devices, microwave ablation devices, laser devices (e.g. $CO_2$, Argon, potassium titanyl phosphate, Holmium:YAG and Nd:YAG laser devices), snares, biopsy tools, scopes and devices that introduce diagnostic or therapeutic agents.

Figure 5A:
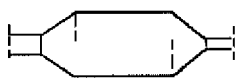
FIG. 5A shows a perspective view of a balloon that comprises a conical proximal portion, a conical distal portion and a cylindrical portion between the conical proximal portion and the conical distal portion.
Figure 5B:
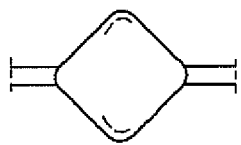
FIG. 5B shows a perspective view of a conical balloon.
Figure 5C:
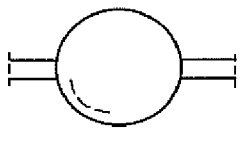
FIG. 5C shows a perspective view of a spherical balloon.
Figure 5D:
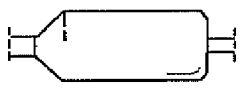
FIG. 5D shows a perspective view of a conical/square long balloon.
Figure 5E:
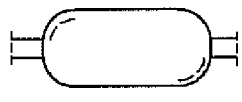
FIG. 5E shows a perspective view of a long spherical balloon.
Figure 5F:
FIG. 5F shows a perspective view of a bi-lobed "dog bone" balloon.
Figure 5G:
FIG. 5G shows a perspective view of an offset balloon.
Figure 5H:
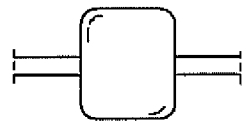
FIG. 5H shows a perspective view of a square balloon.
Figure 5I:
FIG. 5I shows a perspective view of a conical/square balloon.
Figure 5J:
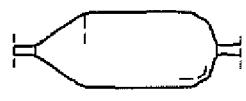
FIG. 5J shows a perspective view of a conical/spherical long balloon.
Figure 5K:
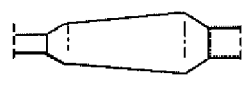
FIG. 5K shows a perspective view of an embodiment of a tapered balloon.
Figure 5L:
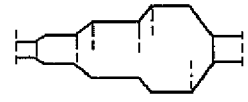
FIG. 5L shows a perspective view of a stepped balloon.
Figure 5M:
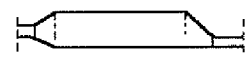
FIG. 5M shows a perspective view of a conical/offset balloon.
Figure 5N:
FIG. 5N shows a perspective view of a curved balloon.
Figure 5:
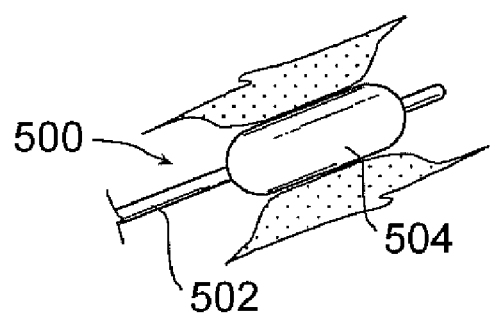
Figure 5:
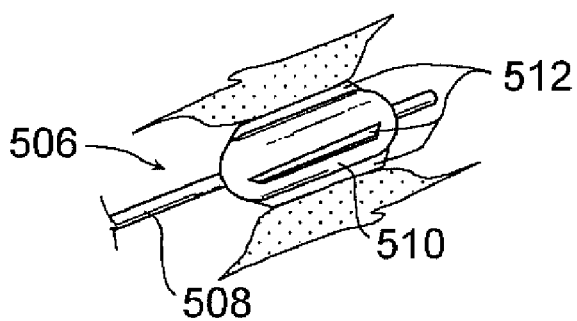
Figure 5:
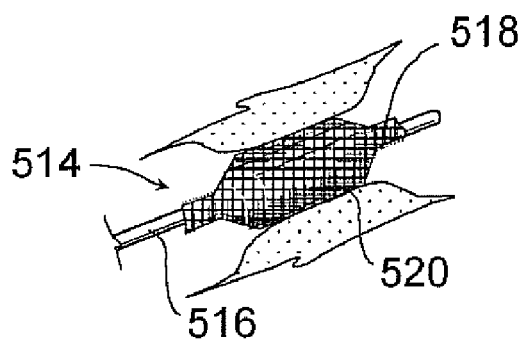
Figure 6:
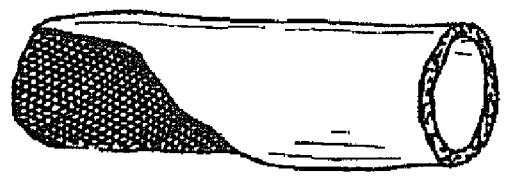
FIG. 6A shows a partial perspective view of a shaft design useable in the various devices disclosed herein, wherein the shaft comprises an external spiral wire.
FIG. 6B shows a partial perspective view of a shaft design for the various devices disclosed herein, wherein the shaft comprises a stiffening wire.
FIG. 6C shows a partial perspective view of an embodiment of a shaft design for the various devices disclosed herein, wherein the shaft comprises stiffening rings.
FIG. 6D shows a partial perspective view of a shaft design for the various devices disclosed herein, wherein the shaft comprises controllable stiffening elements.
FIG. 6E shows a partial perspective view of a shaft design for the various devices disclosed herein, wherein the shaft comprises a hypotube.
FIG. 6F shows a partial perspective cut-away view of a shaft design for the various devices disclosed herein, wherein the shaft comprises a braid.
FIG. 6G shows a partial perspective view of an embodiment of a device comprising a shaft having a plastically deformable region.
FIG. 6H shows a partial perspective view of a device comprising a shaft having a flexible element.
FIG. 6I shows a partial perspective view of a shaft comprising a malleable element.
FIG. 6J shows a partial perspective view of the shaft of FIG. 6I in a bent configuration.
FIG. 6K shows a cross sectional view through plane 6K-6K of FIG. 6I.
FIG. 6L shows a partial sectional view of an embodiment of a controllably deformable shaft.
FIG. 6M shows a partial sectional view of the controllably deformable shaft of FIG. 6L in a deformed state.
FIG. 6N shows a perspective view of a balloon catheter comprising a rigid or semi-rigid member.
FIGS. 6O through 6Q show sectional views of a balloon catheter that comprises an insertable and removable element.
Figure 6:
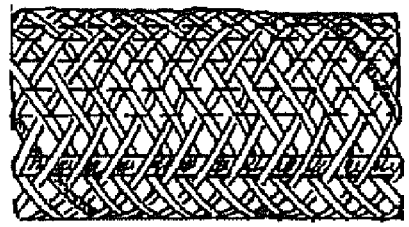
Figure 5:
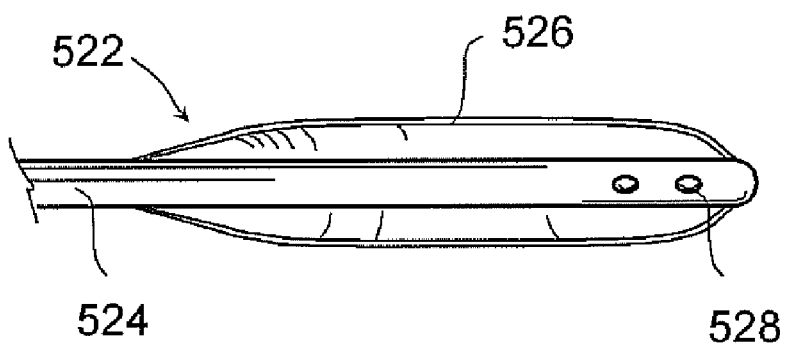
Figure 5:
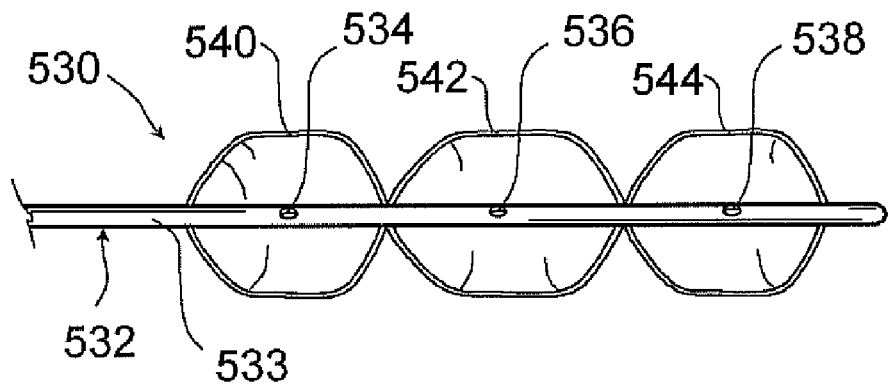
Figure 5:
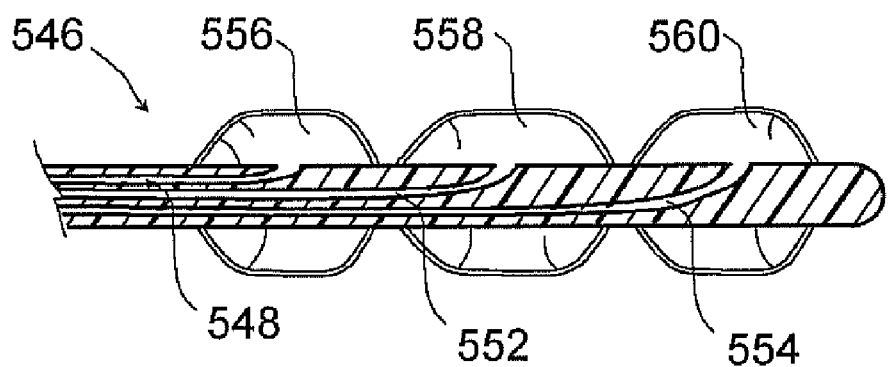
Figure 5:
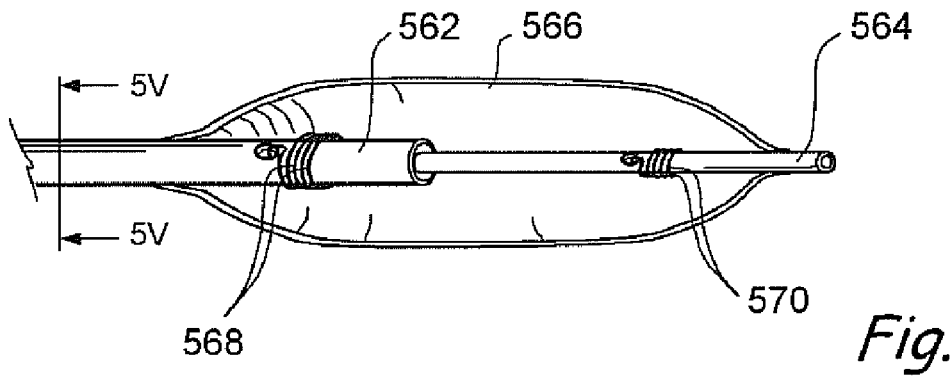
Figure 5:
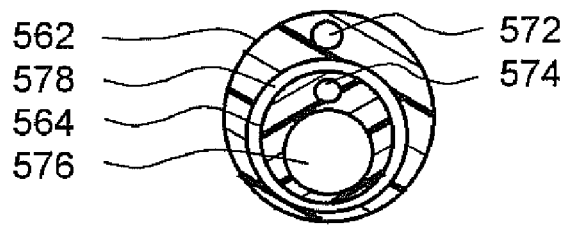
Figure 5:
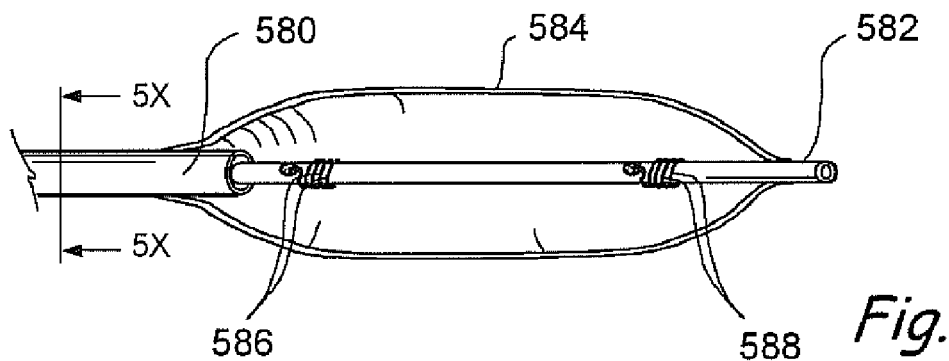
Figure 5:
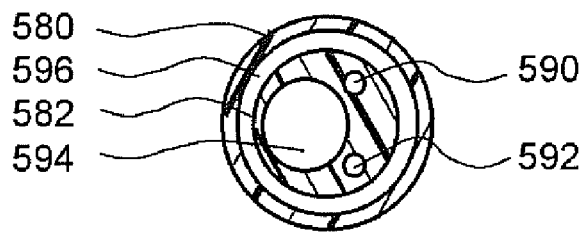

FIG. 5A shows a perspective view of an embodiment of a balloon comprising a conical proximal portion, a conical distal portion and a cylindrical portion between the conical proximal portion and the conical distal portion. FIGS. 5B to 5N show perspective views of several alternate embodiments of the balloon. FIG. 5B shows a conical balloon, FIG. 5C shows a spherical balloon, FIG. 5D shows a conical/square long balloon, FIG. 5E shows a long spherical balloon, FIG. 5F shows a dog bone balloon, FIG. 5G shows a offset balloon, FIG. 5H shows a square balloon, FIG. 5I shows a conical/square balloon, FIG. 5J shows a conical/spherical long balloon, FIG. 5K shows a tapered balloon, FIG. 5L shows a stepped balloon, FIG. 5M shows a conical/offset balloon and FIG. 5N shows a curved balloon.

The balloons disclosed herein can be fabricated from biocompatible materials including but not limited to polyethylene terephthalate, Nylon, polyurethane, polyvinyl chloride, crosslinked polyethylene, polyolefins, HPTFE, HPE, HDPE, LDPE, EPTFE, block copolymers, latex and silicone. The balloons disclosed herein can be fabricated by a variety of fabrication methods including but not limited to molding, blow molding, dipping, extruding etc.

The balloons disclosed herein can be inflated with a variety of inflation media including but not limited to saline, water, air, radiographic contrast materials, diagnostic or therapeutic substances, ultrasound echogenic materials and fluids that conduct heat, cold or electricity.

The balloons in this invention can also be modified to deliver diagnostic or therapeutic substances to the target anatomy. For example, FIG. 5O shows a partial perspective view of an embodiment of a balloon catheter device 500 comprising a balloon for delivering diagnostic or therapeutic substances. Balloon catheter device 500 comprises a flexible catheter 502 having a balloon 504 thereon. The catheter device 500 is advanced, with balloon 504 deflated, into a passageway such as a nostril, nasal cavity, meatus, ostium, interior of a sinus, etc. and positioned with the deflated balloon 504 situated within an ostium, passageway or adjacent to tissue or matter that is to be dilated, expanded or compressed (e.g., to apply pressure for hemostasis, etc.). Thereafter, the balloon 504 may be inflated to dilate, expand or compress the ostium, passageway, tissue or matter. Thereafter the balloon 504 may be deflated and the device 500 may be removed. This balloon 504 may also be coated, impregnated or otherwise provided with a medicament or substance that will elute from the balloon into the adjacent tissue (e.g., bathing the adjacent tissue with drug or radiating the tissue with thermal or other energy to shrink the tissues in contact with the balloon 504). Alternatively, in some embodiments, the balloon may have a plurality of apertures or openings through which a substance may be delivered, sometimes under pressure, to cause the substance to bathe or diffuse into the tissues adjacent to the balloon. Alternatively, in some embodiments, radioactive seeds, threads, ribbons, gas or liquid, etc. may be advanced into the catheter shaft 502 or balloon 504 or a completely separate catheter body for some period of time to expose the adjacent tissue and to achieve a desired diagnostic or therapeutic effect (e.g. tissue shrinkage, etc.).

The balloons in this invention can have a variety of surface features to enhance the diagnostic or therapeutic effects of a procedure. For example, FIG. 5P shows a partial perspective view of an embodiment of a balloon/cutter catheter device 506 comprising a flexible catheter 508 having a balloon 510 with one or more cutter blades 512 formed thereon. The device 506 is advanced, with balloon 510 deflated, into a passageway such as a nostril, nasal cavity, meatus, ostium, interior of a sinus, etc. and positioned with the deflated balloon 510 situated within an ostium, passageway or adjacent to tissue or matter that is to be dilated, expanded or compressed and in which it is desired to make one or more cuts or scores (e.g. to control the fracturing of tissue during expansion and minimize tissue trauma etc.). Thereafter, the balloon 510 is inflated to dilate, expand or compress the ostium, passageway, tissue or matter and causing the cutter blade(s) 512 to make cut(s) in the adjacent tissue or matter. Thereafter the balloon 510 is deflated and the device 506 is removed. The blade may be energized with mono or bi-polar RF energy or otherwise heated such that it will cut the tissues while also causing hemostasis and/or to cause thermal contraction of collagen fibers or other connective tissue proteins, remodeling or softening of cartilage, etc.

The balloons in this invention can have a variety of reinforcing means to enhance the balloon properties. For example, FIG. 5Q shows a perspective view of an embodiment of a balloon catheter device 514 comprising a flexible catheter 516 having a balloon 518 with one or more reinforcing means 520 thereon. In this example, reinforcing means 520 is a braid attached on the external surface of balloon 518. The reinforcing braid can be constructed from suitable materials like polymer filaments (e.g. PET or Kevlar filaments), metallic filaments (e.g. SS316 or Nitinol filaments) and metallic or non-metallic meshes or sheets. A variety of other reinforcing means can be used including but not limited to reinforcing coatings, external or internal reinforcing coils, reinforcing fabric, reinforcing meshes and reinforcing wires, reinforcing rings, filaments embedded in balloon materials etc. FIG. 5Q shows a perspective view of a reinforcing braid that can be used with the balloon catheter device.

The balloons in this invention can have a variety of inflation means to enhance the balloon properties. FIG. 5R shows a partial sectional view of an embodiment of a balloon catheter 522 comprising a shaft 524 and a balloon 526. Shaft 524 comprises a balloon inflation lumen. The distal portion of balloon inflation lumen terminates in inflation ports 528 located near the distal end of balloon 526. Thus, when balloon catheter 522 is inserted in an orifice and balloon 526 is inflated, the distal portion of balloon 526 inflates earlier than the proximal portion of balloon 526. This prevents balloon 526 from slipping back out of the orifice.

FIGS. 5S through 5T illustrate designs of balloon catheters comprising multiple balloons. FIG. 5S shows a partial sectional view of an embodiment of a balloon catheter 530 comprising a shaft 532 with a lumen 533. Lumen 533 opens into three orifices located on shaft 532 namely a first orifice 534, a second orifice 536 and a third orifice 538. The three orifices are used to inflate three balloons. First orifice 534 inflates a first balloon 540, second orifice 536 inflates a second balloon 542 and third orifice 538 inflates third balloon 544. In one embodiment, first balloon 540 and third balloon 544 are inflated with a single lumen and second balloon 542 is inflated with a different lumen. In another embodiment, first balloon 540, second balloon 542 and third balloon 544 interconnected and are inflated with a single lumen. A valve mechanism allows first balloon and second balloon to inflate before allowing second balloon to inflate.

Alternatively, the balloons can be inflated by separate lumens. FIG. 5T shows a partial sectional view of an embodiment of a balloon catheter 546 comprising a shaft 548 comprising a first inflation lumen 550, a second inflation lumen 552 and a third inflation lumen 554. The three inflation lumens are used to inflate three non-connected balloons. First inflation lumen 550 inflates a first balloon 556, second inflation lumen 552 inflates a second balloon 558 and third inflation lumen 554 inflates a third balloon 560.

The devices disclosed herein may comprise one or more navigation or visualization modalities. FIGS. 5U through 5AB illustrate perspective and sectional views of various embodiments of a balloon catheter comprising sensors. FIG. 5U shows a partial perspective view of a balloon catheter comprising an outer member 562, an inner member 564 and a balloon 566 attached to distal region of outer member 562 and distal region of inner member 564. The balloon catheter further comprises a first sensor 568 located on the distal region of outer member 562 and a second sensor 570 located on the distal region of inner member 564. FIG. 5V shows a cross section through plane 5V-5V in FIG. 5U. Outer member 562 comprises a first sensor lumen 572 to receive the lead from first sensor 568. Inner member 564 comprises a second sensor lumen 574 to receive the lead from second sensor 570. Inner member 564 further comprises a circular lumen 576. Outer member 562 and inner member 564 enclose an annular lumen 578. In one embodiment, annular lumen 578 is a balloon inflation lumen.

FIG. 5W shows a partial perspective view of a balloon catheter comprising an outer member 580, an inner member 582 and a balloon 584 attached to distal region of outer member 580 and distal region of inner member 582. The balloon catheter further comprises a first sensor 586 located on the distal region of inner member 582 and a second sensor 588 located on the distal region of inner member 582 distal to first sensor 586. FIG. 5X shows a cross section through plane 5X-5X in FIG. 5W. Inner member 582 comprises a first sensor lumen 590 to receive the lead from first sensor 586 and a second sensor lumen 592 to receive the lead from second sensor 588. Inner member 582 further comprises a circular lumen 594. Outer member 580 and inner member 582 enclose an annular lumen 596. In one embodiment, annular lumen 596 is a balloon inflation lumen.

Figure 5Y:
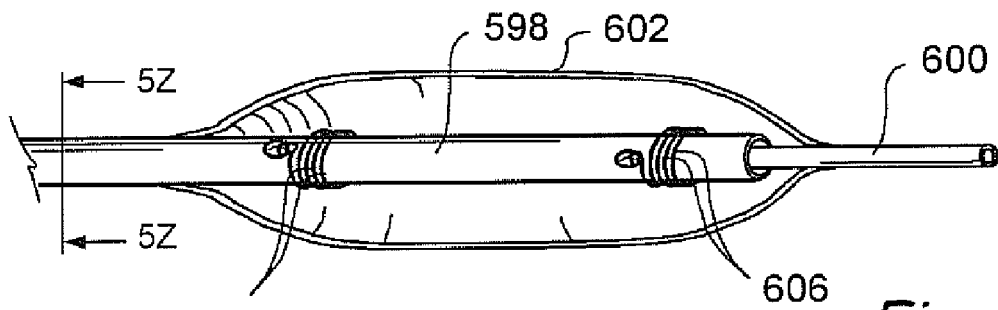
Figure 5Z:
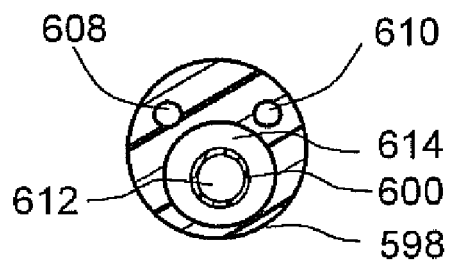
Figure 5A:
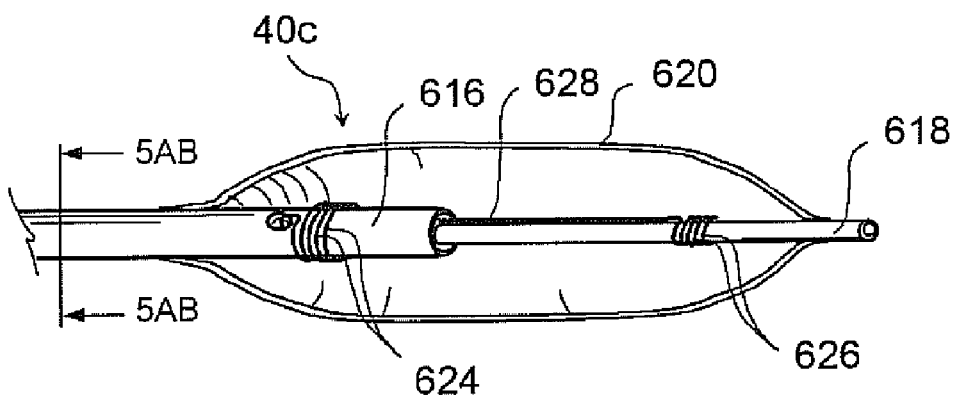
Figure 5A:
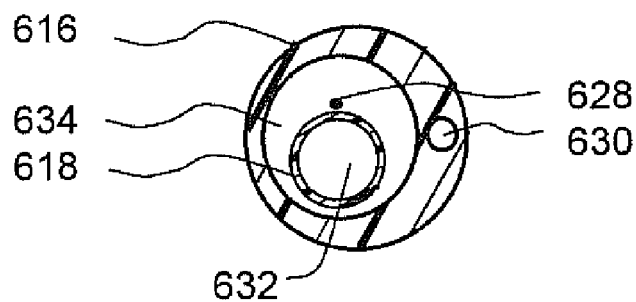

FIG. 5Y shows a partial perspective view of a balloon catheter comprising an outer member 598, an inner member 600 and a balloon 602 attached to distal region of outer member 598 and distal region of inner member 600. The balloon catheter further comprises a first sensor 604 located on the distal region of outer member 598 and a second sensor 606 located on the distal region of outer member 598 distal to first sensor 604. FIG. 5Z shows a cross section through plane 5Z-5Z in FIG. 5Y. Outer member 598 comprises a first sensor lumen 608 to receive the lead from first sensor 604 and a second sensor lumen 610 to receive the lead from second sensor 606. Inner member 600 comprises a circular lumen 612. Outer member 598 and inner member 600 enclose an annular lumen 614. In one embodiment, annular lumen 614 is a balloon inflation lumen.

The leads from the sensors may be attached on the surface of an element of the balloon catheter without being enclosed in a lumen. FIG. 5AA shows a partial perspective view of a balloon catheter comprising an outer member 616, an inner member 618 and a balloon 620 attached to distal region of outer member 616 and distal region of inner member 618. The balloon catheter further comprises a first sensor 624 located on the distal region of outer member 616 and a second sensor 626 located on the distal region of inner member 618. Second sensor 626 comprises a lead 628. FIG. 5AB shows a cross section through plane 5AB-5AB in FIG. 5AA. Outer member 616 comprises a first sensor lumen 630 to receive the lead from first sensor 624. Inner member 618 comprises a circular lumen 632. Lead 628 from second sensor 626 is attached on the outer surface of inner member 618 and is oriented parallel to inner member 618. Outer member 616 and inner member 618 enclose an annular lumen 634. In one embodiment, annular lumen 634 is a balloon inflation lumen. The sensors mentioned in FIGS. 5U through 5AB can be electromagnetic sensors or sensors including but not limited to location sensors, magnetic sensors, electromagnetic coils, RF transmitters, mini-transponders, ultrasound sensitive or emitting crystals, wire-matrices, micro-silicon chips, fiber-optic sensors, etc.

Figure 6A:
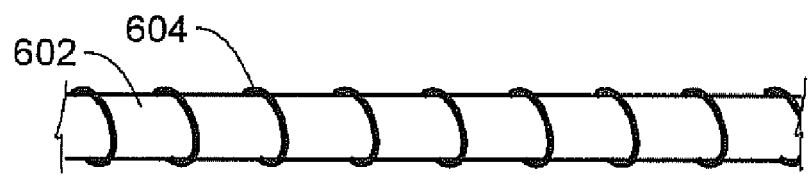
Figure 6B:
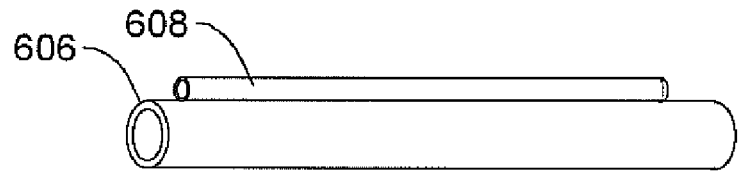
Figure 6C:
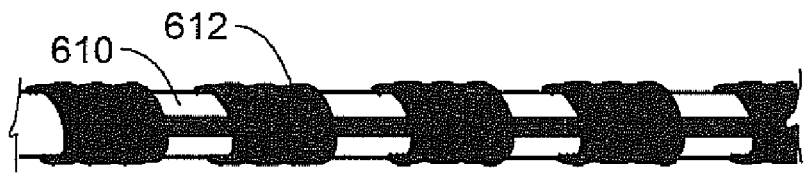
Figure 6D:
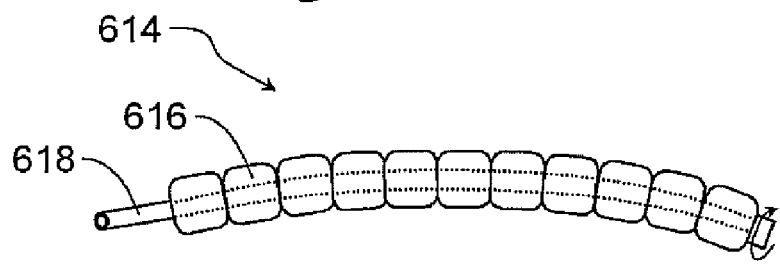
Figure 6E:
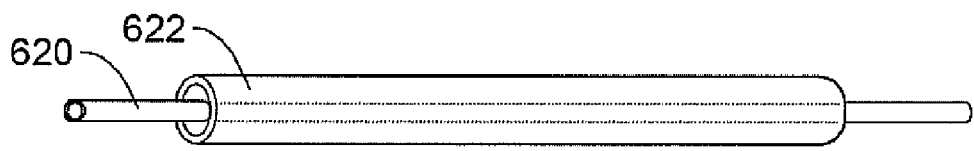
Figure 6:
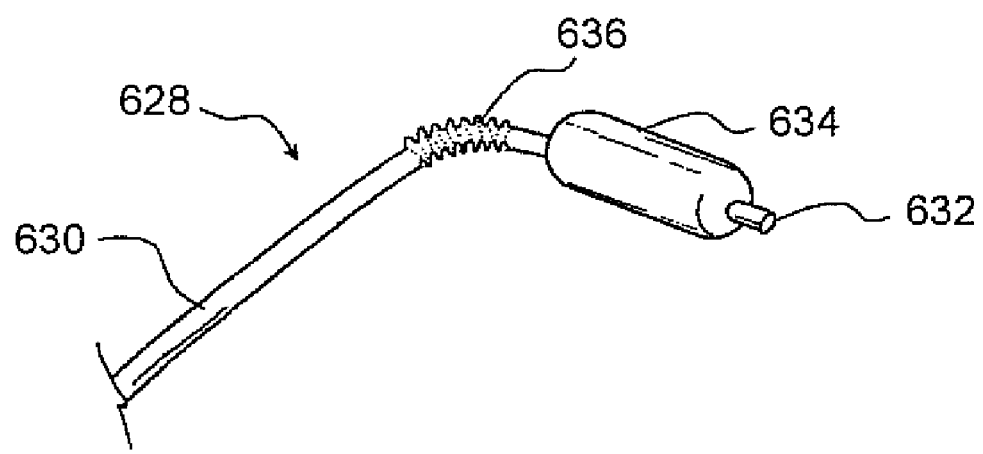
Figure 6:
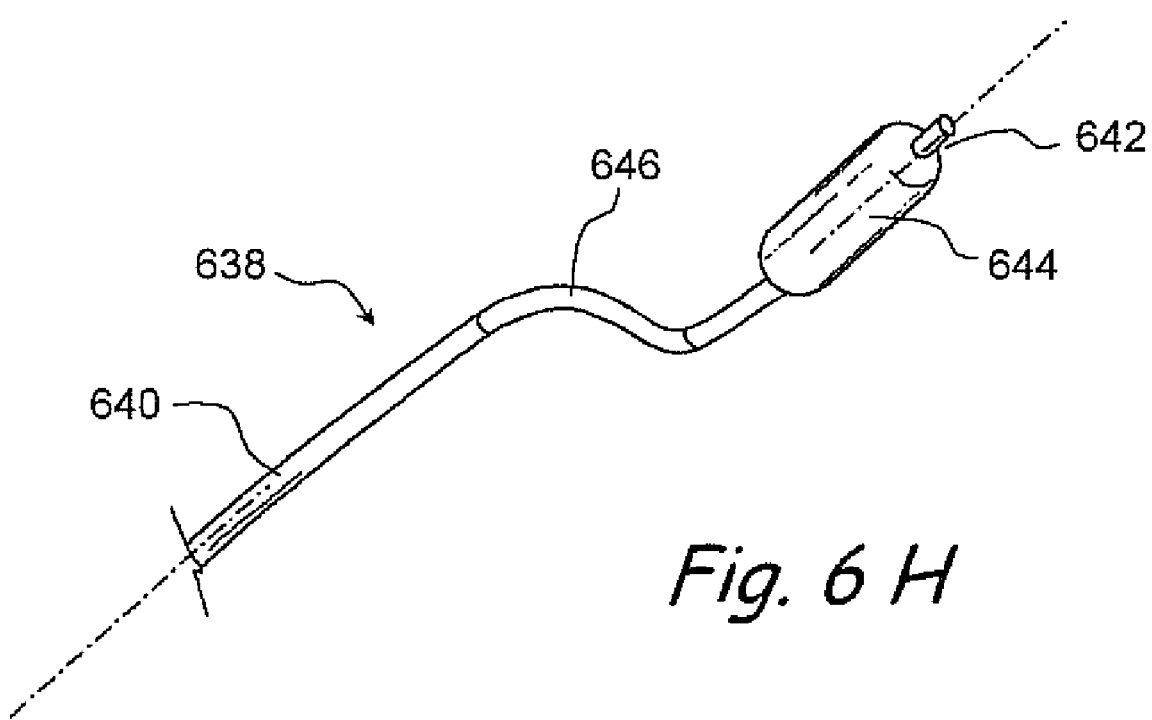
Figure 6:
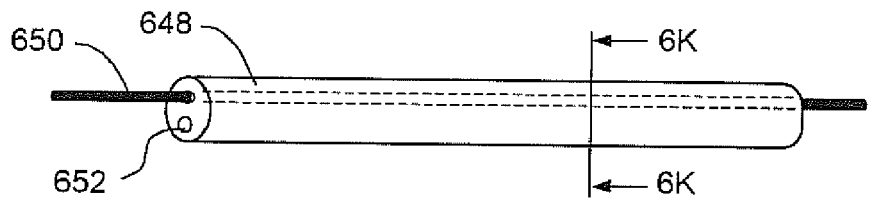
Figure 6:
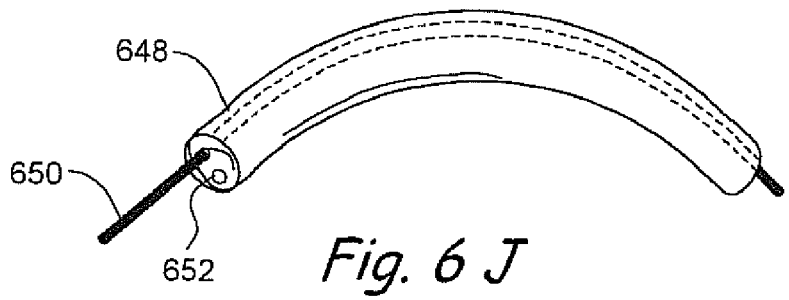
Figure 6:
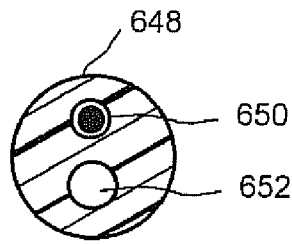
Figure 6:
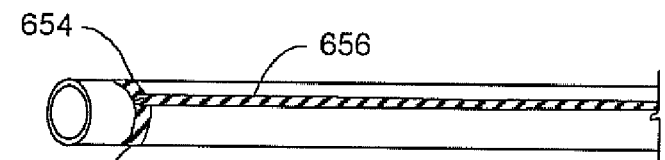
Figure 6:
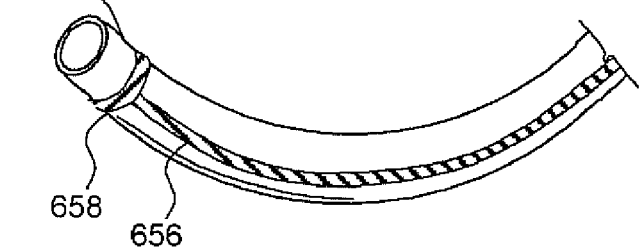
Figure 6:
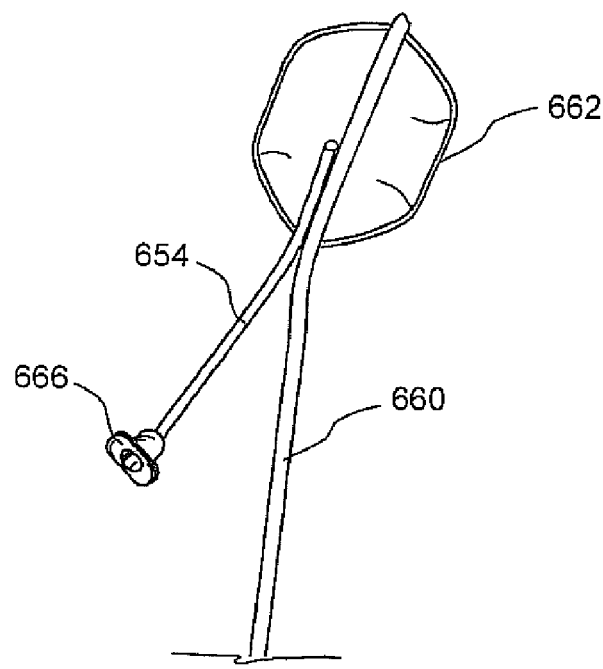
Figure 6:
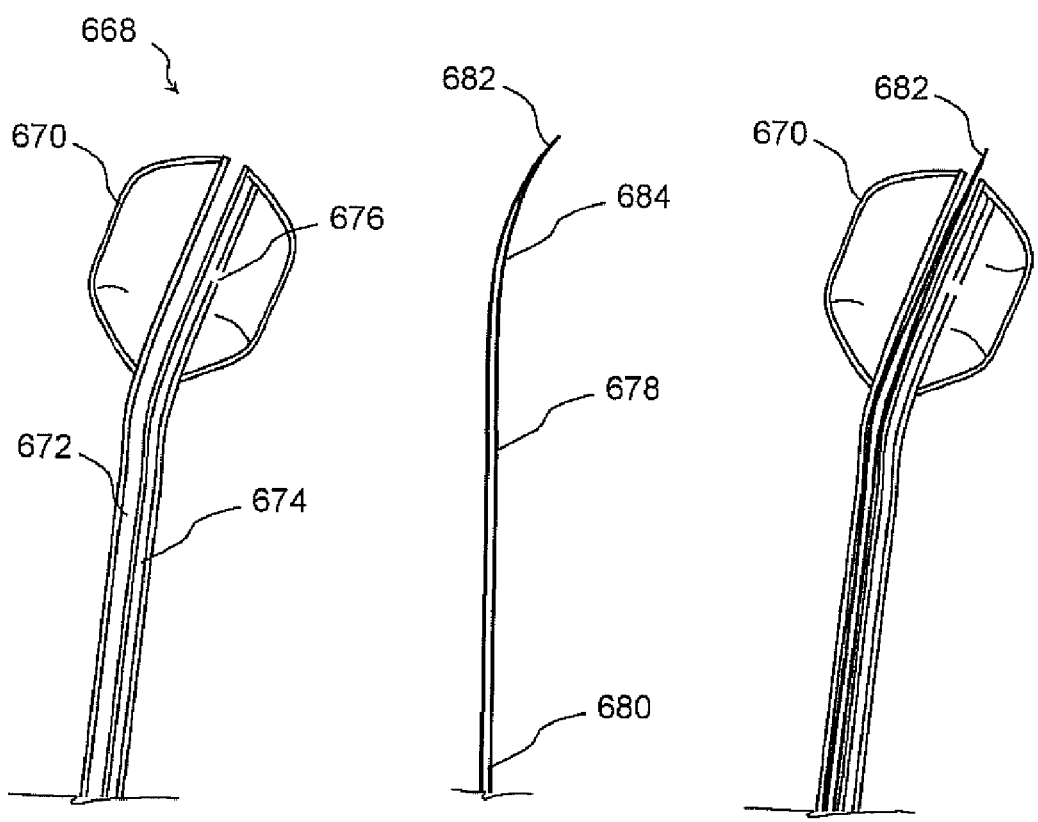

FIGS. 6A through 6G illustrate partial perspective views of several embodiments of shaft designs for the various devices disclosed herein. These shaft designs are especially useful for devices that encounter high torque or high burst pressures or require enhanced pushability, steerability and kink resistance. FIG. 6A shows a partial perspective view of an embodiment of a shaft 602 comprising a spiral element 604 wound around the shaft. Spiral element 604 can be made of suitable materials like metals (e.g. SS316L, SS304) and polymers. In one embodiment, spiral element 604 is in the form of round wire of diameter between 0.04 mm to 0.25 mm. In another embodiment, spiral element is in the form of flat wire of cross section dimensions ranging from 0.03 mm×0.08 mm to 0.08 mm×0.25 mm. FIG. 6B shows a partial perspective view of an embodiment of a shaft 606 comprising a reinforcing filament 608. Reinforcing filament 608 is substantially parallel to the axis of shaft 606. Shaft 606 with reinforcing filament 608 can be covered with a jacketing layer. Reinforcing filament 608 can be made of suitable materials like metals, polymers, glass fiber etc. Reinforcing filament 608 can also have shape memory characteristics. In one embodiment, reinforcing filament 608 is embedded in shaft 606. In another embodiment, reinforcing filament is introduced through a lumen in shaft 606. Shaft 606 may comprise more than one reinforcing filament 608. FIG. 6C shows a partial perspective view of an embodiment of a shaft 610 comprising one of more stiffening rings 612 along the length of shaft 610. FIG. 6D shows a partial perspective view of an embodiment of a shaft 614 comprising a series of controllably stiffening elements 616 along the length of the shaft. Shaft 614 further comprises a tension wire 618 that runs through controllably stiffening elements 616 and is attached to the most distal stiffening element. The tension in tension wire 618 causes controllably stiffening elements 616 to come into contact with each other with a force. Friction between controllably stiffening elements 616 causes shaft 614 to have a certain stiffness. Increasing the tension in tension wire 618 increases the force with which controllably stiffening elements 616 come into contact with each other. This increases the friction between controllably stiffening elements 616 which in turn increases the stiffness of shaft 614. Similarly, reducing the tension in tension wire 618 reduces the stiffness of shaft 614. Controllably stiffening elements 616 can be made from suitable materials like metal, polymers and composites. In one embodiment, controllably stiffening elements 616 are separated from each other by one or more springs. Tension wire 618 can be made from metals like SS316. Tension wire 618 may also be used to cause the device to actively bend or shorten in response to tension. FIG. 6E shows a partial perspective view of an embodiment of a shaft 620 comprising a hypotube 622. In one embodiment, hypotube 622 is located on the exterior surface of shaft 620. In another embodiment, hypotube 622 is embedded in shaft 620. Hypotube 620 can be made of metals like stainless steel 316 or suitable polymers. FIGS. 6F and 6F' show a partial perspective view of an embodiment of a shaft 624 comprising a reinforcing element 626 in the form of a reinforcing braid or mesh located on the outer surface of shaft 624. Reinforcing element 626 can be made of suitable materials like polymer filaments (e.g. PET or Kevlar filaments), metallic wires e.g. SS316 wires etc. The braid pattern can be regular braid pattern, diamond braid pattern, diamond braid pattern with a half load etc. In one embodiment, the outer surface of reinforcing element 626 is covered with a jacketing layer.

The shafts of various devices disclosed herein may be non homogenous along their length. Examples of such shafts are illustrated in FIGS. 6G through 6H. FIG. 6G shows a partial perspective view of an embodiment of a device comprising a shaft 628 comprising a proximal portion 630, a distal portion 632, a working element 634 and a plastically deformable region 636 located between the proximal portion 630 and distal portion 632. Plastically deformable region 636 can be deformed by a physician to adjust the angle between proximal portion 630 and distal portion 632. This enables the devices to be used for several different anatomical regions of the same patient. Also, such devices can be adjusted for optimal navigation through a patient's anatomy. In one embodiment, shaft 628 comprises multiple plastically deformable regions. In another embodiment plastically deformable region 636 is located within working element 634. Such a design comprising one or more plastically deformable regions can be used for any of the devices mentioned herein like catheters with working elements, guide catheters, guide catheters with a pre-set shape, steerable guide catheters, steerable catheters, guidewires, guidewires with a pre-set shape, steerable guidewires, ports, introducers, sheaths etc.

FIG. 6H shows a partial perspective view of an embodiment of a device comprising a shaft with a flexible element. The design is illustrated as a shaft 638 comprising a proximal portion 640, a distal portion 642 and a working element 644 (e.g. a balloon). Shaft 638 further comprises a flexible element 646 located between proximal portion 640 and distal portion 642. This design enables proximal portion 640 to bend with respect to distal portion 642 making it easier to navigate through the complex anatomy and deliver working element 644 to the desired location. In one embodiment, shaft 638 comprises multiple flexible elements. In another embodiment, flexible element 646 is located within working element 644. Such a design comprising one or more flexible elements can be used for any of the devices mentioned herein like catheters with working elements, guide catheters, guide catheters with a pre-set shape, steerable guide catheters, steerable catheters, guidewires, guidewires with a pre-set shape, steerable guidewires, ports, introducers, sheaths etc.

FIGS. 6I through 6K illustrate an example of a shaft comprising a malleable element. FIG. 6I shows a partial perspective view of an embodiment of a shaft 648 comprising malleable element 650 and a lumen 652 wherein shaft 648 is in a substantially straight configuration. Malleable element 650 is embedded in shaft 648 such that the axis of malleable element 650 is substantially parallel to the axis of shaft 648. FIG. 6J shows a partial perspective view of the embodiment of FIG. 6I in a bent configuration. FIG. 6K shows a cross sectional view through plane 6K-6K of FIG. 6I showing shaft 648 comprising malleable element 650 and a lumen 652. In one embodiment, shaft 648 comprises more than one malleable element.

FIGS. 6L through 6M show an embodiment of a controllably deformable shaft. FIG. 6L shows a partial sectional view of an embodiment of a controllably deformable shaft 654 comprising a pull wire 656 attached to a pull wire terminator 658 located near the distal end of shaft 654. FIG. 6M shows a partial sectional view of the controllably deformable shaft 654 of FIG. 6L in a bent orientation when pull wire 656 is pulled in the proximal direction. The deformation can be varied by varying the location of pull wire terminator 658 and the stiffness of various sections of shaft 658. The stiffness of a section of shaft 658 can be varied by adding reinforcing coatings, external or internal reinforcing coils, reinforcing fabric, reinforcing meshes and reinforcing wires, hinged elements, embedded filaments, reinforcing rings etc.

FIG. 6N shows a perspective view of a balloon catheter comprising a rigid or semi-rigid member. The balloon catheter comprises a rigid or semi-rigid member 660 and a balloon 662 located on the distal region of rigid or semi-rigid member 660. Rigid or semi-rigid member 660 may comprise one or more lumens. Rigid or semi-rigid member 660 may comprise one or more bent, curved or angled regions. Balloon 662 is inflated by a balloon inflation tube 664 comprising a hub 666 at the proximal end of balloon inflation tube 664. In one embodiment, balloon inflation tube 664 is fully attached along its length to rigid or semi-rigid member 660. In another embodiment, balloon inflation tube 664 is partially attached along its length to rigid or semi-rigid member 660.

FIGS. 6O through 6Q illustrate sectional views of a balloon catheter comprising an insertable and removable element. FIG. 6O shows a balloon catheter 668 comprising a balloon 670, a first lumen 672 and a balloon inflation lumen 674 opening into balloon 670 through an inflation port 676. FIG. 6P shows an insertable element 678 having a proximal end 680 and a distal end 682. In one embodiment, distal end 682 ends in a sharp tip for penetrating tissue. In one embodiment, insertable element 678 comprises one or more bent, angled or curved regions 684. Insertable element 678 can be fabricated from a variety of materials to obtain properties including but not limited to rigidity, shape memory, elasticity, ability to be plastically deformed etc. In FIG. 6Q, insertable element 678 is inserted into balloon catheter 668 through first lumen 672. This combination can be used to perform a diagnostic or therapeutic procedure. Insertable element 678 may be removed during or after the procedure.

Figure 7A:
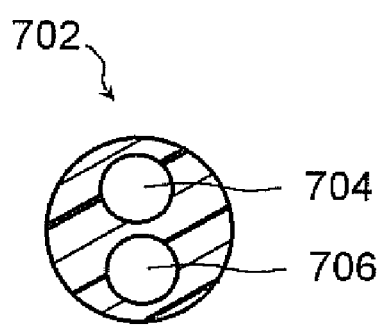
FIG. 7A shows a cross sectional view through a balloon catheter shaft comprising two cylindrical lumens.
Figure 7B:
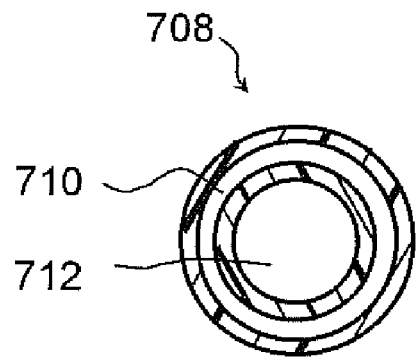
FIG. 7B shows a cross sectional view through a balloon catheter shaft comprising an inner lumen and an annular outer lumen disposed about the inner lumen.
Figure 7C:
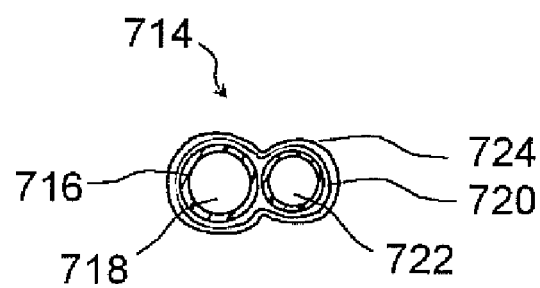
FIG. 7C shows a cross sectional view through a balloon catheter shaft which comprises a first tubular element with a first lumen, a second tubular element with a second lumen and a jacket surrounding the first and second tubular elements.
Figure 7D:
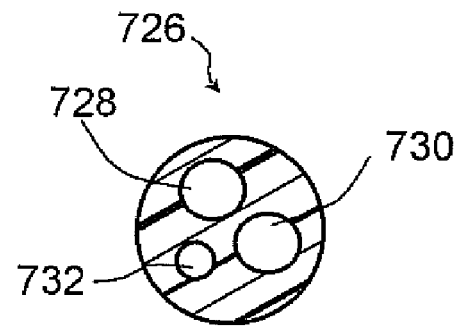
FIG. 7D shows a cross sectional view through a balloon catheter shaft comprising three lumens.
Figure 7E:
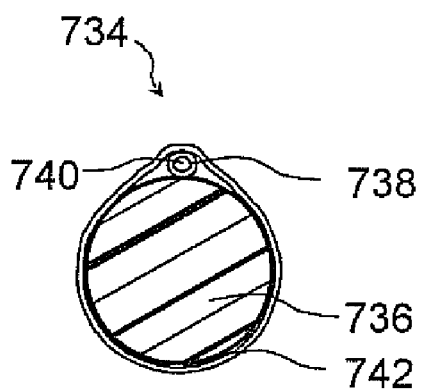
FIG. 7E shows a cross sectional view through a balloon catheter shaft comprising a cylindrical element, a tubular element that has a lumen and a jacket surrounding the cylindrical element and the tubular element.
Figure 7F:
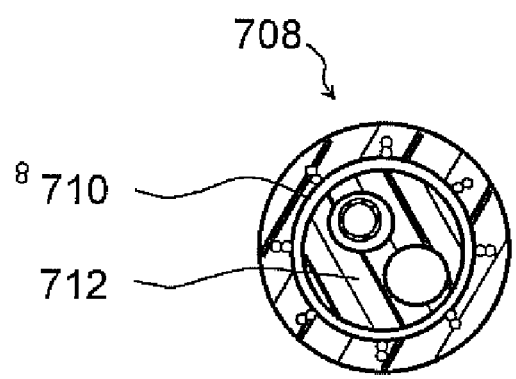
FIG. 7F shows a cross sectional view of through a balloon catheter shaft comprising an embedded braid.

FIGS. 7A through 7K show cross sectional views of several embodiments of lumen orientation in the devices disclosed herein. FIG. 7A shows a cross sectional view of an embodiment of a shaft 702 comprising a first lumen 704 and a second lumen 706. In one embodiment, first lumen 704 is a guidewire lumen and second lumen 706 is an inflation lumen. FIG. 7B shows a cross sectional view of an embodiment of a shaft 708 comprising a first lumen 710 and a annular second lumen 712 such that second annular lumen 712 is substantially coaxial with first lumen 710. In one embodiment, first lumen 710 is a guidewire lumen and annular second lumen 712 is an inflation lumen. FIG. 7C shows a cross sectional view of an embodiment of a shaft 714 comprising a first tubular element 716 comprising a first lumen 718, a second tubular element 720 comprising a second lumen 722 and a jacket 724 surrounding first tubular element 716 and second tubular element 720. In one embodiment, first lumen 718 is a guidewire lumen and second lumen 722 is an inflation lumen. FIG. 7D shows a cross sectional view of an embodiment of a shaft 726 comprising a first lumen 728, a second lumen 730 and a third lumen 732. In one embodiment, first lumen 728 is a guidewire lumen, second lumen 730 is an irrigation/aspiration lumen and third lumen 732 is an inflation lumen. FIG. 7E shows a cross sectional view of an embodiment of a shaft 734 comprising a cylindrical element 736, a tubular element 738 comprising a lumen 740 and a jacket 742 surrounding cylindrical element 736 and tubular element 738. FIG. 7F shows a cross sectional view of an embodiment of a shaft 744 comprising a tubular member 746 comprising a first lumen 748 and a second lumen 750; a first coating 752 located on the outer surface of tubular member 746; a braid 754 located on the outer surface of first coating 752 and a second coating 756 surrounding braid 754. First lumen 748 is lined with a suitable coating 758 like hydrophilic lubricious coating, hydrophobic lubricious coating, abrasion resisting coating etc. In one embodiment, first lumen 748 is a guidewire lumen and second lumen 750 is an inflation lumen. The lumens disclosed herein can be lined with suitable coatings like hydrophilic lubricious coatings, hydrophobic lubricious coatings, abrasion resisting coatings, radiopaque coatings, echogenic coatings etc.

Figure 7G:
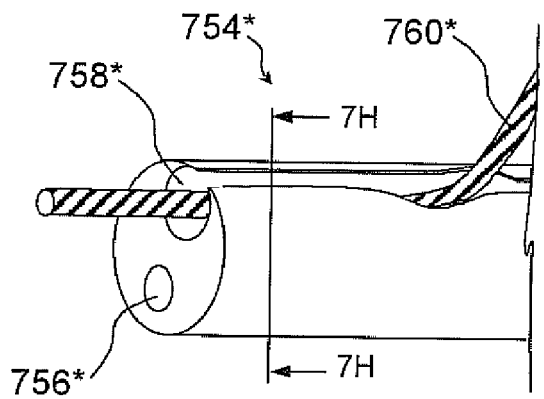
FIG. 7G shows a partial perspective view of a catheter shaft comprising a zipper lumen with a guide extending through a portion of the zipper lumen.
Figure 7H:
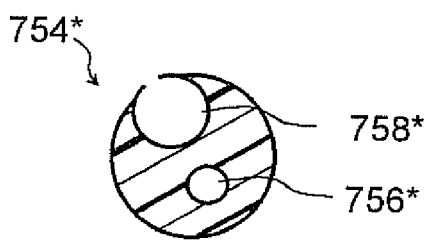
FIG. 7H shows a cross sectional view through line 7H-7H of FIG. 7G.

FIG. 7G shows a partial perspective view of an embodiment of a shaft 754* comprising a first lumen 756* and a zipper lumen 758*. Zipper lumen 758* allows a device like a guidewire 760* to be easily introduced into or removed from shaft 754*. FIG. 7H shows a cross sectional view through plane 7H-7H in FIG. 7G showing the orientations of first lumen 756* and zipper lumen 758*.

Figure 7I:
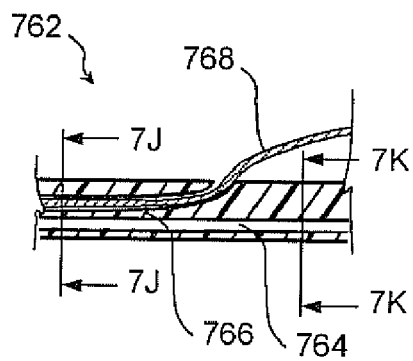
FIG. 7I shows is a partial longitudinal sectional view of a catheter shaft comprising a rapid exchange lumen with a guide extending through the rapid exchange lumen.
Figure 7J:
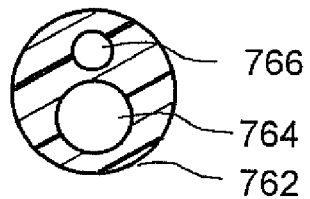
FIG. 7J shows a cross sectional view of the catheter shaft of FIG. 7I through line 7J-7J.
Figure 7K:
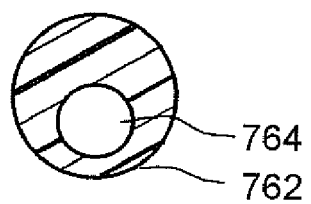
FIG. 7K shows a cross sectional view of the catheter shaft of FIG. 7I through line 7K-7K.

FIG. 7I shows a cross sectional view of an embodiment of a shaft 762 comprising a first lumen 764 and a rapid exchange lumen 766. Rapid exchange lumen 766 extends from the distal end of shaft 762 to a proximal region. Rapid exchange lumen 766 enables shaft 762 to be easily and quickly introduced or removed over an exchange device like a guidewire 768. FIG. 7J shows a cross sectional view through plane 7J-7J in FIG. 7I showing first lumen 764 and rapid exchange lumen 766. FIG. 7K shows a cross sectional view through plane 7K-7K in FIG. 7I showing first lumen 764.

Figure 7L:
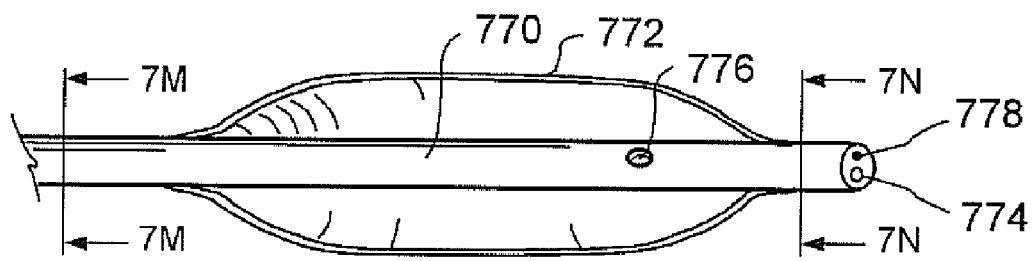
FIG. 7L is a partial perspective view of a balloon catheter device of the present invention comprising a through-lumen and a balloon inflation lumen within the shaft of the catheter.
Figure 7M:
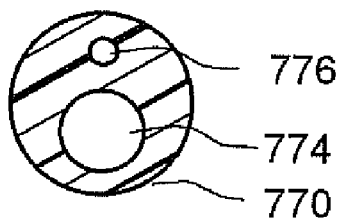
FIG. 7M is a cross sectional view through line 7M-7M of FIG. 7L.
Figure 7N:
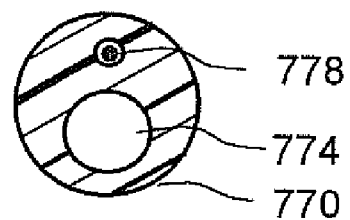
FIG. 7N is a cross sectional view through line 7N-7N of FIG. 7L.
Figure 7O:
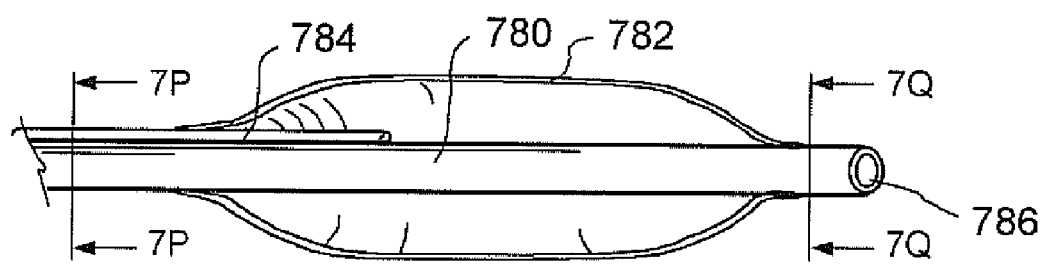
FIG. 7O is a partial perspective view of another balloon catheter device of the present invention comprising a through lumen within the shaft of the catheter and a balloon inflation tube disposed next to and optionally attached to the catheter shaft.
Figure 7P:
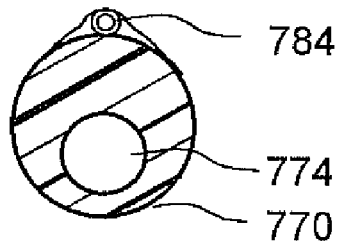
FIG. 7P is a cross sectional view through line 7P-7P of FIG. 7O.
Figure 7Q:
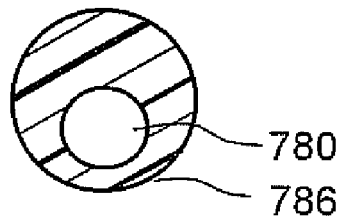
FIG. 7Q is a cross sectional view through line 7Q-7Q of FIG. 7O.

FIGS. 7L through 7Q shows perspective and sectional views of lumens for the devices disclosed herein that are not present throughout the length of the devices. FIG. 7L shows a perspective view of a balloon catheter comprising a shaft 770, a balloon 772 and a lumen 774 that is present throughout shaft 770. The balloon catheter further comprises a balloon inflation lumen 776 that opens into balloon 772. The distal end of balloon inflation lumen 776 is plugged with a plug 778. FIG. 7M shows a cross section through plane 7M-7M in FIG. 7L showing shaft 770 comprising lumen 774 and balloon inflation lumen 776. FIG. 7N shows a cross section through plane 7N-7N in FIG. 7L showing shaft 770 comprising lumen 774 and plug 778. FIG. 7O shows a perspective view of a balloon catheter comprising a shaft 780, a balloon 782 and a lumen 786 that is present throughout shaft 780. The balloon catheter further comprises a balloon inflation lumen 784. The distal end of balloon inflation lumen 784 opens into balloon 782. FIG. 7P shows a cross section through plane 7P-7P in FIG. 7O showing shaft 780 comprising lumen 786 and balloon inflation lumen 784. FIG. 7Q shows a cross section through plane 7Q-7Q in FIG. 7O showing shaft 780 comprising lumen 786.

FIGS. 8A through 8E show partial perspective views of several embodiments of markers that may be present on the elements of the devices mentioned herein. FIG. 8A shows a partial perspective view of an embodiment of a shaft 800 comprising a plurality of distance markers 802 located along the length of shaft 800. FIG. 8B shows a partial perspective view of an embodiment of a shaft 804 comprising a plurality of radiographic markers 806 located along the length of shaft 804. FIG. 8C shows a partial perspective view of an embodiment of a shaft 808 comprising a plurality of ring shaped radiographic markers 810 located along the length of shaft 808. FIG. 8D shows a partial perspective view of an embodiment of a balloon catheter 812 comprising a shaft 814 and a balloon 816. Balloon 816 comprises a plurality of radiographic markers 818 located on the outer surface of the balloon 816. Such markers 818 may be in a linear arrangement, non-linear arrangement or any other configuration that performs the desired marking function (e.g., delineating the length and/or diameter of the balloon, marking the proximal and/or distal ends of the balloon, etc.). FIGS. 8E and 8E' show partial perspective and longitudinal sectional views of an embodiment of a balloon catheter 820 comprising a shaft 822 and a balloon 824. Balloon 824 comprises a plurality of radiographic markers 826 located on the inner surface of the balloon 824. Such markers 826 may be in a linear arrangement, non-linear arrangement or any other configuration that performs the desired marking function (e.g., delineating the length and/or diameter of the balloon, marking the proximal and/or distal ends of the balloon, etc.). The devices disclosed herein may also comprise several other types of markers like ultrasound markers, radiofrequency markers and magnetic markers. Similarly, the devices disclosed herein may also comprise one or more sensors like electromagnetic sensors, electrical sensors, magnetic sensors, light sensors and ultrasound sensors.

FIGS. 9A-9D show components that may be used alone or in various combinations to perform transnasal procedures within paranasal sinuses and/or within openings (e.g., any transnasally accessible opening in a paranasal sinus or air cell including but not limited to; natural ostia, surgically altered natural ostia, surgically created openings, antrostomy openings, ostiotomy openings, burr holes, drilled holes, ethmoidectomy openings, natural or man made passageways, etc.) in paranasal sinuses. These devices may be sold or used separately or together (e.g., as a system or kit).

Figure 9:
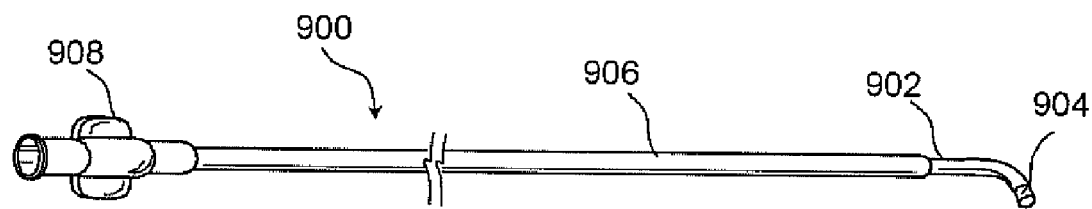
FIG. 9A is a side view of a tubular guide device of the present invention.
FIG. 9B is a side view of a guidewire of the present invention.
FIG. 9C is a side view of a tubular sheath of the present invention.
FIG. 9D is a side view of a balloon catheter of the present invention.
Figure 9:
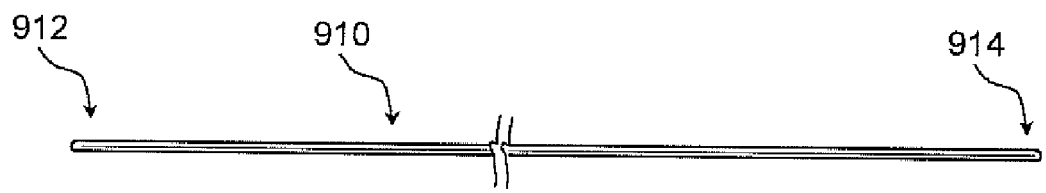
Figure 9:
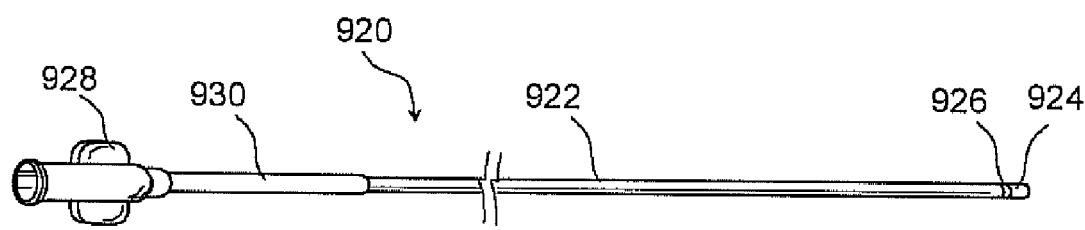
Figure 9:
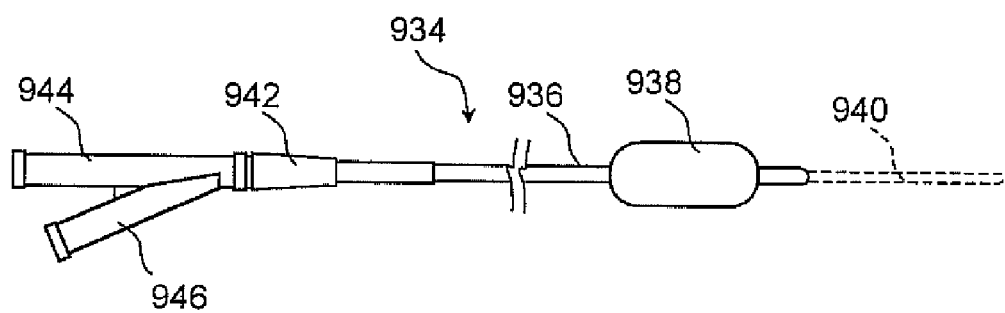

FIG. 9A shows a side view of a guide device 900 that comprises an elongate tube 902. Elongate tube 902 may be made of suitable biocompatible material(s) such polymers (e.g. Nylon, elastomeric polyether block amide (PEBAX), etc. The distal portion of elongate tube 902 may comprise a bent, angled or curved region. The inner surface of elongate tube 902 may be lined by a lubricious coating or a tubular lubricious liner. Such a lubricious coating or tubular lubricious liner is useful to facilitate passage of one or more devices through the lumen of guide device 900 especially when guide device 900 comprises an angled, curved or bent region. The distal portion of elongate tube 902 may comprise an atraumatic tip 904. Atraumatic tip 904 may be made of suitable biocompatible materials such as Pebax, etc. Atraumatic tip 904 prevents or reduces damage to the anatomy caused by the distal end of guide device 900. Guide device 900 further comprises a stiffening element e.g. a hypotube 906. Hypotube 906 may be made of suitable biocompatible materials such as stainless steel, titanium, nickel-titanium alloys (e.g., Nitinol), polymers such as Nylon etc. In one embodiment, guide device 900 further comprises an outer cover. The outer cover may be made of Nylon or other thermoplastic material. The outer cover substantially surrounds the outer surface of hypotube 906 and a region of elongate tube 902 emerging from the distal end of hypotube 906. This embodiment comprising an outer cover is especially useful for providing an outer lubricious surface on guide device 900. This embodiment comprising an outer cover is also useful for improving joint integrity between hypotube 906 and elongate tube 902. This embodiment comprising an outer cover is also useful for creating a smooth transition between the distal portion of elongate tube 902 and the distal end of hypotube 906. The proximal end of guide device 900 comprises a hub 908. In one embodiment, hub 908 is a female luer hub. The length of the portion of the guide device 900 that enters the body may range preferably from 2 inches to 6 inches, and the length of the portion that remains outside of the body is preferably at least 0.5 inches. Guide device 900 may be used for introducing one or more devices into the anatomy. Guide device 900 may also be used for applying suction to or providing lavage to an anatomical region. Proximal portion of guide device 900 may comprise a rotating valve device such as a Touhy-Borst device to lock down a device such as a sheath, guidewire, balloon catheter or other devices that are being inserted through guide device 900. Similarly, a Touhy-Borst device may be present on the proximal end of one or more devices disclosed herein. The distal region of guide device 900 or any other guide device disclosed herein may comprise a radiopaque marker such as a metal, polymer loaded with a radiopaque substance, etc. In one embodiment, multiple guide devices 900 of varying designs are provided in the system shown in FIGS. 9A through 9D. The system shown in FIGS. 9A through 9D may comprise more than one guide device.

FIG. 9B shows a side view of a guidewire 910. The outer diameter of guidewire 910 is preferably greater than 0.020 inches. In one embodiment, the outer diameter of guidewire 910 is 0.035 inches. Guidewire 910 comprises a proximal portion 912 and a distal portion 914. Distal portion 914 may comprise a substantially floppy tip. Stiffness of guidewire 910 may vary along the length of guidewire 910. In one embodiment, guidewire 910 comprises a lubricious coating made of materials such as polytetrafluoroethylene (PTFE). Guidewire 910 may comprise one or more radiopaque markers. The outer diameter of guidewire 910 is designed to enable passage of guidewire 910 through the balloon catheter shown in FIG. 9D. In one embodiment, outer diameter of guidewire 910 is 0.035 inches. Guidewire 910 can be used to introduce one or more devices into the anatomy. The system shown in FIGS. 9A through 9D may comprise more than one guidewire.

FIG. 9C shows a side view of a tubular sheath device 920 of the present invention. Sheath device 920 comprises an elongate tube 922 that may be made of any suitable biocompatible material(s) including, but not limited to polyethylene, elastomeric polyether block amide (PEBAX), etc. In one embodiment, elongate tube 922 may comprise a composite structure tube with lubricious inner liner, stainless steel braid or coil and a polymer jacket. The distal end of elongate tube 922 may comprise an atraumatic tip 924 that prevents or reduces damage to the anatomy caused by the distal end of elongate tube 922. The atraumatic tip may be made of a soft polymer or may be comprise an atraumatic, rounded distal end. The distal portion of elongate tube 922 comprises a navigation marker such as a radiopaque marker band 926. In one embodiment, radiopaque marker band 926 is made of a platinum-iridium alloy. The proximal end of elongate tube 922 comprises a hub 928. In one embodiment, hub 928 is a female luer hub. A portion of strain relief tubing 930 may be provided between hub 928 and elongate tube 922. In one embodiment, the proximal portion of sheath device 920 comprises a rotating hemostasis valve device such as a Touhy-Borst device to lock down a guidewire being introduced through sheath device 920. This enables sheath device 920 and the guidewire to be controlled as one unit. Sheath device 920 may be used for exchanging guidewires, lavage or suction of anatomical regions etc. Sheath device 920 may also be used to redirect guide wires during guide wire probing. Other uses of sheath device 920 include, but are not limited to, introduction and support of various interventional and diagnostic devices when performing procedures such as sinus ostia dilation, sinus lavage, and suction. Sheath device 920 may also be used to perform other diagnostic or therapeutic procedures including, but not limited to treatment of middle ear diseases or disorders via the Eustachian tube. The system shown in FIGS. 9A through 9D may comprise more than one sheath device.

FIG. 9D shows a side view of a balloon catheter. Balloon catheter 934 comprises an elongate shaft 936. Elongate shaft 936 may be made from suitable biocompatible polymers including, but not limited to Nylon, Pebax, polyethylene, etc. Distal portion of elongate shaft 936 may comprise one or more radiopaque marker bands. The catheter also has one marker on the proximal shaft which indicates approximately the exit of the balloon proximal bond from the distal end of the guiding catheter. Elongate shaft 936 comprises a balloon inflation lumen for inflating or deflating a balloon 938 located on the distal portion of elongate shaft 936. Balloon 938 may be a compliant or non-compliant balloon. Balloon 938 is designed to provide an inflatable segment of known diameter and length at recommended inflation pressures. In one embodiment, balloon 938 is a non-compliant balloon made of PET. In one embodiment, elongate shaft 936 further comprises a guidewire lumen. The guidewire lumen may be coaxial to the balloon inflation lumen. The guidewire lumen may be variously designed to enable passage of one or more guidewires such as guidewire 910 may be inserted through the guidewire lumen. In an alternate embodiment, balloon catheter 934 comprises a fixed guidewire 940 such that the distal end of fixed guidewire 940 forms the distal end of balloon catheter 934. Fixed guidewire 940 may be used for navigation balloon catheter 934 through the anatomy. In the embodiment of balloon catheter 934 shown in FIG. 9D, the proximal end of balloon catheter comprises a 'Y' connector 942. The proximal end of 'Y' connector 942 comprises a first luer port 944 that leads to a guidewire lumen in balloon catheter 934. In one embodiment, the region of guide device around first luer port 944 comprises a rotating hemostasis valve device such as a Touhy-Borst device to lock down a guidewire being introduced through first luer port 944. This enables balloon catheter 934 and guidewire 910 to be controlled as one unit. 'Y' connector 942 further comprises a second luer port 946 that is in fluid communication with the balloon inflation lumen in balloon catheter 934. Balloon 938 is inflated by injecting a suitable inflation medium such as diluted contrast solution through second luer port 946. In one embodiment, proximal portion of elongate shaft 936 comprises a visual marker. The visual marker is used to verify relative location of balloon 938 relative to distal end of guide device 900 when balloon catheter 934 is used introduced through guide device 900. The visual marker completely enters proximal end of guide device 900 when material of balloon 938 completely exits the distal end of guide device 900. Thus, erroneous inflation of balloon 938 within guide device 900 can be prevented. Balloon catheter 934 can be used to dilate anatomical regions such as ostia and spaces within the paranasal sinus cavities for diagnostic and therapeutic procedures. The system shown in FIGS. 9A through 9D may comprise more than one balloon catheter.

The system in FIGS. 9A through 9D can be used to treat anatomical regions such as paranasal sinuses, ostia or passageways leading to paranasal sinuses, etc. In one embodiment of a method of treating sinusitis by dilating an opening in a paranasal sinus, a suitable guide device 900 is inserted through the nose. Guide device 900 is then advanced such that the distal end of guide device 900 is located near the opening (e.g., any transnasally accessible opening in a paranasal sinus or air cell including but not limited to; natural ostia, surgically altered natural ostia, surgically created openings, antrostomy openings, ostiotomy openings, burr holes, drilled holes, ethmoidectomy openings, natural or man made passageways, etc.) of interest. The step of advancement of guide device 900 may be performed under endoscopic visualization. An initial endoscopic examination may also be performed before introducing guide device 900 through the nose. The exact location of the distal end of guide device 900 depends on the sinus to be accessed. To access a maxillary, frontal or anterior Ethmoid sinus, the distal tip of guide device 900 is placed under the middle turbinate just beyond the uncinate process. To access an Ethmoid sinus in patients with an intact middle turbinate, guide device 900 is placed lateral to the middle turbinate. To access a sphenoid or posterior Ethmoid sinus, the distal tip of guide device 900 is passed posteriorly, medial to the middle turbinate. To treat a patient who has already undergone a FESS, sphenoid sinuses may be accessed by advancing guide device 900 through what used to be the bulla, lateral to the middle turbinate.

Thereafter, a suitable guidewire 910 is introduced through guide device 900 such that the distal end of guidewire 910 emerges out of the distal end of guide device 900. Guidewire 910 is then used to access an opening of a paranasal sinus ((e.g., any transnasally accessible opening in a paranasal sinus or air cell including but not limited to; natural ostia, surgically altered natural ostia, surgically created openings, antrostomy openings, ostiotomy openings, burr holes, drilled holes, ethmoidectomy openings, natural or man made passageways, etc.). If guidewire 910 encounters substantial resistance, guidewire 910 is retracted, the position of guidewire 910 is slightly changed and the access of the opening of the paranasal sinus is retried. An optional torque device may be placed on guidewire 910 during the step of accessing the opening of the paranasal sinus if more guidewire torque control and steerability is desired. The position of guide device 900 and guidewire 910 can be tracked with fluoroscopy. Successful access of the sinus opening of the paranasal sinus is marked by smooth easy passage of guidewire 910 into and beyond theopening of the paranasal sinus. Thereafter, guidewire 910 may be passed into the sinus until some light resistance is felt or approximately 2-7 cm of the distal portion of guidewire 910 is inside the sinus. The position of guidewire 910 can be confirmed with fluoroscopy.

Thereafter, a suitable balloon catheter 934 is passed over guidewire 910 through guide device 900, into the opening of the paranasal sinus. Thereafter, balloon catheter 934 is positioned across a target region to be dilated. The position of balloon catheter 934 may be confirmed using fluoroscopy and/or endoscopy.

Thereafter, an inflation device is used to inflate balloon 938 with gradually increasing pressure. During the step of inflating balloon 938, the diameter, shape and position of the balloon can be tracked using fluoroscopy and/or endoscopy. Balloon 938 is further inflated until balloon 938 becomes fully expanded. Care is taken during the step of inflating balloon 938 to ensure that the pressure in balloon 938 does not exceed a maximum allowed pressure. After balloon 938 is fully expanded, the pressure created by the inflation device is released. A vacuum is then applied by the inflation device to deflate balloon 938.

Thereafter, guide device 900, guidewire 910 and balloon catheter 934 are removed together as one unit. The dilation of the opening of the paranasal sinus can be determined using endoscopy.

Several variations of the abovementioned procedure are possible. In one method embodiment, guidewire 910 is preloaded into guide device 900. Guidewire 910 and guide device 900 are then co-introduced into the anatomy such that the distal tip of guide device 900 is located near a target region of the anatomy. In another method embodiment, balloon catheter 934 is preloaded over guidewire 910. The combination of balloon catheter 934 and guidewire 910 is in turn preloaded inside of guide device 900. This combination of balloon catheter 934, guidewire 910 and guide device 900 can be introduced in the nasal cavity such the distal end of the combination is positioned near a desired target region. Thereafter, guidewire 910 is advanced into the desired target region such as a sinus cavity. Thereafter, balloon catheter 934 is advanced over guidewire 910. Balloon 938 is then inflated to dilate an anatomical region.

Balloons of different diameters may be used for dilating the same region of the target anatomy. The target anatomy may be pre-dilated before dilating the target anatomy by balloon 938. This step is performed by using a balloon catheter with a balloon of a diameter smaller than the diameter of balloon 938. The target anatomy may be re-dilated after dilating the target anatomy by balloon 938. This step is performed by using a balloon catheter with a balloon of a diameter larger than the diameter of balloon 938. The steps of pre-dilation or re-dilation can be performed by inserting one or more additional balloon catheters over the guidewire used to insert balloon catheter 934. The steps of pre-dilation or re-dilation may be repeated using multiple balloon catheters if desired.

Balloon catheter 934 may be used to dilate multiple regions of the anatomy. This method embodiment is especially useful for optimal dilation of a longer passageway. In this technique, the balloon is positioned in one location, inflated, and then deflated. Instead of retracting the balloon completely, it is simply repositioned to the new location by advancing or retracting it over the guidewire while keeping the guide and the guidewire in place. The balloon is then re-inflated and deflated. This process can be repeated multiple times until the entire passageway has been dilated as desired. This may also be employed as a means of predilating the opening of the paranasal sinus to allow subsequent passage of the balloon catheter. Balloon catheter 934 may be used to break or crack a bony region in an opening of a paranasal sinus ((e.g., any transnasally accessible opening in a paranasal sinus or air cell including but not limited to; natural ostia, surgically altered natural ostia, surgically created openings, antrostomy openings, ostiotomy openings, burr holes, drilled holes, ethmoidectomy openings, natural or man made passageways, etc.) or other anatomical structure where bone is substantially covered by mucosal tissue. The breaking or cracking of the bony region may be indicated by a sudden drop in a pressure gauge located on the inflation device. The breaking or cracking of the bony region may also be accompanied by an audible sound. The sudden drop in pressure or the audible sound can be used as feedback of the success of the step of breaking or cracking of the bony region.

A sinus seeker such as a maxillary sinus seeker, frontal sinus seeker etc. may be used to locate an opening into a paranasal sinus (e.g., any transnasally accessible opening in a paranasal sinus or air cell including but not limited to; natural ostia, surgically altered natural ostia, surgically created openings, antrostomy openings, ostiotomy openings, burr holes, drilled holes, ethmoidectomy openings, natural or man made passageways, etc.) and/or to plan a trajectory for introducing one or more devices disclosed herein. The sinus seeker may be used before or after the step of insertion of devices such as guide device 900, guidewire 910, sheath device 920, balloon catheter 934, etc.

Endoscope(s) may be used to monitor and/or guide one or more steps of the various methods disclosed herein. For example, an endoscope maybe used to direct guidewire 910 into various ostia or ducts or passageways to ensure proper placement of guidewire 910. Distal portions of one or more devices disclosed herein may be of a suitable color to enable the one or more devices to be visualized by the endoscope. A combination of endoscopic visualization and fluoroscopic visualizations may be used to monitor and/or guide one or more steps of the various methods disclosed herein.

A sheath device such as sheath device 920 may be used to provide further support and direction during the placement of guidewire 910. In one method embodiment, sheath device 920 is introduced through guide device 900 such that the distal tip of sheath device 920 is closer to the target region than the distal tip of guide device 900. Thereafter, guidewire 910 is introduced through sheath device 920. Thereafter, sheath device 920 is retracted while keeping guidewire 910 in place. Balloon catheter 934 is then inserted over guidewire 934 and the opening of the paranasal sinus is dilated. In one embodiment, after the opening of the paranasal sinus is dilated, balloon 938 is deflated. Thereafter, only balloon catheter 934 is removed from the anatomy while keeping guidewire 910 and guide device 900 in place. Thereafter, sheath device 920 is inserted through guide device 900 over guidewire 910 into the sinus. Guidewire 910 is then retracted completely and alternate suction and irrigation are employed to drain the sinus of any puss, tissue or fluids that may reside within the cavity. In another method embodiment, balloon catheter 934 is used to provide irrigation with or without some limited suction of low viscosity fluids. This is done after the dilation step by keeping balloon catheter 934 in the anatomy, removing guidewire 910 and then irrigating/suctioning through guidewire lumen of balloon catheter 934.

Figure 10:
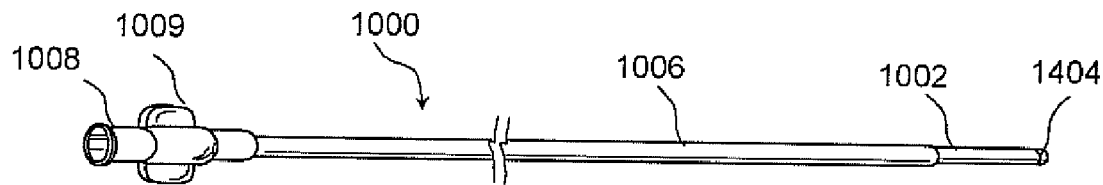
FIG. 10A is a side view of a tubular guide device of the present invention having a straight distal portion.
FIG. 10B is a side view of a tubular guide device of the present invention having a 30 degree curve in its distal portion.
FIG. 10C is a side view of a tubular guide device of the present invention having a 70 degree curve in its distal portion.
FIG. 10D is a side view of a tubular guide device of the present invention having a 90 degree curve in its distal portion.
FIG. 10E is a side view of a tubular guide device of the present invention having a 110 degree curve in its distal portion.
FIG. 10F is a sectional view of the distal end of an embodiment of a tubular guide device of the present invention.
FIG. 10G is a sectional view of the distal end of another embodiment of a tubular guide device of the present invention.
Figure 10:
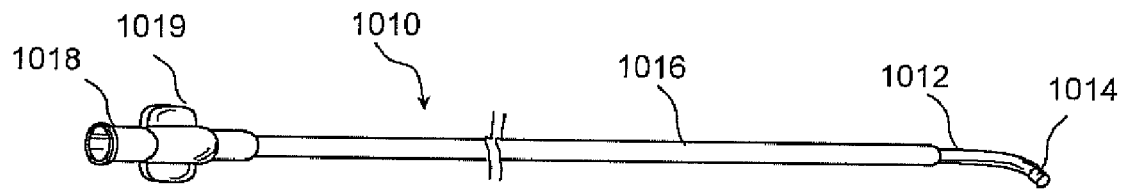
Figure 10:
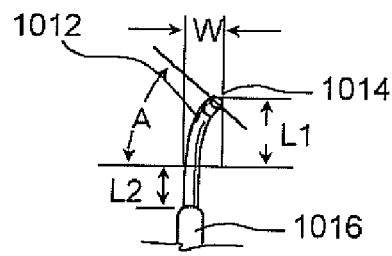
Figure 10:
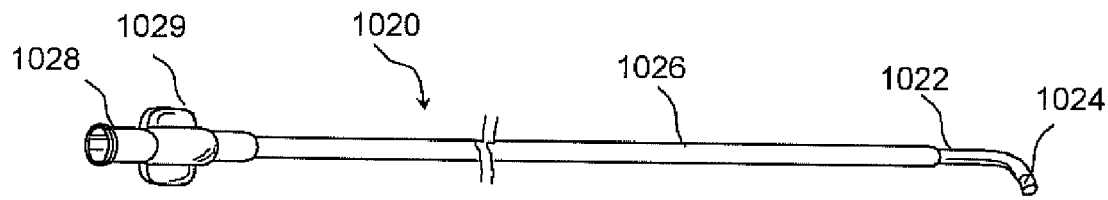
Figure 10:
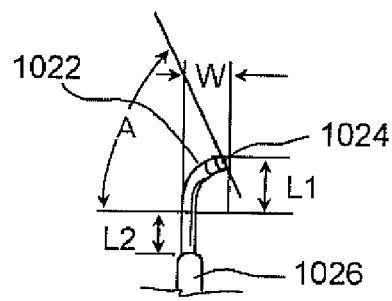
Figure 10:
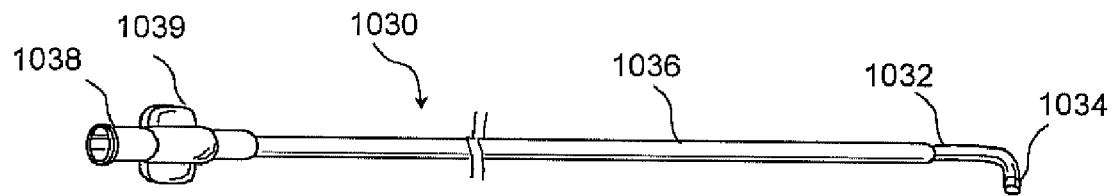
Figure 10:
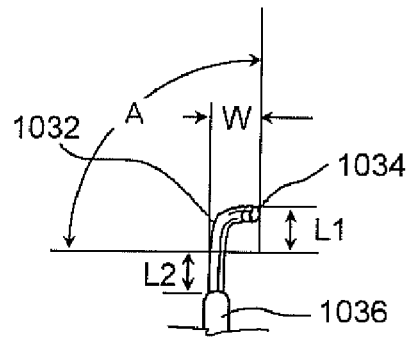
Figure 10:
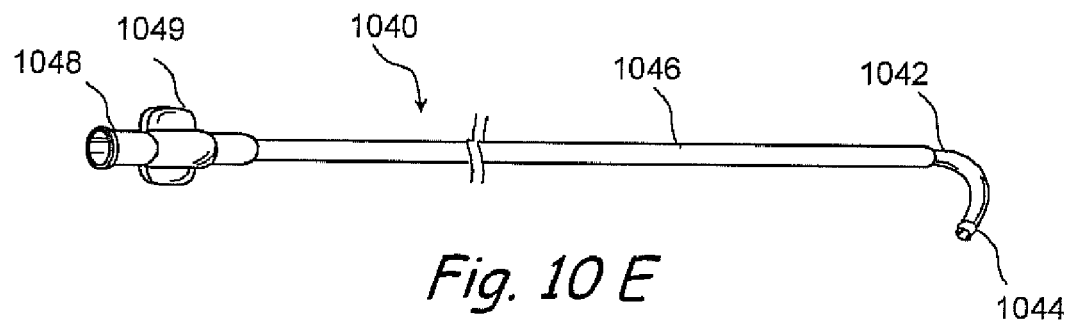
Figure 10:
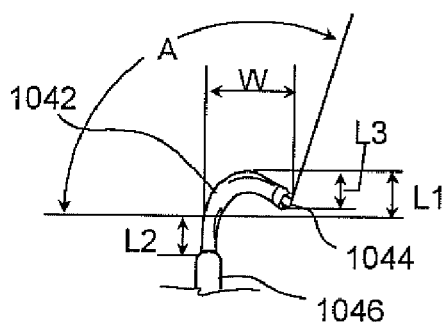
Figure 10:
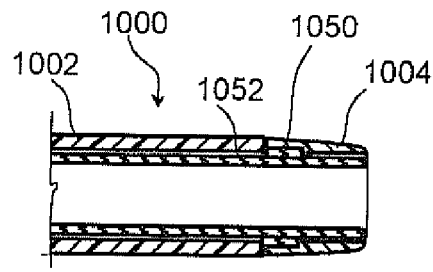
Figure 10:
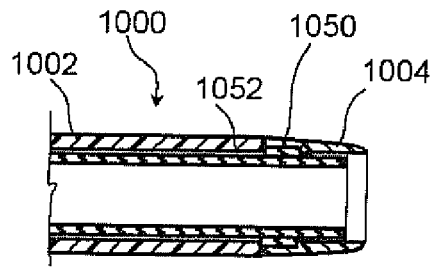

FIGS. 10A through 10E' show side views of embodiments of guide devices. One or more of these guide devices may be provided as a part of the system shown in FIGS. 9A through 9D. FIG. 10A shows a side view of a first embodiment of a guide device comprising a substantially straight distal portion. Guide device 1000 comprises an elongate tube 1002. Elongate tube 1002 may be made of suitable biocompatible materials such polymers e.g. Nylon, Pebax, etc. In a preferred embodiment, the material of elongate tube 1002 has Rockwell hardness in the range of about 70R to about 110R. In this preferred embodiment, the distal portion is flexible enough to prevent or reduce damage to the anatomy. Yet, the distal portion is rigid enough to retain its shape as one or more devices are passed through guide device 900. Furthermore, the distal portion is rigid enough to enable a user to use the distal portion to displace anatomical structures. The distal portion of elongate tube 1002 comprises a curved, bent or angled region curved at an angle of less then 5 degrees. In one embodiment, distal portion of elongate tube 1002 is substantially straight. The inner surface of elongate tube 1002 may be lined by a lubricious coating or a tubular lubricious liner made of a suitable biocompatible material such as PTFE. In one embodiment, the outer diameter of elongate tube 1002 is around 0.134+/−0.005 inches. The distal portion of elongate tube 1002 comprises an atraumatic tip 1004. Atraumatic tip 1004 may be made of suitable biocompatible materials including, but not limited to Pebax, etc. Atraumatic tip 1004 prevents or reduces damage to the anatomy caused by the distal end of guide device 1000. In one embodiment, length of atraumatic tip 1004 is 0.08+/−0.04 inches and the material of tip 1004 has Shore Durometer hardness in the range of about 35D to about 72D. Guide device 1000 further comprises a hypotube 1006. Hypotube 1006 may be made of suitable biocompatible materials such as stainless steel 304, titanium, Nitinol, polymers such as Nylon etc. In one embodiment, the outer diameter of hypotube 1006 is 0.154+/−0.005 inches. In one embodiment of a method of constructing guide device 1000, a stainless steel hypotube 1006 is bonded to an elongate tube 1002 such as a Nylon elongate tube 1002 to increase the strength of elongate tube 1002. In one embodiment, hypotube 1006 is heat bonded to elongate tube 1002. One or more openings, perforations or holes may be located on hypotube 1006 to enable material of elongate tube 1002 to melt into the one or more openings, perforations or holes. When the melted material of elongate tube 1002 solidifies, an additional mechanical bonding is created between hypotube 1006 and elongate tube 1002. The proximal end of guide device 1000 comprises a hub 1008. In one embodiment, hub 1008 is a female luer hub. Hub 1008 may have wings 1009 to enable a user to turn guide device 1000. In one embodiment, the axial length of guide device 1000 is 5+/−0.25 inches. In one embodiment, the inner diameter of guide device 1000 is around 0.1 inches. The distal portion of guide device 1000 may comprise a radiopaque marker. In one embodiment, the radiopaque marker is a platinum/iridium marker band. The guide device design shown in FIG. 10A is especially suited for trans-nasal access of the sphenoid sinuses.

FIG. 10B shows a side view of a first embodiment of a guide device comprising a bent, angled or curved distal portion. Guide device 1010 comprises an elongate tube 1012. Elongate tube 1012 may be made of suitable biocompatible materials such polymers e.g. Nylon, Pebax, etc. Elongate tube 1012 comprises a substantially straight proximal portion enclosed by a hypotube and a distal portion comprising a curved, bent or angled region. The angle of the curved, bent or angled region of the distal portion can range from 5 degrees to 45 degrees. In this embodiment, distal portion of elongate tube 1012 is bent by an angle of around 30 degrees. The inner surface of elongate tube 1012 may be lined by a lubricious coating or a tubular lubricious liner made of a suitable biocompatible material such as PTFE. In one embodiment, the outer diameter of elongate tube 1012 is around 0.134+/−0.005 inches. The distal portion of elongate tube 1012 comprises an atraumatic tip 1014. Atraumatic tip 1014 may be made of suitable biocompatible materials including, but not limited to Pebax, etc. Atraumatic tip 1014 prevents or reduces damage to the anatomy caused by the distal end of guide device 1010. In one embodiment, length of atraumatic tip 1014 is 0.08+/−0.04 inches. Guide device 1010 further comprises a hypotube 1016 covering the proximal portion of elongate tube 1012. Hypotube 1016 may be made of suitable biocompatible materials such as stainless steel 304, titanium, Nitinol, polymers such as Nylon etc. In one embodiment, the outer diameter of hypotube 1016 is 0.154+/−0.005 inches. In one embodiment of a method of constructing guide device 1010, a stainless steel hypotube 1016 is bonded to a Nylon elongate tube 1012. The proximal end of guide device 1010 comprises a hub 1018. In one embodiment, hub 1018 is a female luer hub. Hub 1018 may have wings 1019 to enable a user to turn guide device 1010. Wings 1019 may be aligned in the plane of the curve of the distal tip as an indicator of the position and orientation of the distal tip in the anatomy. In one embodiment, the axial length of guide device 1010 is 5+/−0.25 inches. In one embodiment, the inner diameter of guide device 1010 is around 0.1 inches. The distal portion of guide device 1010 may comprise a radiopaque marker. In one embodiment, the radiopaque marker is a platinum/iridium marker band. FIG. 10B' shows an enlarged view of the distal portion of the guide device in FIG. 10B. FIG. 10B' shows elongated tube 1012 enclosed by hypotube 1016. Distal end of elongated tube 1012 comprises atraumatic tip 1014. Several parameters defined hereafter characterize the design of the distal portion of guide device 1010. The width of the distal end of guide device 1010 is called W as shown. The length measured from the proximal-most point on the distal curved portion of elongate tube 1012 to the distal tip is called L1. L1 is measured along the linear direction of the straight proximal portion of guide device 1010 as shown in FIG. 10B'. The length of the straight region of elongate tube 1012 from the distal end of the proximal portion till the proximal most point on the curved region of the distal portion is called L2. In one particular embodiment, W is 0.34+/−0.08 inches, L1 is 0.46+/−0.08 inches, L2 is 0 to 2 inches and the radius of curvature of the distal curved region of elongate tube 1012 is 0.180 inches. The guide device design shown in FIGS. 10B and 10B' is especially suited for trans-nasal access of the sphenoid sinuses.

FIG. 10C shows a side view of a second embodiment of a guide device comprising a bent, angled or curved distal portion. The design of guide device 1020 is similar to the design of guide device 1010. Guide device 1020 comprises an elongate tube 1022. The distal portion of elongate tube 1022 comprises a curved, bent or angled region curved at an angle ranging from 30 degrees to 100 degrees. In this embodiment, distal portion of elongate tube 1022 is bent by an angle of around 70 degrees. The distal portion of elongate tube 1022 comprises an atraumatic tip 1024. Guide device 1020 further comprises a hypotube 1026. The proximal end of guide device 1020 comprises a hub 1028. In one embodiment, hub 1028 is a female luer hub. Hub 1028 may have wings 1029 to enable a user to turn guide device 1020. FIG. 1C' shows an enlarged view of the distal portion of the guide device in FIG. 10C. FIG. 1C' shows elongated tube 1022 enclosed by hypotube 1026. Distal end of elongated tube 1022 comprises atraumatic tip 1024. In one particular embodiment, W is 0.45+/−0.08 inches, L1 is 0.32+/−0.08 inches, L2 is 0 to 2 inches and the radius of curvature of the distal curved region of elongate tube 1022 is 0.180 inches. The guide device design shown in FIGS. 10C and 10C' is especially suited for trans-nasal access of the frontal sinuses.

FIG. 10D shows a side view of a second embodiment of a guide device comprising a bent, angled or curved distal portion. The design of guide device 1030 is similar to the design of guide device 1010. Guide device 1030 comprises an elongate tube 1032. The distal portion of elongate tube 1032 comprises a curved, bent or angled region curved at an angle ranging from 70 degrees to 135 degrees. In this embodiment, distal portion of elongate tube 1032 is bent by an angle of around 90 degrees. The distal portion of elongate tube 1032 comprises an atraumatic tip 1034. Guide device 1030 further comprises a hypotube 1036. The proximal end of guide device 1030 comprises a hub 1038. In one embodiment, hub 1038 is a female luer hub. Hub 1038 may have wings 1039 to enable a user to turn guide device 1030. FIG. 10D' shows an enlarged view of the distal portion of the guide device in FIG. 10D. FIG. 10D' shows elongated tube 1032 enclosed by hypotube 1036. Distal end of elongated tube 1032 comprises atraumatic tip 1034. In one particular embodiment, W is 0.39+/−0.080 inches, L1 is 0.25+/−0.08 inches, L2 is 0 to 2 inches and the radius of curvature of the distal curved region of elongate tube 1032 is 0.180 inches. W may be as small as 5 mm with a corresponding reduction in the radius of curvature of the distal curved region of elongate tube 1032. The guide device design shown in FIGS. 10D and 10D' is especially suited for trans-nasal access of the maxillary sinuses.

FIG. 10E shows a side view of a second embodiment of a guide device comprising a bent, angled or curved distal portion. The design of guide device 1040 is similar to the design of guide device 1010. Guide device 1040 comprises an elongate tube 1042. The distal portion of elongate tube 1042 comprises a curved, bent or angled region curved at an angle ranging from 100 degrees to 120 degrees. In this embodiment, distal portion of elongate tube 1042 is bent by an angle of around 110 degrees. The distal portion of elongate tube 1042 comprises an atraumatic tip 1044. Guide device 1040 further comprises a hypotube 1046. The proximal end of guide device 1040 comprises a hub 1048. In one embodiment, hub 1048 is a female luer hub. Hub 1048 may have wings 1049 to enable a user to turn guide device 1040. FIG. 10E' shows an enlarged view of the distal portion of the guide device in FIG. 10E. FIG. 10E' shows elongated tube 1042 enclosed by hypotube 1046. Distal end of elongated tube 1042 comprises atraumatic tip 1044. In one particular embodiment, W is 0.46+/−0.08 inches, L1 is 0.25+/−0.08 inches, L2 is 0 to 0.5 inches and the radius of curvature of the distal curved region of elongate tube 1042 is 0.180 inches. L1 and W may be smaller than 0.25+/−0.08 inches and 0.46+/−0.08 inches respectively. The guide device design shown in FIGS. 10E and 10E' is especially suited for trans-nasal access of the maxillary sinuses.

FIG. 10F shows a partial longitudinal sectional view through the plane 10-10 in FIG. 10A showing a first embodiment of the distal tip of a guide device. Distal portion of guide device 1000 comprises elongate tube 1002. Distal portion of elongate tube 1002 has an atraumatic tip 1004. In this embodiment, the distal edge of atraumatic tip 1004 has a tapered distal edge to reduce tissue injury due to guide device 1000. Guide device 1000 further comprises a radiographic marker band 1050. In this embodiment, marker band 1050 is located on the inner surface of atraumatic tip 1004. Guide device 1000 further comprises a lubricious liner 1052 located on the inner surface of guide device 1000.

FIG. 10G shows a partial longitudinal sectional view through the plane 10-10 in FIG. 10A showing a second embodiment of the distal tip of a guide device. Distal portion of guide device 1000 comprises elongate tube 1002. Distal portion of elongate tube 1002 has an atraumatic tip 1004. In this embodiment, the distal edge of atraumatic tip 1004 has a rounded distal edge to reduce tissue injury due to guide device 1000. Guide device 1000 further comprises a radiographic marker band 1050. In this embodiment, marker band 1050 is located on the inner surface of atraumatic tip 1004. Guide device 1000 further comprises a lubricious liner 1052 located on the inner surface of guide device 1000.

Figure 11:
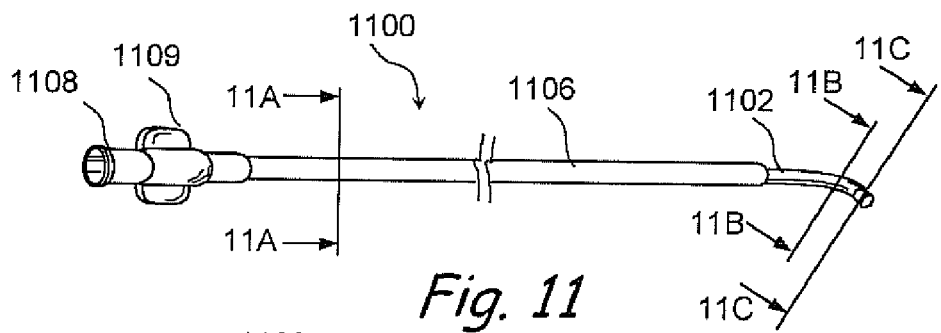
FIG. 11 is a perspective view of a tubular guide device of the present invention.
Figure 11:
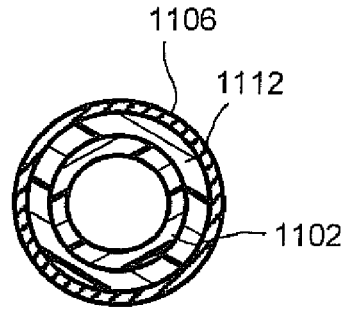
Figure 11:
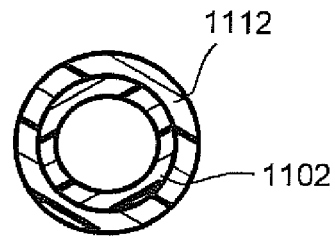
Figure 11:
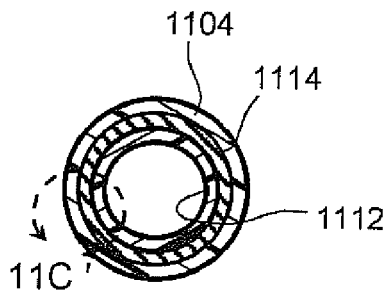
Figure 11:
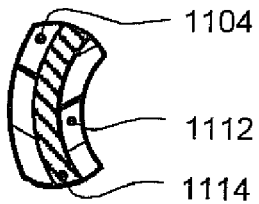

FIG. 11 shows a perspective view of an embodiment of a guide device. Guide device 1100 comprises an elongate tube 1102. The distal portion of elongate tube 1102 comprises a curved, bent or angled region. The distal portion of elongate tube 1102 comprises an atraumatic tip 1104. Guide device 1100 further comprises a hypotube 1106. The proximal end of guide device 1100 comprises a hub 1108. In one embodiment, hub 1108 is a female luer hub. Hub 1108 may have wings 1110 to enable a user to torque guide device 1100. FIG. 11A shows a cross sectional view through line 11A-11A of FIG. 11. FIG. 11A shows a cross section of guide device 1100 showing elongate tube 1102 surrounded by hypotube 1106. In this embodiment, inner surface of elongate tube 1106 is lined by a lubricious coating or a lubricious liner 1112. Lubricious liner 1112 may be made of suitable biocompatible materials such as PTFE. FIG. 11B shows a cross sectional view through line 11B-11B of FIG. 11. FIG. 11B shows a cross section of guide device 1100 showing elongate tube 1102. In this embodiment, inner surface of elongate tube 1106 is lined by a lubricious coating or a lubricious liner 1112. FIG. 11C shows a cross sectional view through line 11C-11C of FIG. 11. FIG. 11C shows a cross section of guide device 1100 showing atraumatic tube 1104 enclosing a radiographic marker band 1114. In this embodiment, inner surface of guide device 1100 is lined by a lubricious coating or a lubricious liner 1112. FIG. 11C' shows an enlarged view of region 11C' in FIG. 11C showing atraumatic tube 1104 enclosing radiographic marker band 1114 and lubricious liner 1112.

Figure 12:
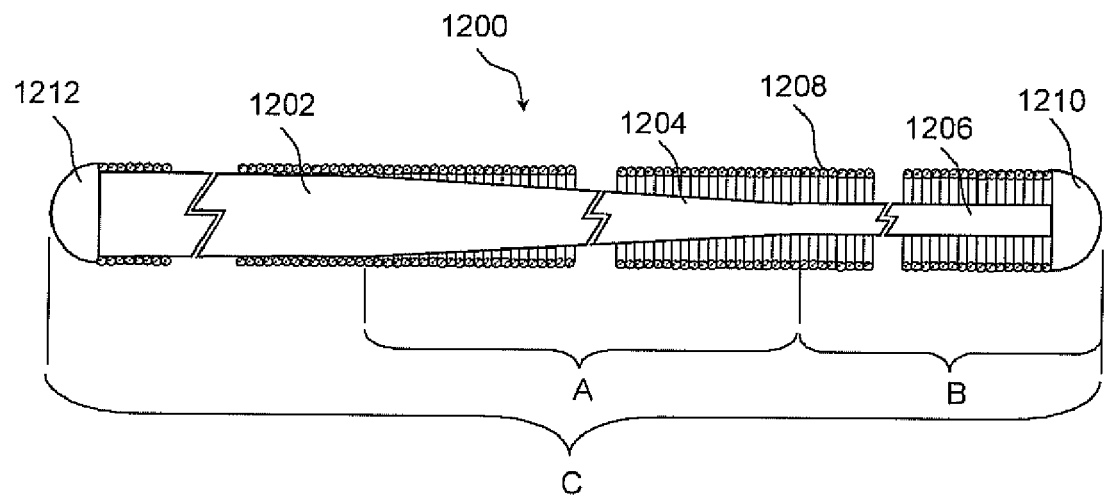
FIG. 12 is a longitudinal sectional view of a guidewire device of the present invention.

FIG. 12 shows a longitudinal sectional view of a guidewire. Guidewire 1200 is a flexible guidewire comprising a core wire comprising a proximal portion 1202, a middle portion 1204 and a distal portion 1206. In one embodiment, proximal portion 1202 and distal portion 1206 are substantially cylindrical with the diameter of proximal portion 1202 greater than the diameter of distal portion 1206. This causes the distal portion of guidewire 1200 to be substantially floppy. In one embodiment, the length of the floppy region is about 20 cm. Middle portion comprises a tapered shape. The core wire can be made of suitable biocompatible materials such as stainless steel, Nitinol, etc. Guidewire 1200 further comprises an outer coil 1208. Outer coil 1208 may be made of suitable biocompatible materials including, but not limited to stainless steel. Outer coil 1208 is connected to the core wire at the distal end of guidewire 1200 by a smooth, burr free soldered or welded distal joint 1210 to get an atraumatic distal tip. Similarly, outer coil 1208 is connected to the core wire at the proximal end of guidewire 1200 by a smooth, burr free soldered or welded proximal joint 1212 to get an atraumatic proximal tip. Guidewire 1200 may further comprise an inner coil located on the distal portion of guidewire 1200 enclosed by outer coil 1208. The inner coil may be made of suitable radiopaque materials to allow visualization of the distal portion of guidewire 1200 under fluoroscopy. In one particular embodiment, the inner coil is made of an alloy of 92% platinum and 8% tungsten. A part or the entire outer surface of guidewire 1200 may comprise a lubricious coating such as a PTFE coating. In one embodiment, the length A of middle portion 1204 is about 16.5 cm, length B of distal portion 1206 is about 7 cm and the total length C of guidewire 1200 is about 75 cm. In another embodiment, the length A of middle portion 1204 is about 17 cm, length B of distal portion 1206 is about 7 cm and the total length C of guidewire 1200 is about 120 cm. In another embodiment, the length A of middle portion 1204 is about 13 cm, length B of distal portion 1206 is about 11 cm and the total length C of guidewire 1200 is about 120 cm. In one embodiment, the diameter of guidewire 1200 is about 0.035 inches. Various designs of guidewire 1200 may be used to design guidewire 910 in FIG. 9B. Multiple guidewires with various design parameters such as outer diameter, stiffness, length may be supplied as a part of a system such as the system shown in FIGS. 9A through 9D. Guidewire 1200 may be used to access various regions in the anatomy. It can be used to facilitate placement of other devices during various diagnostic or therapeutic procedures. Guidewire 1200 may be torquable to facilitate navigation of guidewire 1200 especially through tortuous anatomy. Specific uses of guidewire 1200 include, but are not limited to introduction and support of various diagnostic or therapeutic devices for performing procedures such as sinus ostia dilation, lavage of anatomical spaces such as paranasal sinuses, suction, etc. Another specific use of guidewire 1200 is introduction of devices for treatment of the middle ear via the Eustachian tube. A portion of the distal end of guidewire 1200 may be introduced into a paranasal sinus so that the portion of guidewire 1200 is coiled inside the paranasal sinus. This enables a user to estimate the contour of the paranasal sinus.

Figure 13:
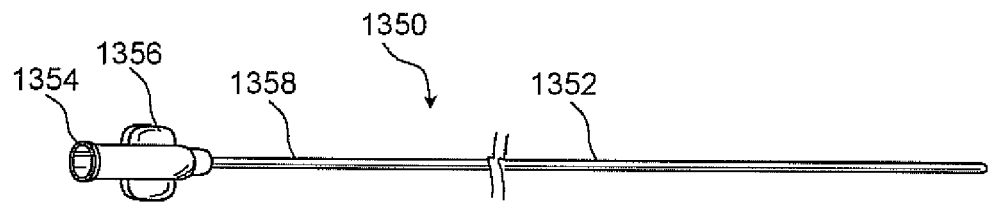
FIG. 13A is a perspective view of an embodiment of a tubular sheath of the present invention.
FIG. 13B is a perspective view of another embodiment of a tubular sheath of the present invention.
Figure 13:
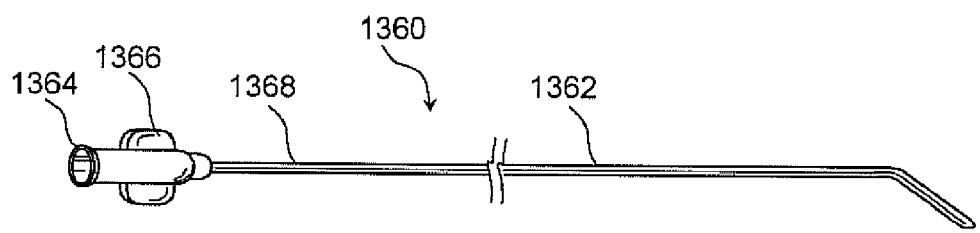

FIG. 13A shows an embodiment of a sheath device comprising a substantially straight distal end. Sheath device 1350 comprises a flexible elongate shaft 1352. Elongate shaft 1352 is substantially straight and comprises a lumen. Elongate shaft 1352 may be made of suitable biocompatible materials including, but not limited to polyethylene, Nylon, etc. In one embodiment, elongate shaft 1352 comprises a stiffening means including, but not limited to metal braids or coils, polymer jackets, etc. In another embodiment, stiffness of elongate shaft 1352 is increased by crosslinking material of elongate shaft 1352 by exposing it to an electron beam. Distal end of elongate shaft 1352 may comprise an atraumatic tip made of a soft polymer or a radiused tip. Distal portion of elongate shaft 1352 may also comprise a radiopaque marker such as a platinum-iridium radiographic marker to enable visualization of the distal portion of elongate shaft 1352 under fluoroscopy. The inner surface of elongate shaft may be lined with a lubricious coating or a lubricious inner liner. The proximal end of elongate shaft 1352 comprises a hub 1354. In one embodiment, hub 1354 is a female luer hub. Hub 1354 comprises one or more wings 1356 that are used by a user to torque sheath device 1350. A strain relief tubing 1358 may be provided between hub 1354 and elongate shaft 1352. Strain relief tubing 1358 may be made of suitable biocompatible materials such as polyimide. Sheath device 1350 may be made in various sizes and shapes to facilitate access to various anatomical regions such as various paranasal sinuses and passageways and openings leading to the paranasal sinuses. In an embodiment, the effective length of sheath device 1350 is 29+/−1 cm, the outer diameter of elongate shaft 1352 is 0.052+/−0.003 inches, and inner diameter of elongate shaft 1352 is 0.040+/−0.003 inches. Such a device is compatible with guide devices of an inner diameter greater than 0.056 inches. Such a device is especially suited for lavaging an anatomical region. In another embodiment, the effective length of sheath device 1350 is 35+/−2 cm, the outer diameter of elongate shaft 1352 is 0.059+/−0.002 inches, and inner diameter of elongate shaft 1352 is 0.039+/−0.001 inches Such a device is compatible with guide devices of an inner diameter greater than 0.065 inches. Such a device is especially suited for suctioning an anatomical region, exchanging elongate devices, supporting the introduction or removal of elongate devices, etc. In another embodiment, the effective length of sheath device 1350 is 22+/−1 cm, the outer diameter of elongate shaft 1352 is 0.088+/−0.002 inches, and inner diameter of elongate shaft 1352 is 0.065+/−0.001 inches. Such a device is compatible with guide devices of an inner diameter greater than 0.097 inches. Such a device is especially suited for suctioning an anatomical region, supporting the introduction of thinner elongate devices, etc.

FIG. 13B shows another embodiment of a sheath device comprising a bent, curved or angled distal end. Design of sheath device 1360 is substantially similar to design of sheath device 1350. Sheath device 1360 comprises a flexible elongate shaft 1362. The distal portion of elongate shaft 1362 comprises a bent, curved or angled region to facilitate access to various anatomical regions such as various paranasal sinuses and passageways and openings leading to the paranasal sinuses. In one embodiment, distal portion of elongate shaft 1362 comprises a bent region bent by an angle of around 30 degrees. In another embodiment, distal portion of elongate shaft 1362 comprises a bent region bent by an angle of around 45 degrees. The proximal end of elongate shaft 1362 comprises a hub 1364. In one embodiment, hub 1364 is a female luer hub. Hub 1364 comprises one or more wings 1366 that are used by a user to torque sheath device 1360. Wings 1366 may be aligned in the plane of the bent, curved or angled region of the elongate shaft 1362. A strain relief tubing 1368 may be provided between hub 1364 and elongate shaft 1362. In an embodiment, the effective length of sheath device 1360 is 29+/−1 cm, the outer diameter of elongate shaft 1362 is 0.052+/−0.003 inches, and inner diameter of elongate shaft 1362 is 0.040+/−0.003 inches. Such a device is compatible with guide devices of an inner diameter greater than 0.056 inches. Such a device is especially suited for lavaging an anatomical region. In another embodiment, the effective length of sheath device 1360 is 35+/−2 cm, the outer diameter of elongate shaft 1362 is 0.059+/−0.002 inches, and inner diameter of elongate shaft 1362 is 0.039+/−0.001 inches Such a device is compatible with guide devices of an inner diameter greater than 0.065 inches. Such a device is especially suited for suctioning an anatomical region, exchanging elongate devices, supporting the introduction or removal of elongate devices, etc. In another embodiment, the effective length of sheath device 1360 is 22+/−1 cm, the outer diameter of elongate shaft 1362 is 0.088+/−0.002 inches, and inner diameter of elongate shaft 1362 is 0.065+/−0.001 inches. Such a device is compatible with guide devices of an inner diameter greater than 0.097 inches. Such a device is especially suited for suctioning an anatomical region, supporting the introduction of thinner elongate devices, etc.

Sheath device 1350 and sheath device 1360 can be used as a part of the system shown in FIGS. 9A through 9D. The sheath devices disclosed herein can be used for lavage, suction, and exchange of wires in anatomical regions such as the paranasal sinuses. The sheath devices may also be used to redirect guide wires during guide wire probing. Specific uses for the sheath devices include, but are not limited to, the introduction and support of various interventional and diagnostic devices when performing procedures such as sinus ostia dilation, sinus lavage, and suction. The sheath devices may also be used for other applications including, but not limited to treatment of the middle ear via the Eustachian tube, etc.

Figure 14:
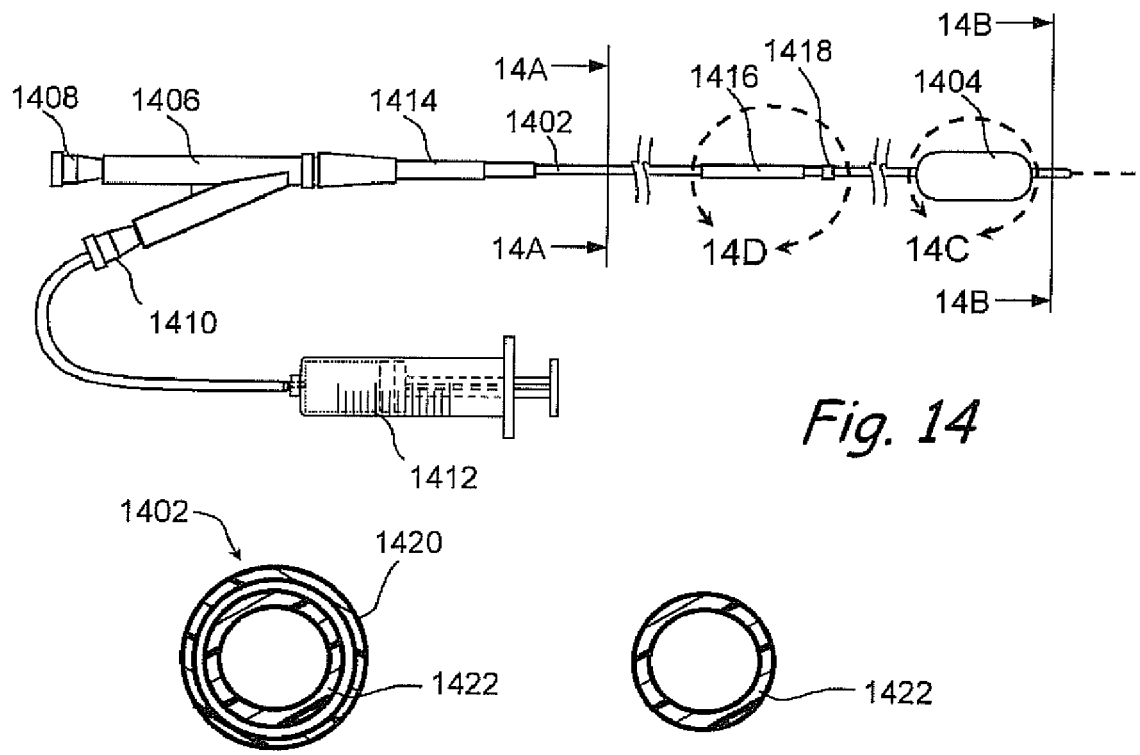
FIG. 14 is a side view of a balloon catheter device of the present invention.
Figure 14:
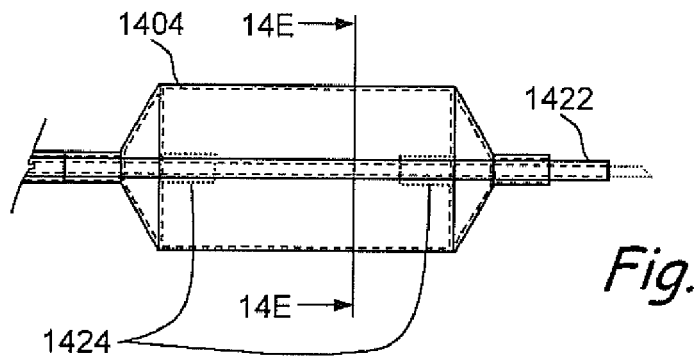
Figure 14:
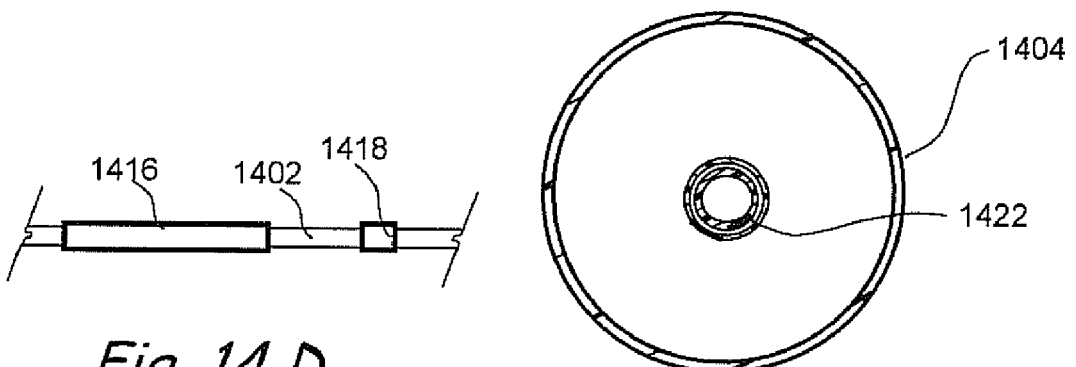

FIG. 14 shows a side view of en embodiment of a balloon catheter. The balloon catheter design disclosed in FIG. 14 may be used as balloon catheter 934 in FIG. 9D. In FIG. 14, balloon catheter 1400 comprises an elongate shaft 1402. In one embodiment, outer diameter of elongate shaft 1402 is around 0.046"+/−0.005". In another embodiment, outer diameter of elongate shaft 1402 is around 0.066"+/−0.005". Elongate shaft 1402 comprises a guidewire lumen to allow balloon catheter 1400 to be introduced over a guidewire such as a 0.035" guidewire. A balloon 1404 is located on the distal portion of elongate shaft 1402. In one embodiment, balloon 1404 is a non-compliant balloon of compliance ranging from 0.025 to 0.030 mm per atmosphere. Balloon 1404 may be made of suitable biocompatible materials including, but not limited to PET, Nylon, etc. Balloon 1404 may be coated with one or more balloon coatings including, but not limited to puncture resistance coating, abrasion resistance coating, anti-tack coating, etc. In a particular embodiment, balloon 1404 is made of PET of a wall thickness around 0.002 inches coated by a 0.002 inch thick polyurethane coating with a tensile strength of 12,000 to 16,000 psi and a burst pressure of more than 16 atmospheres. The working length of balloon 1404 may range from 4 mm to 50 mm. In one embodiment, working length of balloon is around 16+/−1 mm. Balloon 1404 may be inflated to a suitable working pressure of around 12 to 16 atmospheres. In one embodiment of a system comprising multiple balloon catheters, three balloon catheters of inflated balloon diameters around 3+/−0.5 mm, 5+/−0.5 mm and 7+/−0.5 mm are provided in the system. In another embodiment of a system comprising multiple balloon catheters, two balloon catheters of inflated balloon diameters around 5+/−0.5 mm and 7+/−0.5 mm are provided in the system. Balloon catheter 1400 of an inflated balloon diameter around 7 mm is especially suitable for dilating passageways leading to the maxillary sinuses. Balloon catheter 1400 of an inflated balloon diameter around 9 mm is especially suitable for dilating passageways leading to the paranasal sinuses in patients that have undergone a previous sinus surgery. Balloon 1404 may be folded to reduce its profile. The folding may be done to produce multiple folded wings of the balloon material. For example, a 7 mm diameter balloon may be folded to produce 4 to 7 folded wings of the balloon material. In the embodiment of balloon catheter 1400 shown in FIG. 14, the proximal end of balloon catheter 1400 comprises a 'Y' connector 1406. The proximal end of 'Y' connector 1406 comprises a first luer port 1408 that leads to a guidewire lumen in balloon catheter 1400. 'Y' connector 1406 further comprises a second luer port 1410 that is in fluid communication with a balloon inflation lumen in balloon catheter 1400. Balloon 1404 is inflated by injecting a suitable inflation medium such as diluted contrast solution through second luer port 1410 by an inflation device 1412. In one embodiment, inflation device 1412 is connected to second luer port 1410 by a segment of extension tubing. A stress relief tubing 1414 may be located between 'Y' connector 1406 and elongate shaft 1402. Elongate shaft 1402 may comprise a first catheter shaft marker 1416 with or without a second catheter shaft marker 1418. In one embodiment, length of balloon catheter 1400 is 30+/−1 cm.

FIGS. 14A and 14B show cross sectional views of the balloon catheter of FIG. 14 through lines 14A-13A and 14B-13B respectively. FIG. 14A shows a cross section of elongate shaft 1402. Elongate shaft 1402 comprises an outer tube 1420 and an inner tube 1422. Outer tube 1420 and inner tube 1422 can be made of suitable biocompatible polymers including, but not limited to Pebax, Nylon, etc. Inner tube 1422 encloses a guidewire lumen. In one embodiment, the guidewire lumen has an internal diameter greater than 0.0155 inches to enable insertion of balloon catheter 1400 into the anatomy over a 0.014" guidewire. In another embodiment, the guidewire lumen has an internal diameter greater than 0.0360 inches to enable insertion of balloon catheter 1400 into the anatomy over a 0.035" guidewire. The lumen between outer tube 1420 and an inner tube 1422 encloses a balloon inflation lumen that is in fluid communication with balloon 1404. FIG. 14B shows a cross section of elongate shaft 1402 at a region distal to balloon 1404. Elongate shaft 1402 comprises an inner tube 1422 without outer tube 1420 since outer tube 1420 opens into balloon 1404. FIG. 14C shows an enlarged view of segment 14C of FIG. 14. Distal end of outer tube 1420 opens into balloon 1404. In one embodiment, the length of inner tube 1422 distal to balloon 1404 is 3.0+/−0.75 mm. In another embodiment, the length of inner tube 1422 distal to balloon 1404 is 5.0+/−0.75 mm. In this example, balloon 1404 is a standard balloon comprising a cylindrical body, two conical tapers, and two necks. Alternatively, balloon 1404 may also comprise other types of balloon designs. The portion of inner tube 1422 enclosed by balloon 1404 may comprise one or more radiographic markers. In this example, inner tube 1422 comprises two radiographic markers 1424. Radiographic markers 1424 are used to verify the position of balloon 1404 during the use of balloon catheter 1400. FIG. 14D shows an enlarged perspective view of segment 14D in FIG. 14. Elongate shaft 1402 comprises visual markers such as a first catheter shaft marker 1416 and a second catheter shaft marker 1418. The visual markers are used to verify relative location of balloon 1404 relative to distal end of a guide device when balloon catheter 1404 is introduced through the guide device. When second balloon catheter shaft marker 1481 enters the proximal end of the guide device, the distal tip of balloon catheter 1400 emerges out of the distal end of the guide device. First catheter shaft marker 1416 starts to enter the proximal end of the guide device when the material of balloon 1404 starts to emerge out of the distal end of the guide device. First catheter shaft marker 1416 completely enters proximal end of the guide device when material of balloon 938 completely emerges out of the distal end of the guide device. Thus, erroneous inflation of balloon 1404 within the guide device can be prevented. In one embodiment, the distance from the distal end of first catheter shaft marker 1316 and the distal tip of balloon catheter 1400 is 15.0+/−1.0 cm. FIG. 14E shows a cross sectional view of the balloon in FIG. 14C through line 14E-14E. Inner tube 1422 is surrounded by balloon 1404.

Balloon 1404 is made of suitable biocompatible materials and may comprise one or more coatings on the outer surface of balloon 1404.

A probing tool could be used in conjunction with the various methods and devices disclosed herein. The probing tool is a generally rigid, elongate element that is inserted through the nose. The distal end of the probing tool may be substantially straight or may comprise a curved, angled or bent region. The distal region or end of the probing tool is advanced to reach an opening of a paranasal sinus (e.g., any transnasally accessible opening in a paranasal sinus or cranio-facial air cell, including but not limited to; natural ostia, surgically or medically altered ostia, surgically created or man made openings, antrostomy openings, ostiotomy openings, trephination openings, burr holes, drilled holes, ethmoidectomy or an anatomical region substantially near such opening of a paranasal sinus. The probing tool is then used to determine the location and/or that opening or anatomical region. Information about the location and/or the orientation of that opening or anatomical region can be appreciated or determined in many ways.

For example, the orientation of the proximal region of the probing tool outside the nose provides the user information about the location and/or the orientation of the opening or anatomical region. In a second embodiment, the location and/or orientation of the probing tool in the anatomy is visualized under endoscopic and/or fluoroscopic visualization to provide the user information about the location and/or the orientation of the opening or anatomical region. In a third embodiment, the probing tool comprises a navigational modality such as an electromagnetic surgical navigation modality. The location and orientation of the distal region of the probing tool can then be visualized using the electromagnetic surgical navigation modality to obtain information about the location and/or the orientation of the opening or anatomical region. The information about the location and/or the orientation of an opening or anatomical region is then used to plan the trajectory of introducing one or more diagnostic, therapeutic or introducing devices into the opening or anatomical region. This has the advantage of reducing procedure time. Examples of such probing tools include, but are not limited to frontal sinus seekers, maxillary sinus seekers, etc. The probing tools may be solid or may comprise a lumen. The diagnostic, therapeutic or introducing devices may be introduced over the probing devices, through the probing device or may replace the probing device. The probing tools may be made of suitable biocompatible materials including, but not limited to stainless steel, Nitinol, polymers etc.

As described herein, the present invention includes methods for accessing an opening of a paranasal sinus (e.g., any transnasally accessible opening in a paranasal sinus or cranio-facial air cell, including but not limited to; natural ostia, surgically or medically altered ostia, surgically created or man made openings, antrostomy openings, ostiotomy openings, trephination openings, burr holes, drilled holes, ethmoidectomy openings, anatomical passageways, natural or man made passages, etc.) or other anatomical region substantially near such opening of a paranasal sinus. In these methods a probing tool, such as a maxillary sinus seeker, is used to determine the location and orientation of the opening or anatomical region (e.g., the maxillary sinus ostium). In the case of a maxillary sinus ostium, this is done by navigating the distal region of the maxillary sinus seeker around the uncinate process such that the distal end of the maxillary sinus seeker enters the maxillary sinus ostium. The position and orientation of the proximal region of the maxillary sinus seeker is then used to determine the location and/or orientation of the maxillary sinus ostium. Thereafter, the maxillary sinus seeker is removed from the anatomy. Thereafter, a diagnostic or therapeutic device e.g. a fixed wire balloon catheter is used to access the maxillary sinus ostium. Alternatively, an access device e.g. a guide device may be placed in a suitable location and orientation and a diagnostic or therapeutic device may be advanced into the maxillary sinus ostium using the guide device.

In another embodiment of a method of accessing an ostium or a passageway leading to a paranasal sinus, a probing tool such as a frontal sinus seeker comprising a lumen is used to determine the location and orientation of the passageway leading to a frontal sinus. Thereafter, a guidewire is introduced through the lumen of the frontal sinus seeker into the frontal sinus. Thereafter, the frontal sinus seeker is exchanged over the guidewire for a diagnostic or therapeutic device such as a balloon catheter.

The term "diagnostic or therapeutic substance" as used herein is to be broadly construed to include any feasible drugs, prodrugs, proteins, gene therapy preparations, cells, diagnostic agents, contrast or imaging agents, biologicals, etc. Such substances may be in bound or free form, liquid or solid, colloid or other suspension, solution or may be in the form of a gas or other fluid or nan-fluid. For example, in some applications where it is desired to treat or prevent a microbial infection, the substance delivered may comprise pharmaceutically acceptable salt or dosage form of an antimicrobial agent (e.g., antibiotic, antiviral, antiparasitic, antifungal, etc.), a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), etc. Other non-limiting examples of diagnostic or therapeutic substances that may be useable in this invention are described in copending U.S. patent application Ser. No. 10/912,578 entitled Implantable Devices and Methods for Delivering Drugs and Other Substances to Treat Sinusitis and Other Disorders filed on Aug. 4, 2004, the entire disclosure of which is expressly incorporated herein by reference.

The term "nasal cavity" used herein to be broadly construed to include any cavity that is present in the anatomical structures of the nasal region including the nostrils and paranasal sinuses.

The term "trans-nasal" means through a nostril.

Reference herein to an "opening of a paranasal sinus" pr "opening in a paranasal sinus" shall mean: any transnasally accessible opening in a paranasal sinus or cranio-facial air cell, including but not limited to; natural ostia, surgically or medically altered ostia, surgically created or man made openings, antrostomy openings, ostiotomy openings, trephination openings, burr holes, drilled holes, ethmoidectomy openings, anatomical passageways, natural or man made passages, etc.

Although the methods and devices disclosed herein are illustrated in conjunction with particular paranasal sinuses, it is understood that these methods and devices can be used in other paranasal sinuses as well as other anatomical passageways of the ear, nose or throat.

Optionally, any of the working devices and guide catheters described herein may be configured or equipped to receive or be advanced over a guidewire or other guide member (e.g., an elongate probe, strand of sure material, other elongate member) unless to do so would render the device inoperable for its intended purpose. Some of the specific examples described herein include guidewires, but it is to be appreciated that the use of guidewires and the incorporation of guidewire lumens is not limited to only the specific examples in which guidewires or guidewire lumens are shown. The guidewires used in this invention may be constructed and coated as is common in the art of cardiology. This may include the use of coils, tapered or non-tapered core wires, radioopaque tips and/or entire lengths, shaping ribbons, variations of stiffness, PTFE, silicone, hydrophilic coatings, polymer coatings, etc. For the scope of this invention, these wires may possess dimensions of length between 5 and 75 cm and outer diameter between 0.005" and 0.050".

Several modalities can be used with the devices and methods disclosed herein for navigation and imaging of the devices within the anatomy. For example, the devices disclosed herein may comprise an endoscope for visualization of the target anatomy. The devices may also comprise ultrasound imaging modalities to image the anatomical passageways and other anatomical structures. The devices disclosed herein may comprise one or more magnetic elements especially on the distal end of the devices. Such magnetic elements may be used to navigate through the anatomy by using external magnetic fields. Such navigation may be controlled digitally using a computer interface. The devices disclosed herein may also comprise one or more markers (e.g. infra-red markers). The markers can be used to track the precise position and orientation of the devices using image guidance techniques. Several other imaging or navigating modalities including but not limited to fluoroscopic, radiofrequency localization, electromagnetic, magnetic and other radiative energy based modalities may also be used with the methods and devices disclosed herein. These imaging and navigation technologies may also be referenced by computer directly or indirectly to pre-existing or simultaneously created 3-D or 2-D data sets which help the doctor place the devices within the appropriate region of the anatomy.

The distal tip of devices mentioned herein may comprise a flexible tip or a soft, atraumatic tip. Also, the shaft of such devices may be designed for enhanced torquability.

The embodiments herein have been described primarily in conjunction with minimally invasive procedures, but they can also be used advantageously with existing open surgery or laparoscopic surgery techniques.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example un-novel, obvious to a person of ordinary skill in the relevant art or unsuitable for its intended use. All reasonable additions, deletions, modifications and alterations are to be considered equivalents of the described examples and embodiments and are to be included within the scope of the following claims.

The invention claimed is:

1. A method of performing a surgery on a paranasal sinus of a human or animal subject, said method comprising:
   inserting an endoscope into a head of the subject;
   inserting an at least partially rigid guide tool into the head to position a distal end of the guide tool at or near an opening of the paranasal sinus and at least part of the guide tool within a field of view of the endoscope;
   advancing at least one tubular device that has at least one flexible region along the guide tool to advance a distal end of the tubular device through the opening of the paranasal sinus and outside the field of view of the endoscope; and
   performing a surgery on the paranasal sinus using the tubular device, wherein at least a portion of the tubular device remains outside the field of view of the endoscope during the surgery.

2. A method according to claim 1, wherein the tubular device comprises a dilator apparatus, and wherein performing the surgery comprises using the dilator apparatus to dilate an opening in the paranasal sinus.

3. A method according to claim 2, wherein the dilator apparatus is advanced distally beyond a terminal end of the endoscope.

4. A method according to claim 2, wherein the dilator apparatus comprises a balloon dilation catheter, wherein using the tubular device comprises inflating a balloon of the catheter to dilate the opening, and wherein a portion of the balloon located on an opposite side of the paranasal sinus opening from the endoscope is outside the field of view when the balloon is inflated.

5. A method according to claim 1, wherein the guide tool comprises a guide catheter, the method further comprising advancing a guidewire through the guide catheter prior to advancing the tubular device, wherein the tubular device is advanced over the guidewire through the guide catheter.

6. A method according to claim 1, further comprising suctioning bodily fluid through the guide tool.

7. A method according to claim 1, further comprising passing irrigation fluid through the tubular device into the paranasal sinus.

8. A method according to claim 1, further comprising suctioning bodily fluid through the tubular device while a distal end of the tubular device is located in the paranasal sinus.

9. A method according to claim 1, wherein the endoscope, guide tool and tubular device are inserted through a nostril of the subject's head.

* * * * *